(12) United States Patent
Drach et al.

(10) Patent No.: US 9,211,059 B2
(45) Date of Patent: Dec. 15, 2015

(54) SYSTEMS AND METHODS FOR OPTIMIZING AND MAINTAINING VISUALIZATION OF A SURGICAL FIELD DURING THE USE OF SURGICAL SCOPES

(75) Inventors: Gregory P Drach, Liberty Township, OH (US); Wayne L Poll, New Albany, OH (US)

(73) Assignee: Minimally Invasive Devices, Inc., Columbus, OH (US)

( * ) Notice: Subject to any disclaimer, the term of this patent is extended or adjusted under 35 U.S.C. 154(b) by 184 days.

(21) Appl. No.: 13/198,406

(22) Filed: Aug. 4, 2011

(65) Prior Publication Data

US 2012/0197084 A1   Aug. 2, 2012

Related U.S. Application Data

(60) Provisional application No. 61/400,900, filed on Aug. 4, 2010, provisional application No. 61/452,982, filed on Mar. 15, 2011.

(51) Int. Cl.
*A61B 1/12*    (2006.01)
*A61B 1/04*    (2006.01)
(Continued)

(52) U.S. Cl.
CPC ............... *A61B 1/126* (2013.01); *A61B 1/0008* (2013.01); *A61B 1/00091* (2013.01); *A61B 1/00101* (2013.01); *A61B 1/00119* (2013.01); *A61B 1/00128* (2013.01); *A61B 1/00135* (2013.01); *A61B 1/015* (2013.01); *A61B 1/127* (2013.01); *A61B 1/3132* (2013.01);
(Continued)

(58) Field of Classification Search
USPC ......... 600/121–125, 127–130, 156–159, 101, 600/170, 171; 604/27, 30–34, 65–67, 93.01
See application file for complete search history.

(56) References Cited

U.S. PATENT DOCUMENTS 3,373,736 A   3/1968   Fiore et al.
D230,727 S   3/1974   Richman
(Continued)

FOREIGN PATENT DOCUMENTS

EP   0664101 A1   7/1995
EP   0790652 A1   8/1997
(Continued)

OTHER PUBLICATIONS

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).
(Continued)

*Primary Examiner* — Ryan Henderson
(74) *Attorney, Agent, or Firm* — Shay Glenn LLP

(57) ABSTRACT

A view optimizing assembly, method and kit for use in combination with a laparoscope having a lens located on the shaft tip of the laparoscope, and a source of insufflation $CO_2$. The invention includes a multi-lumen sheath assembly, a deflector assembly in fluid communication with the lumens of the sheath assembly, wherein the flow of $CO_2$ through the lumens forms a vortex when coming into contact with the deflector assembly, thereby preventing fogging of the laparoscope lens.

17 Claims, 29 Drawing Sheets

(51) Int. Cl.
  *A61B 1/00*        (2006.01)
  *A61B 1/015*       (2006.01)
  *A61B 1/313*       (2006.01)
  *A61B 17/34*       (2006.01)
  *A61M 13/00*       (2006.01)

(52) U.S. Cl.
  CPC ......... *A61B 17/3474* (2013.01); *A61M 13/003* (2013.01); *A61B 2017/347* (2013.01); *A61M 2202/0225* (2013.01); *A61M 2205/3344* (2013.01)

(56) References Cited

U.S. PATENT DOCUMENTS

| | | |
|---|---|---|
| 4,207,874 A | 6/1980 | Choy |
| 4,279,246 A | 7/1981 | Chikama |
| 4,281,646 A | 8/1981 | Kinoshita |
| D277,408 S | 1/1985 | Kubokawa et al. |
| D277,505 S | 2/1985 | Kubokawa et al. |
| 4,497,550 A | 2/1985 | Ouchi et al. |
| 4,537,209 A | 8/1985 | Sasa |
| D280,929 S | 10/1985 | Lystager |
| 4,548,197 A | 10/1985 | Kinoshita |
| 4,552,130 A | 11/1985 | Kinoshita |
| D284,028 S | 5/1986 | Seager |
| 4,598,698 A | 7/1986 | Siegmund |
| 4,616,169 A | 10/1986 | Proffitt |
| 4,617,013 A | 10/1986 | Betz |
| 4,633,855 A | 1/1987 | Baba |
| 4,637,814 A | 1/1987 | Leiboff |
| 4,646,722 A | 3/1987 | Silverstein et al. |
| 4,735,603 A | 4/1988 | Goodson et al. |
| 4,741,326 A | 5/1988 | Sidall et al. |
| 4,748,970 A | 6/1988 | Nakajima |
| 4,760,838 A | 8/1988 | Fukuda |
| 4,773,413 A | 9/1988 | Hussein et al. |
| 4,794,911 A | 1/1989 | Okada |
| 4,800,869 A | 1/1989 | Nakajima |
| 4,877,016 A | 10/1989 | Kantor et al. |
| 4,941,872 A | 7/1990 | Felix et al. |
| 4,973,321 A | 11/1990 | Michelson |
| 4,991,565 A | 2/1991 | Takahashi et al. |
| 4,998,527 A | 3/1991 | Meyer |
| 5,009,655 A | 4/1991 | Daignault, Jr. et al. |
| 5,019,054 A | 5/1991 | Clement et al. |
| 5,027,791 A | 7/1991 | Takahashi |
| 5,050,585 A | 9/1991 | Takahashi |
| 5,133,336 A | 7/1992 | Savitt et al. |
| 5,144,942 A | 9/1992 | Decarie et al. |
| 5,147,292 A | 9/1992 | Kullas et al. |
| 5,163,927 A | 11/1992 | Woker et al. |
| 5,167,220 A | 12/1992 | Brown |
| 5,201,908 A | 4/1993 | Jones |
| 5,207,213 A | 5/1993 | Auhll et al. |
| 5,225,001 A | 7/1993 | Manni et al. |
| 5,279,549 A | 1/1994 | Ranford |
| D346,023 S | 4/1994 | Stewart, Sr. |
| 5,306,272 A | 4/1994 | Cohen et al. |
| 5,312,400 A | 5/1994 | Bales et al. |
| 5,313,934 A | 5/1994 | Wiita et al. |
| 5,320,091 A | 6/1994 | Grossi et al. |
| 5,328,458 A | 7/1994 | Sekino et al. |
| 5,336,170 A | 8/1994 | Salerno et al. |
| 5,339,800 A | 8/1994 | Wiita et al. |
| 5,359,991 A | 11/1994 | Takahashi et al. |
| 5,364,407 A | 11/1994 | Poll |
| 5,386,817 A | 2/1995 | Jones |
| 5,392,766 A | 2/1995 | Masterson et al. |
| 5,400,767 A | 3/1995 | Murdoch |
| 5,448,891 A | 9/1995 | Nakagiri et al. |
| 5,448,990 A | 9/1995 | De Faria-Correa |
| 5,464,008 A | 11/1995 | Kim |
| 5,468,240 A | 11/1995 | Gentelia et al. |
| D369,862 S | 5/1996 | Stewart, Jr. |
| 5,514,084 A | 5/1996 | Fisher |
| 5,518,502 A | 5/1996 | Kaplan et al. |
| 5,562,600 A | 10/1996 | Matsuno |
| 5,563,737 A | 10/1996 | Kamrat |
| 5,569,157 A | 10/1996 | Nakazawa et al. |
| 5,575,753 A | 11/1996 | Yabe et al. |
| 5,575,756 A | 11/1996 | Karasawa et al. |
| 5,605,532 A | 2/1997 | Schermerhorn |
| 5,630,795 A | 5/1997 | Kuramoto et al. |
| 5,637,075 A | 6/1997 | Kikawada |
| 5,647,840 A | 7/1997 | D'Amelio et al. |
| 5,697,888 A | 12/1997 | Kobayashi et al. |
| 5,746,695 A | 5/1998 | Yasui et al. |
| 5,788,628 A | 8/1998 | Matsuno et al. |
| 5,857,961 A | 1/1999 | Vanden Hoek et al. |
| 5,865,730 A | 2/1999 | Fox et al. |
| 5,868,663 A | 2/1999 | Katsurada et al. |
| 5,869,107 A | 2/1999 | Shimizu et al. |
| 5,894,369 A | 4/1999 | Akiba et al. |
| 5,922,105 A | 7/1999 | Fujii et al. |
| 5,954,637 A | 9/1999 | Francis |
| 5,957,888 A | 9/1999 | Hinchliffe |
| 5,989,183 A | 11/1999 | Reisdorf et al. |
| 6,017,333 A | 1/2000 | Bailey |
| 6,040,053 A | 3/2000 | Scholz et al. |
| 6,071,606 A | 6/2000 | Yamazaki et al. |
| D428,487 S | 7/2000 | Renner et al. |
| 6,096,026 A | 8/2000 | Schultz |
| 6,110,103 A | 8/2000 | Donofrio |
| 6,110,259 A | 8/2000 | Schultz et al. |
| 6,126,592 A | 10/2000 | Proch et al. |
| 6,149,659 A | 11/2000 | Ahmed |
| 6,156,409 A | 12/2000 | Doushita et al. |
| 6,176,825 B1 | 1/2001 | Chin et al. |
| 6,206,825 B1 | 3/2001 | Tsuyuki |
| 6,234,635 B1 | 5/2001 | Seitzinger et al. |
| 6,282,442 B1 | 8/2001 | DeStefano et al. |
| 6,299,592 B1 | 10/2001 | Zander |
| 6,306,932 B1 | 10/2001 | Yamamoto et al. |
| 6,354,992 B1 | 3/2002 | Kato |
| 6,361,492 B1 | 3/2002 | Santilli |
| 6,383,134 B1 | 5/2002 | Santilli |
| 6,409,657 B1 | 6/2002 | Kawano |
| 6,425,535 B1 | 7/2002 | Akiba |
| 6,447,446 B1 | 9/2002 | Smith et al. |
| 6,582,357 B2 | 6/2003 | Ouchi et al. |
| 6,589,316 B1 | 7/2003 | Schultz et al. |
| D481,126 S | 10/2003 | Hayamizu |
| 6,645,197 B2 | 11/2003 | Garrison et al. |
| D484,594 S | 12/2003 | Hayamizu |
| D486,910 S | 2/2004 | Hayamizu et al. |
| 6,695,772 B1 | 2/2004 | Bon et al. |
| 6,699,185 B2 | 3/2004 | Gminder et al. |
| 6,712,479 B1 | 3/2004 | Seitzinger et al. |
| 6,712,757 B2 | 3/2004 | Becker et al. |
| 6,712,759 B2 | 3/2004 | Muller |
| 6,752,755 B2 | 6/2004 | Akiba |
| 6,755,782 B2 | 6/2004 | Ogawa |
| D493,529 S | 7/2004 | Hayamizu et al. |
| 6,764,445 B2 | 7/2004 | Ramans et al. |
| 6,780,516 B2 | 8/2004 | Chen |
| 6,783,845 B2 | 8/2004 | Zhang et al. |
| D498,846 S | 11/2004 | Hayamizu et al. |
| 6,814,697 B2 | 11/2004 | Ouchi |
| 6,857,436 B2 | 2/2005 | Labib et al. |
| 6,858,005 B2 | 2/2005 | Ohline et al. |
| 6,882,236 B2 | 4/2005 | Dinn et al. |
| 6,889,400 B2 | 5/2005 | Kawazoe et al. |
| 6,921,362 B2 | 7/2005 | Ouchi |
| 6,921,380 B1 | 7/2005 | Epstein et al. |
| 6,977,053 B2 | 12/2005 | Mukasa et al. |
| 6,984,204 B2 | 1/2006 | Akiba |
| 6,989,183 B2 | 1/2006 | McKillip |
| 7,074,180 B2 | 7/2006 | Bertolero et al. |
| 7,080,641 B2 | 7/2006 | Gomez |
| 7,087,013 B2 | 8/2006 | Belson et al. |
| 7,150,713 B2 | 12/2006 | Shener et al. |
| D534,655 S | 1/2007 | Iranyi et al. |
| D535,743 S | 1/2007 | Williams |

(56) References Cited

U.S. PATENT DOCUMENTS

| | | |
|---|---|---|
| 7,169,167 B2 | 1/2007 | Chu |
| 7,198,599 B2 | 4/2007 | Goto et al. |
| 7,223,231 B2 | 5/2007 | Akiba |
| 7,250,028 B2 | 7/2007 | Julian et al. |
| 7,270,670 B1 | 9/2007 | Yencho |
| 7,341,556 B2 | 3/2008 | Shalman |
| D573,711 S | 7/2008 | Johnson et al. |
| 7,413,543 B2 | 8/2008 | Banik et al. |
| D600,807 S | 9/2009 | Dienst et al. |
| D613,403 S | 4/2010 | Poll et al. |
| 7,803,109 B2 | 9/2010 | Gomez |
| 7,803,144 B1 | 9/2010 | Vollrath |
| 7,927,271 B2 | 4/2011 | Dimitriou et al. |
| 8,047,215 B1 | 11/2011 | Sasaki |
| 8,062,214 B2 | 11/2011 | Shener et al. |
| 8,075,481 B2 | 12/2011 | Park et al. |
| 8,096,944 B2 | 1/2012 | Harrel |
| 8,226,549 B2 | 7/2012 | Kumar et al. |
| 8,419,624 B2 | 4/2013 | James et al. |
| 8,517,921 B2 | 8/2013 | Tremaglio et al. |
| 8,545,395 B2 | 10/2013 | Akahoshi et al. |
| 2001/0011162 A1 | 8/2001 | Epstein |
| 2002/0022762 A1 | 2/2002 | Beane et al. |
| 2002/0058858 A1 | 5/2002 | Ogura et al. |
| 2002/0072652 A1 | 6/2002 | Berci et al. |
| 2002/0091304 A1 | 7/2002 | Ogura et al. |
| 2002/0173699 A1* | 11/2002 | Becker et al. .................. 600/114 |
| 2002/0193806 A1 | 12/2002 | Moenning et al. |
| 2003/0200738 A1 | 10/2003 | Booth |
| 2004/0034339 A1 | 2/2004 | Stoller et al. |
| 2004/0059363 A1 | 3/2004 | Alvarez et al. |
| 2004/0082915 A1 | 4/2004 | Kadan |
| 2004/0204671 A1 | 10/2004 | Stubbs et al. |
| 2005/0043683 A1 | 2/2005 | Ravo |
| 2005/0059981 A1 | 3/2005 | Poll |
| 2005/0065405 A1 | 3/2005 | Hasegawa |
| 2005/0113797 A1 | 5/2005 | Ott et al. |
| 2005/0119528 A1 | 6/2005 | Weinberg |
| 2005/0137529 A1 | 6/2005 | Mantell |
| 2005/0154355 A1 | 7/2005 | Gross et al. |
| 2005/0159765 A1 | 7/2005 | Moutafis et al. |
| 2005/0171467 A1 | 8/2005 | Landman |
| 2005/0171528 A1 | 8/2005 | Sartor et al. |
| 2005/0203342 A1 | 9/2005 | Kucklick et al. |
| 2005/0234301 A1 | 10/2005 | Gomez |
| 2005/0261553 A1 | 11/2005 | Swain et al. |
| 2006/0020165 A1 | 1/2006 | Adams |
| 2006/0041186 A1 | 2/2006 | Vancaillie |
| 2006/0047184 A1 | 3/2006 | Banik et al. |
| 2006/0052661 A1 | 3/2006 | Gannot et al. |
| 2006/0069306 A1 | 3/2006 | Banik et al. |
| 2006/0252993 A1 | 11/2006 | Freed et al. |
| 2006/0270910 A1 | 11/2006 | Davis |
| 2007/0088275 A1 | 4/2007 | Stearns et al. |
| 2007/0179432 A1 | 8/2007 | Bar et al. |
| 2007/0182842 A1 | 8/2007 | Sonnenschein et al. |
| 2007/0203474 A1 | 8/2007 | Ryan et al. |
| 2007/0282253 A1 | 12/2007 | Sasaki |
| 2007/0289449 A1 | 12/2007 | Roberts et al. |
| 2007/0299310 A1 | 12/2007 | Phillips |
| 2008/0021277 A1 | 1/2008 | Stefanchik et al. |
| 2008/0051631 A1 | 2/2008 | Dejima et al. |
| 2008/0081948 A1 | 4/2008 | Weisenburgh et al. |
| 2008/0086704 A1 | 4/2008 | Aravamudan |
| 2008/0108871 A1 | 5/2008 | Mohr |
| 2008/0161646 A1 | 7/2008 | Gomez |
| 2008/0188715 A1* | 8/2008 | Fujimoto .................. 600/157 |
| 2008/0200765 A1 | 8/2008 | Mondschein |
| 2008/0208128 A1 | 8/2008 | Guo et al. |
| 2008/0249362 A1 | 10/2008 | Jiang et al. |
| 2008/0319266 A1 | 12/2008 | Poll et al. |
| 2009/0018602 A1 | 1/2009 | Mitelberg et al. |
| 2009/0113644 A1 | 5/2009 | Heck |
| 2009/0215018 A1 | 8/2009 | Edmondson et al. |
| 2009/0253962 A1 | 10/2009 | Fernandez et al. |
| 2009/0253965 A1 | 10/2009 | Miyamoto |
| 2010/0168520 A1 | 7/2010 | Poll et al. |
| 2010/0198014 A1 | 8/2010 | Poll et al. |
| 2010/0331856 A1 | 12/2010 | Carlson et al. |
| 2012/0022331 A1 | 1/2012 | Poll et al. |
| 2012/0101337 A1 | 4/2012 | Clark et al. |
| 2012/0165610 A1 | 6/2012 | Poll et al. |
| 2012/0184897 A1 | 7/2012 | Poll |
| 2012/0310147 A1 | 12/2012 | Poll et al. |
| 2013/0317295 A1 | 11/2013 | Morse |
| 2014/0114128 A1 | 4/2014 | Wills |

FOREIGN PATENT DOCUMENTS

| | | | |
|---|---|---|---|
| EP | 1188415 A2 | 3/2002 | |
| JP | 59-203534 | 11/1984 | |
| JP | 61-168328 | 7/1986 | |
| JP | 05-199979 | 8/1993 | |
| JP | 09-135804 | 5/1997 | |
| JP | 2000-225093 | 8/2000 | |
| JP | 2005-110978 | 4/2005 | |
| WO | WO 9210969 A1 * | 7/1992 | ............... A61B 1/00 |
| WO | WO92/22238 A1 | 12/1992 | |
| WO | WO2005/002210 A1 | 1/2005 | |
| WO | WO2005/009227 A1 | 2/2005 | |
| WO | WO2005/115221 A1 | 12/2005 | |
| WO | WO2006/014814 A1 | 2/2006 | |
| WO | WO2008/030256 A1 | 3/2008 | |
| WO | WO2008/077080 A2 | 6/2008 | |
| WO | WO2008/128142 A2 | 10/2008 | |
| WO | WO2008/130582 A2 | 10/2008 | |
| WO | WO2009/073577 A2 | 6/2009 | |
| WO | WO2010/042913 A2 | 4/2010 | |
| WO | WO2010/042915 A2 | 4/2010 | |
| WO | WO2011/041387 A1 | 4/2011 | |
| WO | WO2011/044448 A2 | 4/2011 | |
| WO | WO2011/130399 A1 | 10/2011 | |
| WO | WO2012/005819 A1 | 1/2012 | |
| WO | WO2012/044410 A2 | 4/2012 | |
| WO | WO2012/122263 A2 | 9/2012 | |

OTHER PUBLICATIONS

Poll et al.; Design U.S. App. No. 29/329,224 entitled "Manifold Coupling," filed Dec. 10, 2008 (now abandoned).
Poll et al.; Design U.S. App. No. 29/329,225 entitled "Sheath Manifold for Maintaining Surgical Scope Visualization," filed Dec. 10, 2008 (now abandoned).
Poll et al.; Design U.S. App. No. 29/329,221 entitled "Handle for Maintaining Surgical Scope Visualization," filed Dec. 10, 2008 (now abandoned).
Poll et al.; Design U.S. App. No. 29/335,699 entitled "Surgical Scope Stabilizer," filed Apr. 20, 2009 (now abandoned).
Search Report/Written Opinion dated Dec. 6, 2011 in International Patent Application Serial No. PCT/US 11/46621.
International Preliminary Report on Patentability for PCT/US11/46621, dated Aug. 6, 2012.
Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.
Hashimoto et al.; Development of a fogless scope and its analysis using infrared radiation pyrometer; Surg Endosc; 11(8); pp. 805-808; Aug. 1997.
Lawrentschuk et al.; Laparoscopic lens fogging: A review of etiology and methods to maintain a clear visual field; Journal of Endourology; 24(6); pp. 905-913; Jun. 2010.
Ohdaira et al.; Antifogging effects of a socket-type device with the superhydrophilic, titanium dioxide coated glass for laparoscope; Surg endosc; 21(2); pp. 333-338; Dec. 2007.
Poll et al.; U.S. App. No. 14/308,644 entitled "Sheath for hand-held and robotic laparoscopes," filed Jun. 18, 2014.
Poll et al.; U.S. App. No. 14/490,501 entitled "Systems and methods for optimizing and maintaining visualization of a surgical field during the use of surgical scopes," filed Sep. 18, 2014.

* cited by examiner

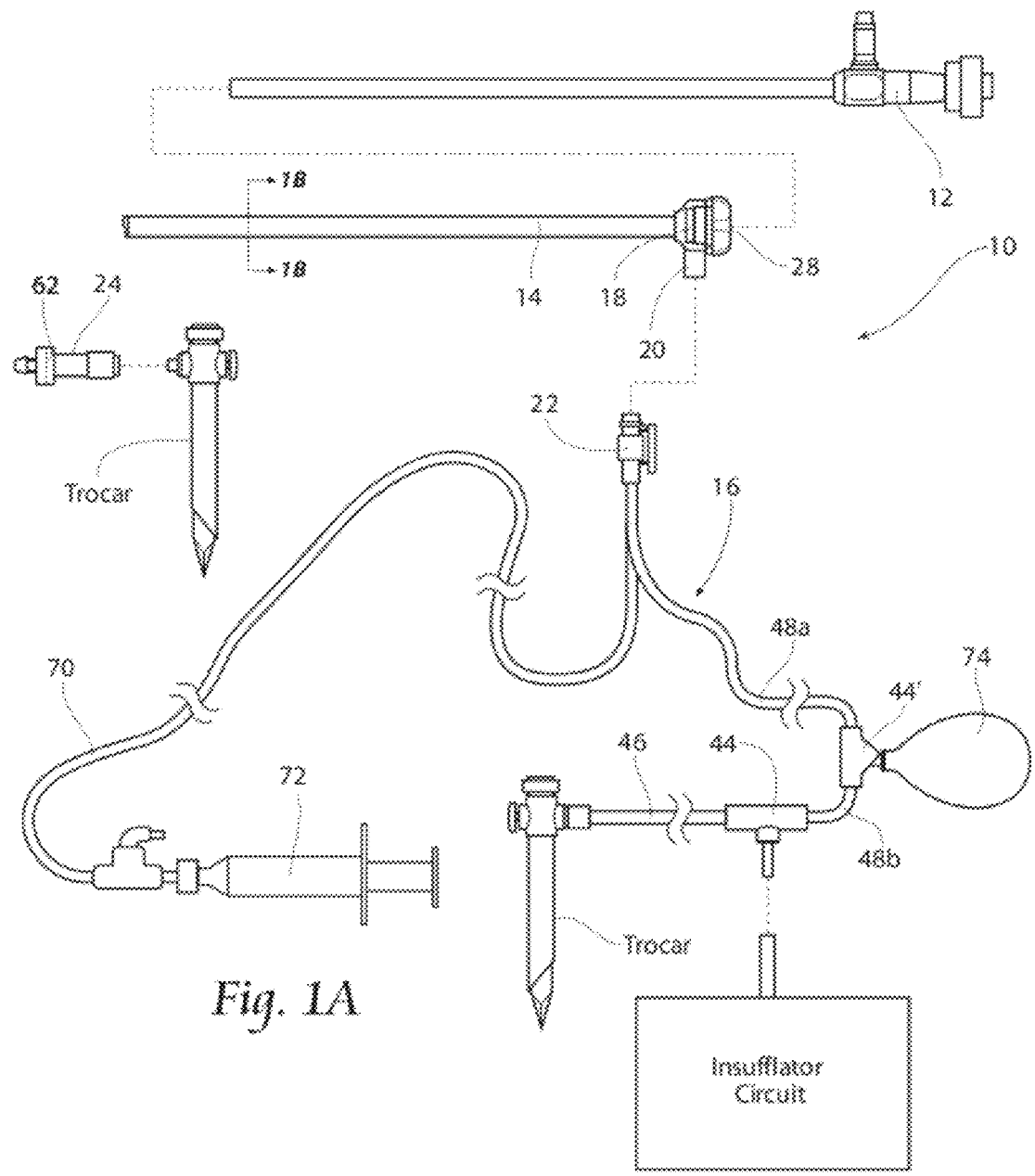
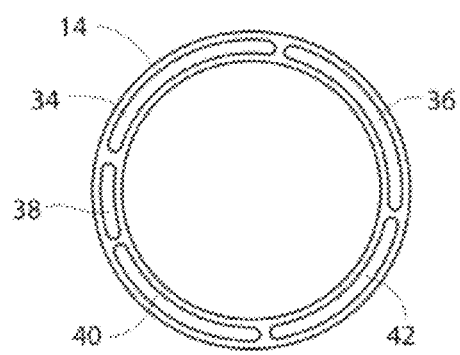
Fig. 1A
Fig. 1B

NORMAL OPERATING PROCEDURE

*STERILE FLUID INJECTION TO CLEAR DEBRIS*

BURST OF CO2
TO CLEAR BUBBLES

BUBBLES EXIT AT
PRESSURE RELEASE VALVE

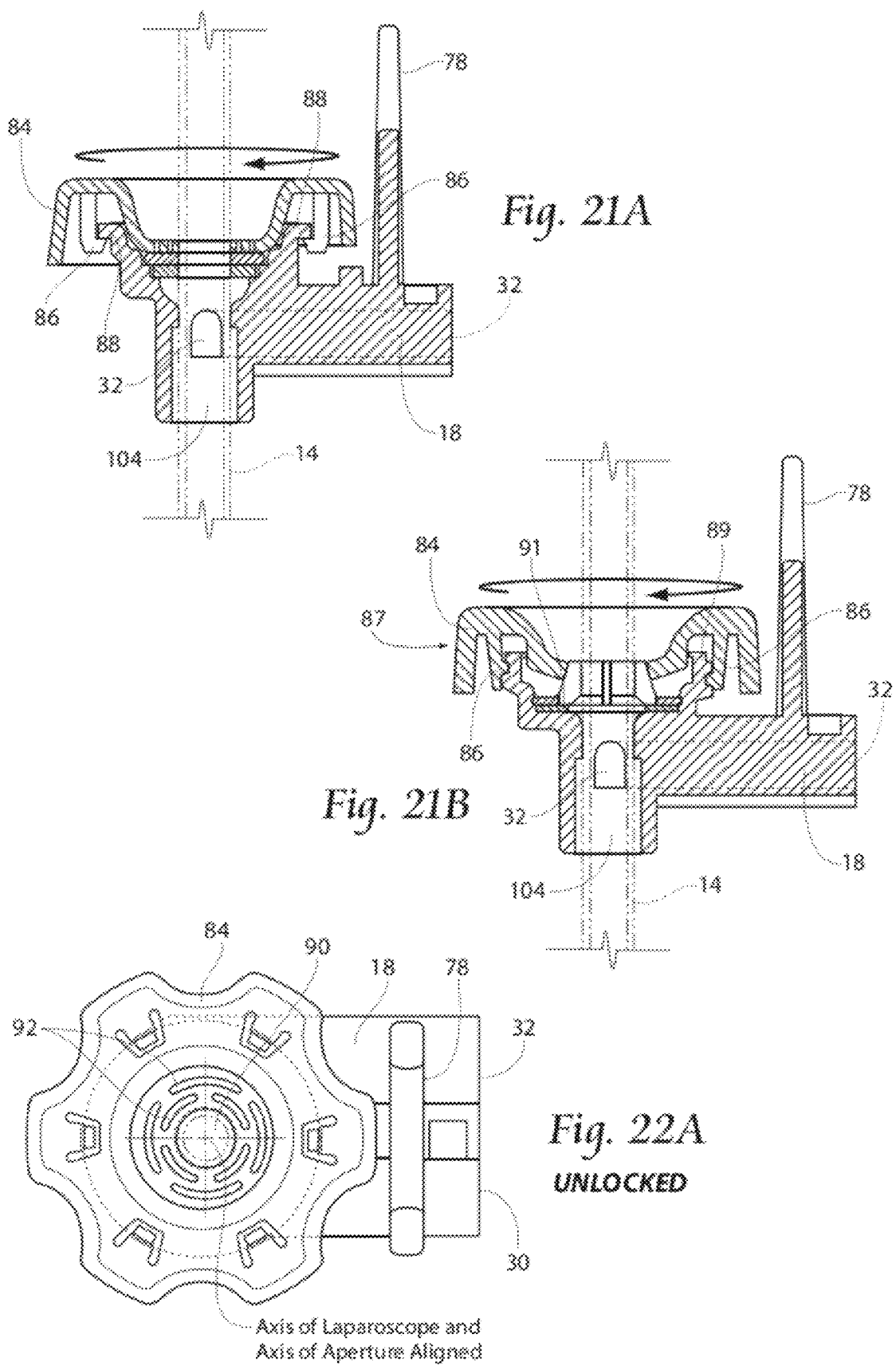

*LOCKED*

*UNLOCKED*

*LOCKED*

SYSTEMS AND METHODS FOR OPTIMIZING AND MAINTAINING VISUALIZATION OF A SURGICAL FIELD DURING THE USE OF SURGICAL SCOPES

RELATED APPLICATION

This application claims priority to U.S. Provisional Patent Application Ser. No. 61/400,900, filed Aug. 4, 2010, entitled "Systems and Methods for Optimizing and Maintaining Visualization of a Surgical Field During the Use of Surgical Scopes" and U.S. Provisional Patent Application Ser. No. 61/452,982, filed Mar. 15, 2011, entitled "Systems and Methods for Optimizing and Maintaining Visualization of a Surgical Field During the Use of Surgical Scopes."

FIELD OF THE INVENTION

The invention generally relates to surgical scopes, and, more particularly, for optimizing and maintaining visualization of a surgical field when using a surgical scope, such as, e.g., a laparoscope.

BACKGROUND OF THE INVENTION

Minimally invasive surgical procedures utilizing surgical scopes are desirable because they often provide one or more of the following advantages: reduced blood loss; reduced post-operative patient discomfort; shortened recovery and hospitalization time; smaller incisions; and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

SUMMARY OF THE INVENTION

One aspect of the invention provides a view optimizing assembly having a deflector assembly that makes possible intra-operative defogging, surgical debris deflection, and cleaning of a laparoscope lens during minimally invasive surgery, while also maintaining visualization of the surgical site. In use, the view optimizing assembly makes possible the practice of a surgical method for maintaining clear visualization of the surgical site without removing the laparoscope 12 from the abdominal cavity for the purpose of cleaning or de-fogging its lens.

BRIEF DESCRIPTION OF THE DRAWINGS

FIG. 1A is a somewhat schematic, exploded view of a view optimizing assembly for use with a laparoscope having a 0° shaft tip.

FIG. 1B is a section view of the sheath, showing internal fluid flow lumens, taken generally along line 1B-1B in FIG. 1A.

FIG. 21A is a side section view of the manifold showing details of the locking collar.

FIG. 21B is a side section view of an alternative arrangement of the manifold employing an alternative locking collar.

FIGS. 22A and 22B are views of the locking collar when unlocked (FIG. 22A) and locked (FIG. 22B).

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. VIEW OPTIMIZING ASSEMBLY

A. Overview

Figure 2A:
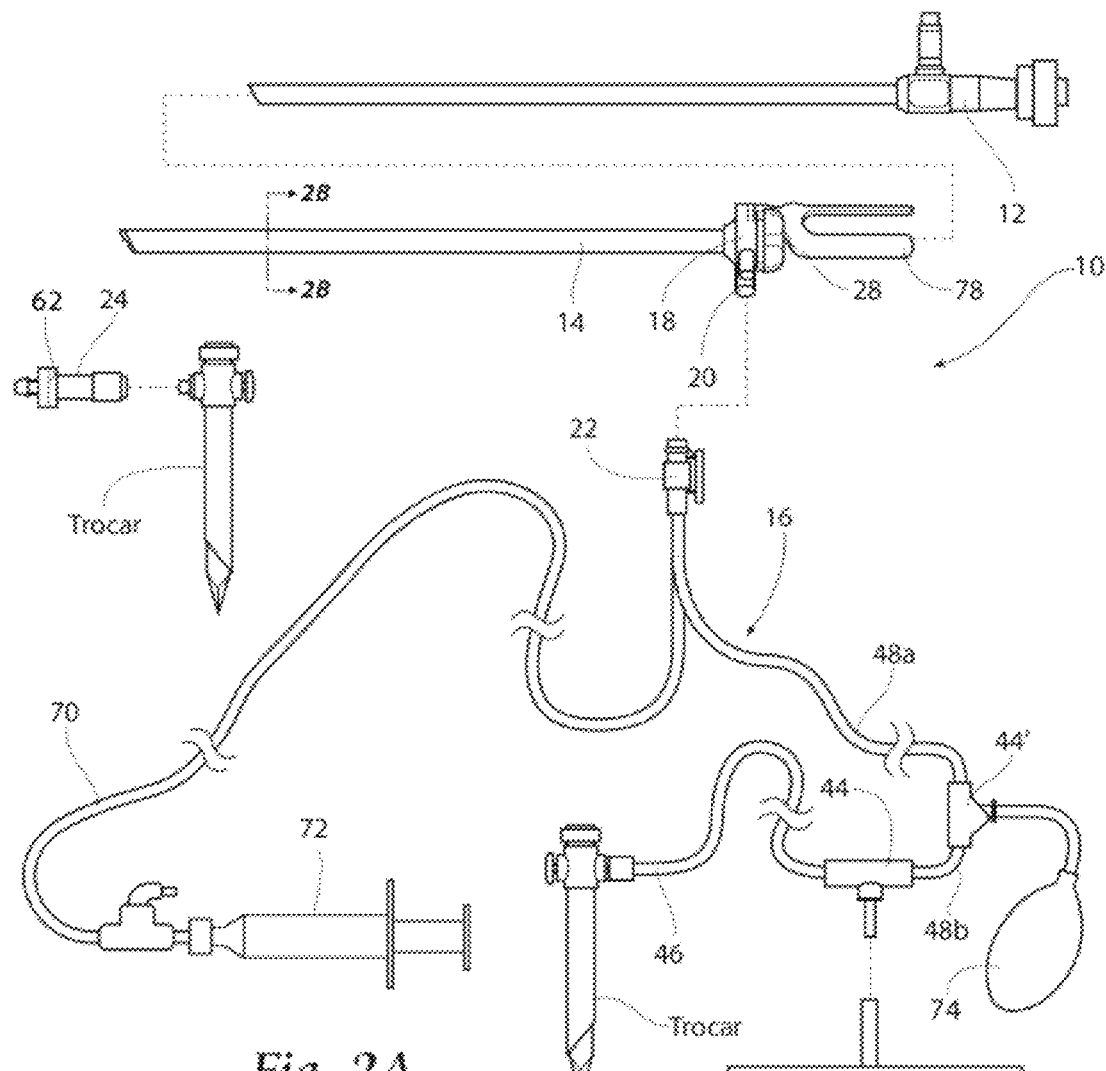
FIG. 2A is a somewhat schematic, exploded view of a view optimizing assembly for use with a laparoscope having an angled shaft tip.

FIGS. 1A/1B and FIG. 2A/2B show embodiments of a view optimizing assembly 10 for use in association with a state of the art laparoscope 12. In FIGS. 1A/1B, the laparoscope 12 possesses at 0° (blunt) shaft tip In FIGS. 2A/2B, the laparoscope possess an angle shaft tip (e.g., a 30° shaft tip or 45° shaft tip). The components of the view optimizing assembly 10 may be made from plastic materials (extruded and/or molded), but other suitable materials, such as metal or a composite material, or combinations thereof could be used.

As will be described in greater detail, the view optimizing assembly 10 facilitates intra-operative defogging, surgical debris deflection, and cleaning of a laparoscope lens during minimally invasive surgery, while also maintaining visualization of the surgical site. The view optimizing assembly 10 is intended to be a single-use, disposable laparoscopic accessory. The view optimizing assembly 10 is desirably a sterile accessory for immediate set up and use on a sterile operating field.

Figure 2B:
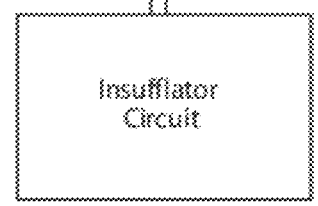
FIG. 2B is a section view of the sheath, showing internal fluid flow lumens, taken generally along line 2B-2B in FIG. 2A.

As shown in FIGS. 1A and 2A, the view optimizing assembly 10 comprises a multi-lumen sheath assembly 14, which mounts over the shaft of the laparoscope 12. In the illustrated embodiment, there are five lumens 34; 36; 38; 40; and 42 in the sheath 14, as shown in section views FIGS. 1B and 2B.

The end of the sheath 14 is sized and configured to match the size and configuration of the corresponding laparoscope 12, having a blunt tip in FIG. 1A and an angled tip in FIG. 2A.

The assembly 10 includes a tubing set 16 to connect the sheath 14 to an existing carbon dioxide ($CO_2$) insufflation circuit and to a source of a flushing liquid 72. Further details of the flushing liquid will be described later. A manifold 18 on the proximal end of the sheath 14 includes a quick exchange coupling 20 that mates with a quick exchange coupler 22 on the tubing set 16, to quickly couple the tubing set 16 in fluid communication with the interior lumens 34; 36; 38; 40; and 42 of the sheath 14. Further details of the quick exchange coupling 20 and the quick exchange coupler 22 are shown in FIGS. 15A-20, and will be described later.

In use, the view optimizing assembly 10 makes possible the practice of a surgical method for maintaining clear visualization of the surgical site without removing the laparoscope 12 from the abdominal cavity for the purpose of cleaning or de-fogging its lens. Furthermore, the view optimizing assembly 10 also makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly 10 integrates with the existing suite of minimally invasive instrumentation. It does not interfere with the surgical set-up, and it requires minimal change in the process or practice of a surgical operating room (OR) team.

The view optimization assembly 10 desirably comes packaged for use in sterile peel away pouches. The pouches contain the components of the view optimization assembly 10 as shown in FIGS. 1A and 2A, including the sheath 14, the manifold 18 that is assembled to the sheath 14 and that includes a quick exchange coupling 20; the tubing set 16 which includes a quick exchange coupler 22 that mates with the quick exchange coupling 20 on the manifold 18; and (optionally) a vent device 24. The vent device 24 (see FIGS. 1A and 2A) comprises a tube with an inline membrane 62 that restricts air flow through the tube. A proximal end of the tube is sized and configured to couple to a stopcock valve of a conventional trocar. In use, the vent device 24 provides a controlled leak of $CO_2$ from the operating cavity.

B. The Sheath

As shown in FIGS. 1A and 2A, the sheath 14 is sized and configured to receive a laparoscope 12 having a prescribed tip angle, length, and diameter. The distal end of the sheath 14 includes a stop 26 (best shown in FIGS. 24 and 27). The stop 26 prevents advancement of the laparoscope 12 beyond the distal end of the sheath 14. The stop 26 assures that the lens at the distal end of the laparoscope 12 rests in a desired, generally coterminous alignment with the distal end of the sheath 14.

Figure 15A:
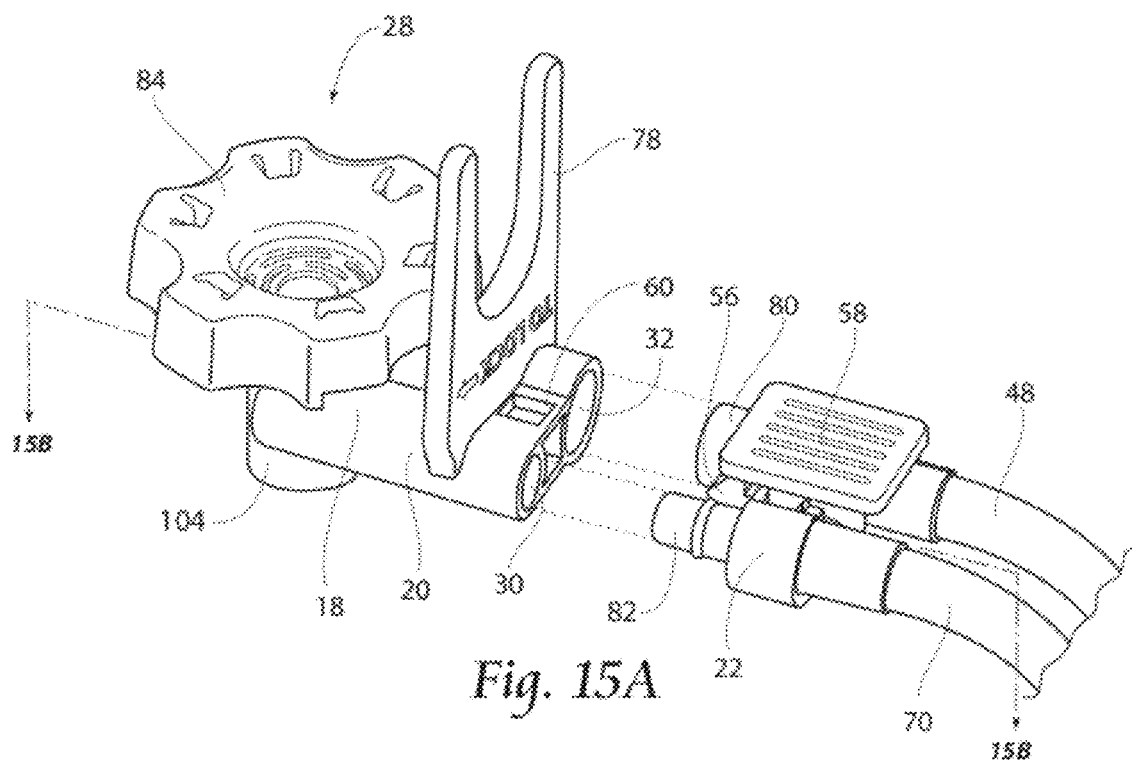
FIG. 15A is an enlarged perspective view of a manifold that the view optimizing assembly shown in FIG. 1A or FIG. 2A incorporates, including a quick exchange coupling, and a quick exchange coupler that the tubing set shown in FIG. 1A or FIG. 2A incorporates, the coupling and the coupler being disconnected.

The sheath 14 also includes a locking collar 28 at its proximal end, to frictionally engage the laparoscope 12 and resist axial withdrawal of the laparoscope 12 from the sheath 14. Further details of the locking collar 28 are shown in FIGS. 15A/15B, 16A/B, and 21A-22D and will be described later.

In use, it is expected that the laparoscope 12 will be inserted into the sheath 14 by a scrub nurse during set-up for the operation. The assembled laparoscopic and sheath 14 will then be handed as a unit to personnel at the operating room (OR) table at the desired time. The laparoscope 12 is then connected in a conventional way by personnel at the OR table in conventional fashion to a light cable (which directs light to illuminate the operative field) and the camera cable (which takes the image from the scope and displays it on monitors in the OR). The sheath 14 is sized and configured not to interfere with this normal set-up of the laparoscope 12.

In use, the assembled laparoscopic and sheath 14 are placed as a unit through a trocar into the body cavity (e.g., the abdominal cavity), for viewing the surgical procedure as it is performed.

C. The Manifold

Figure 15B:
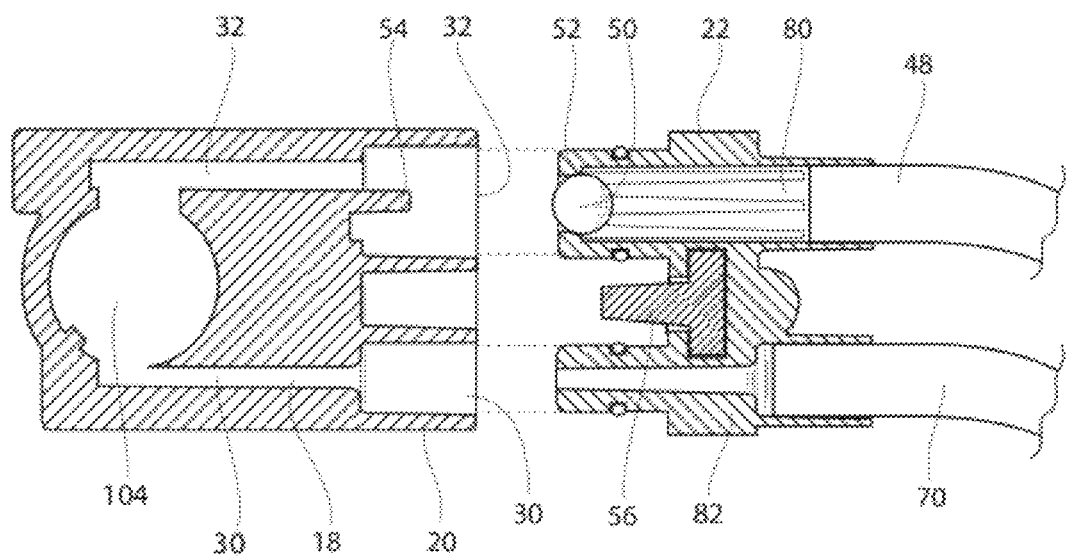
FIG. 15B is a sectional view taken generally along line 15B-15B in FIG. 15A, showing a one way check valve that is normally closed.

The manifold 18 at the proximal end of the sheath 14 communicates with the multiple lumens 34; 36; 38; 40; and 42 formed within the wall of the sheath 14. As shown in FIGS. 15A-15B, the manifold 18 includes the quick exchange coupling 20 with inlet passages 30 and 32 opening into a manifold junction 104. FIGS. 15A-15B show inlet passage 30 opening into the manifold junction 104. FIGS. 15A-15B further show inlet passage 32 opening into the manifold junction 104 generally across from the inlet passage 30. In use, the inlet passage 30 is intended to convey a sterile flushing liquid to the manifold junction 104. In use, the inlet passage 32 is intended to convey pressurized $CO_2$ to the manifold junction 104.

As FIGS. 17-20 show, the manifold junction 104 and the proximal end of the sheath 14 are keyed to fit the proximal end of the sheath 14 in a prescribed rotational orientation within the manifold junction 104. Manifold key K1 in FIG. 17 receives sheath key K2 in FIG. 20. The proximal ends of the lumens 34; 36; 38; 40; and 42 are configured to register with the inlet passages 30 and 32 in a specific way when the proximal end of the sheath 14 is key-fitted in the manifold junction 104 in the prescribed rotational orientation. The specific registration couples the inlet passage 30 in flow communication only with the interior lumen 38 of the sheath, and thereby dedicates the interior lumen 38 to the conveyance of sterile flushing liquid to the distal end of the sheath 14 (see FIG. 23). The specific registration couples the inlet passage 32 in concurrent flow communication with all the remaining interior lumens 34; 36; 40; and 42, and thereby dedicates the interior lumens 34; 36; 40; and 42 to the conveyance of pressurized $CO_2$ to the distal end of the sheath (see FIG. 23).

D. The Tubing Set

As previously described, the tubing set 16 includes a quick exchange coupler 22 that mates with the quick exchange coupling 20 on the manifold 18 (see FIGS. 15A/B and 16A/B). The tubing set 16 includes lengths of flexible medical grade tubing with individual end couplers (best shown in FIGS. 1A and 2A) that connect to an existing $CO_2$ insufflation circuit and, if desired, a source 72 of sterile flushing liquid (e.g. a saline or sterile water, preferably with a "surface active agent") on the sterile operating field (e.g., a bag or a syringe). The tubing set 16 includes a T-connector 44 for coupling the insufflation $CO_2$ circuit directly to the trocar. A first branch of tubing 46 (see FIG. 2A) may be used to connect the T-connector 44 to the trocar. The T-connector also provides for the $CO_2$ output of the insufflation circuit to a second branch 48 coupled to the quick exchange coupler 22. Either arrangement shown in FIG. 1A or 2A may be used to connect the insufflation circuit to the trocar. A second T-connector 44' that is in-line with the second branch 48 provides connection to a squeeze-pump 74 that will allow the delivery of a burst of air into the tubing set 16, as discussed below. As with the trocar, the squeeze pump 74 may be directly connected to the T-connector 44' (FIG. 1A) or connected with the use of tubing (FIG. 2A).

The second branch 48 diverts a small portion of the $CO_2$ output (e.g., 20% or less) to a male coupler 80 on the quick exchange coupler 22 that is sized and configured to mate within the inlet passage 32 of the quick exchange coupling 20.

Figure 3A:
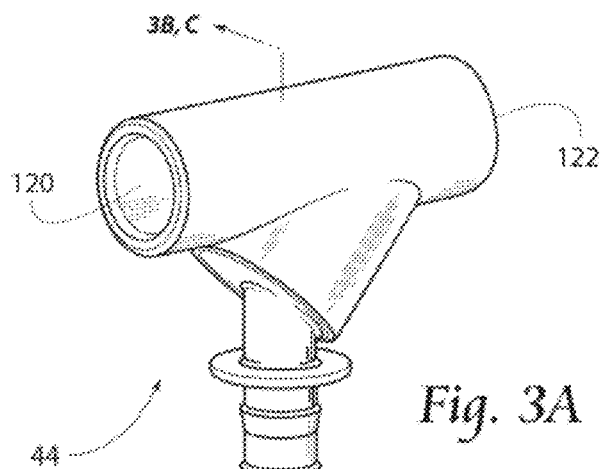
FIG. 3A is perspective view of a T-connector for connecting a squeeze pump to the tubing set of the present invention, with squeeze pump capable of providing a burst of $CO_2$ to the system.
Figure 3B:
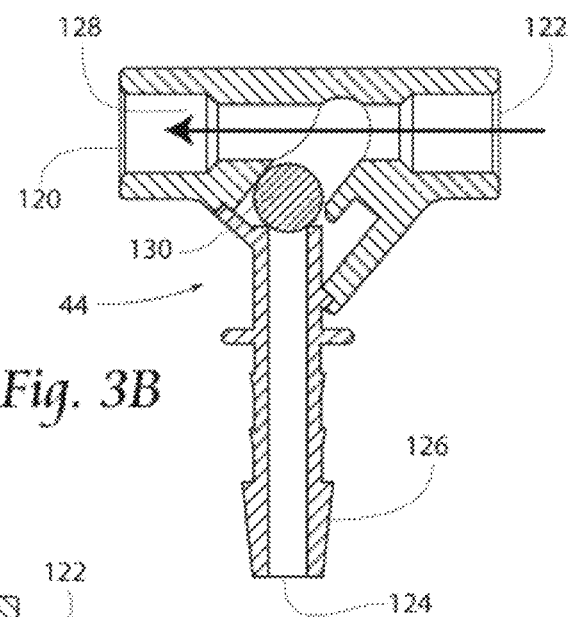
FIG. 3B is a cross-sectional view of the connector of FIG. 3A taken along line 3B-3B of FIG. 3A, showing the normal flow of $CO_2$ from an insufflator through the T-connector.
Figure 3C:
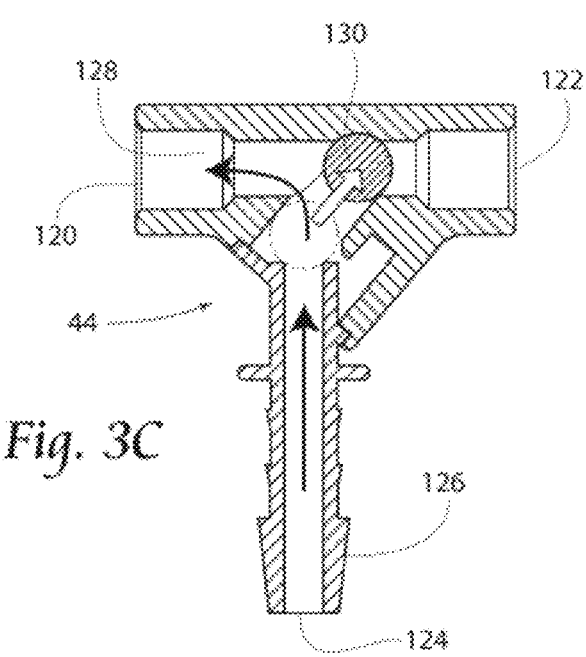
FIG. 3C is cross-sectional view of the connector of FIG. 3A, taken along line 3C-3C of FIG. 3A, showing the squeeze pump being activated and providing a burst of $CO_2$ to the system.

The T-connector 44' is shown in more detail in FIGS. 3A-3C. The T-connector 44' forms a valve 128 that has a first end 120 to be connected to the first portion 48a of the second branch 48 and a second end 122 for connecting to a second portion 48b of the second branch 48 of the tubing 16 (see FIG. 1A). The bottom 124 of the T-connector 44' provides a fitting 126 for connection to the squeeze-pump 74, as shown in FIGS. 1A and 2A.

As is demonstrated in FIG. 3B, when the insufflator is in normal use, $CO_2$ will flow through the T-connector 44'. A ball 130 is located within the valve 128, with the pressure of the flowing $CO_2$ maintaining the ball 130 within the bottom section of the valve 128.

As is discussed further below, FIG. 3C demonstrates the use of the squeeze-pump 74 to deliver a burst of $CO_2$ to the lens of the laparoscope. Pressure is applied to the squeeze pump 74, thereby moving the ball 130 up into the second end 122 of the T-connector 44', thereby momentarily stopping the flow of $CO_2$ from the insufflator circuit and providing the burst of $CO_2$.

Figure 4A:
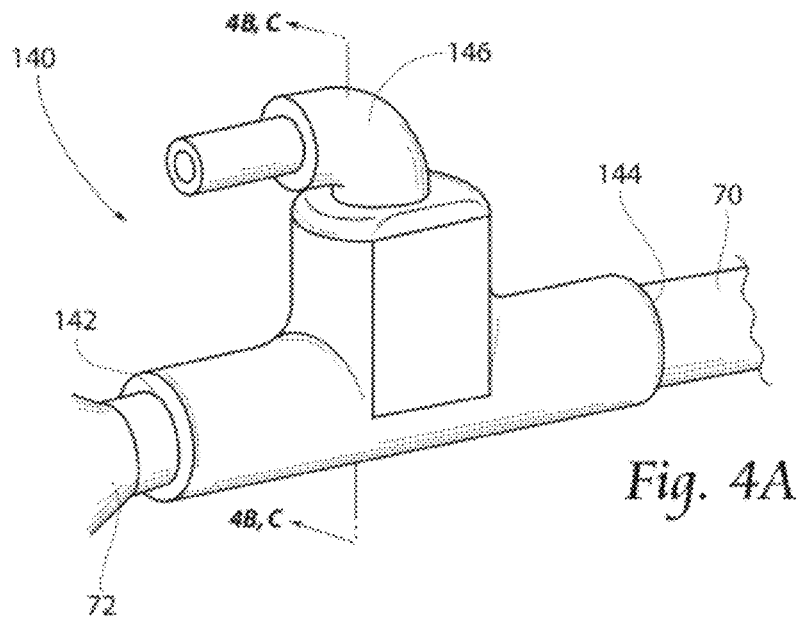
FIG. 4A is a perspective view of a pressure valve used in connection with a sterile fluid source used with the present invention.
Figure 4B:
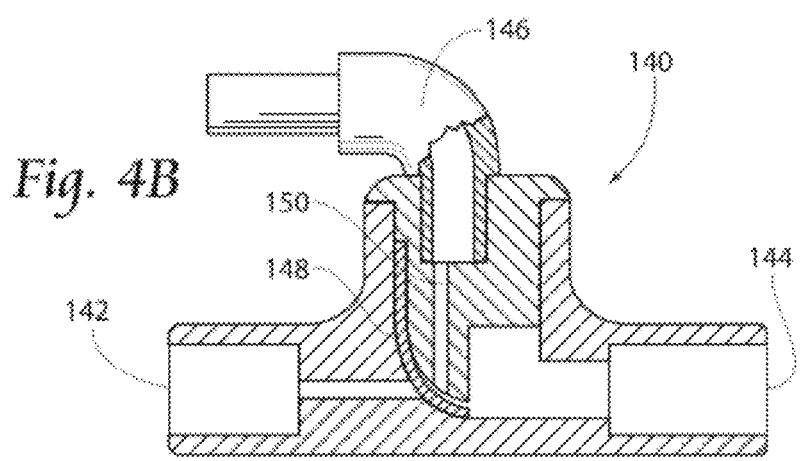
FIG. 4B is a cross-sectional view of the pressure valve of FIG. 4A taken along the line 4B-4B of FIG. 4A, with the pressure valve being shown in a normal operating position.
Figure 4C:
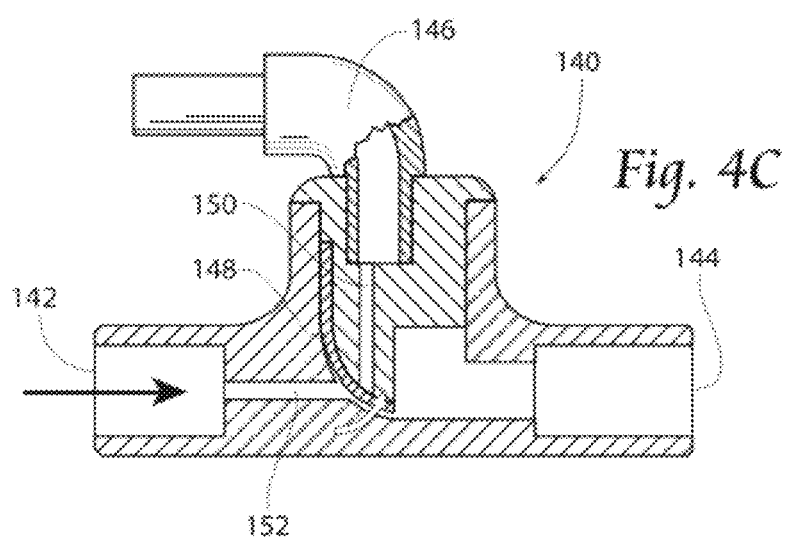
FIG. 4C is a cross-sectional view of the pressure valve of FIG. 4A taken along line 4C-4C of FIG. 4A, showing sterile fluid being introduced into the tubing set of the present invention.

FIGS. 4A-4C show a pressure release valve 140 (also shown in FIGS. 1A/2A) that works in connection with the source of sterile fluid 72 (see FIGS. 1A/2A). The pressure release valve has a first end 142 that allows connection to the sterile fluid source 72 and a second end 144 for connection to the tubing 70 (see FIGS. 1A/2A). A pressure exit 146 is located on the pressure release valve 140, which allows venting of excess gas when the assembly is in use. The pressure exit 146 is shown as being an attached drain structure, but it is understood that such a structure is not necessary for the exit 146 to work properly as part of the release valve 140.

As shown in FIG. 4B, a flapper valve 148 is located within the pressure release valve 140 and is normally positioned in a manner that closes the first end 142 of the valve 140, thereby preventing back flow of gas into the sterile fluid source 72. As will be discussed further below, gas will be allowed to move outwardly through the valve 140 and exit through the pressure exit 146.

When it is desired to inject fluid into the tubing set 16, the sterile fluid source, i.e. the syringe, 72 will be pushed forward to dispel fluid, as shown in FIG. 4C. The pressure being applied will move the flapper valve 148 from the position in FIG. 4B to the position in FIG. 4C. The fluid from the syringe 72 will be delivered to the optimizing assembly, while the pressure exit 146 will momentarily be closed off. The flapper valve 148 also acts as a seal in the valve. It has been determined that the flapper valve 148 must be flexible enough so that it will be able to move from the position in FIG. 4B to the position in FIG. 4C, while maintaining a positive seal when in the position shown in FIG. 4C. That is, the pressure normally used during a laparoscopic procedure, e.g. 15 mm Hg, will provide a force that will maintain the flapper valve 148 in the position in 4B, and the flapper valve 148 should be manufactured from a material that will allow such a positive seal. An example of a preferred material is a silicone rubber, having a durometer=20 shore A.

Use of the squeeze pump 74 and the pressure release valve 140 contribute to the ability of the present optimizing assembly 10 to be operated without the necessity of the laparoscope 12 being removed during a procedure. Such a process was not realized with prior art assemblies, as the interaction between the use of air and cleaning fluids and their interaction was not properly appreciated with the prior art. FIGS. 5-14 demonstrate the procedure carried out according to the present invention.

Figure 5:
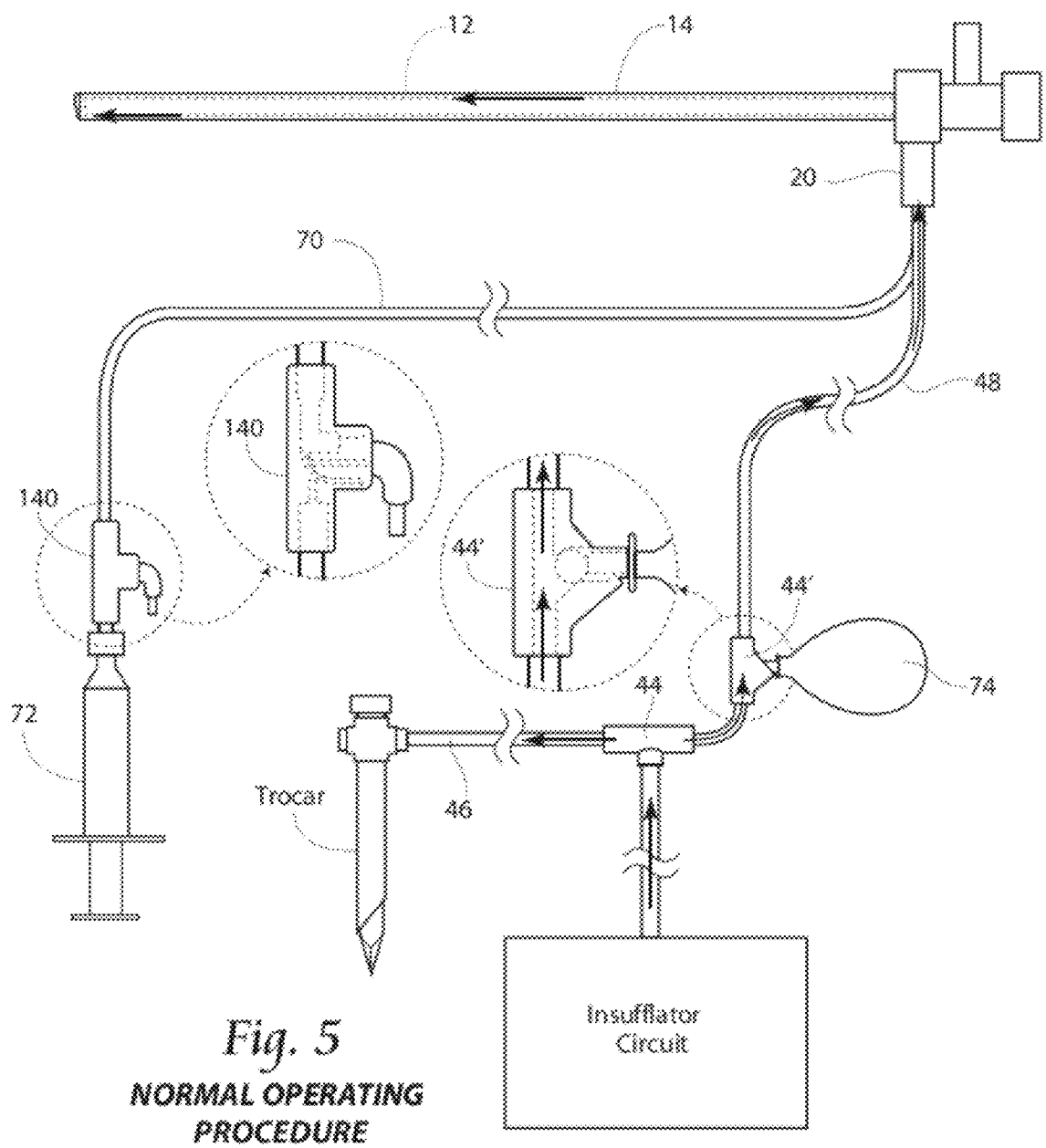
FIG. 5 is a somewhat schematic view of the optimizing assembly, demonstrating normal operation of the assembly with the delivery of $CO_2$ to the assembly.
Figure 6:
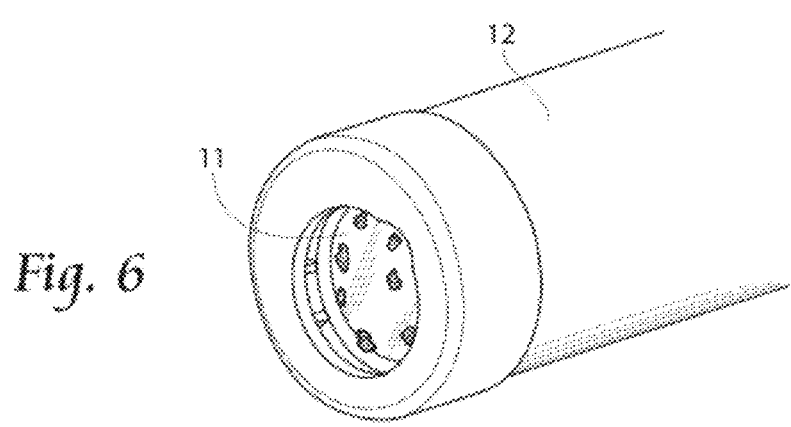
FIG. 6 is a perspective view of the lens of a laparoscope during normal operation procedure, with the lens having surgical debris on the lens.

FIG. 5 shows the optimizing assembly of the present invention during normal operating procedure during a laparoscopic procedure. The insufflator circuit delivers $CO_2$ to the system, with the T-connector 44' being in the position shown in FIG. 3B and the pressure release valve 140 being in the position shown in FIG. 4B. Eventually, sheeting of surgical debris will build up on the lens 11 of the laparoscope, as shown in FIG. 6.

Figure 7:
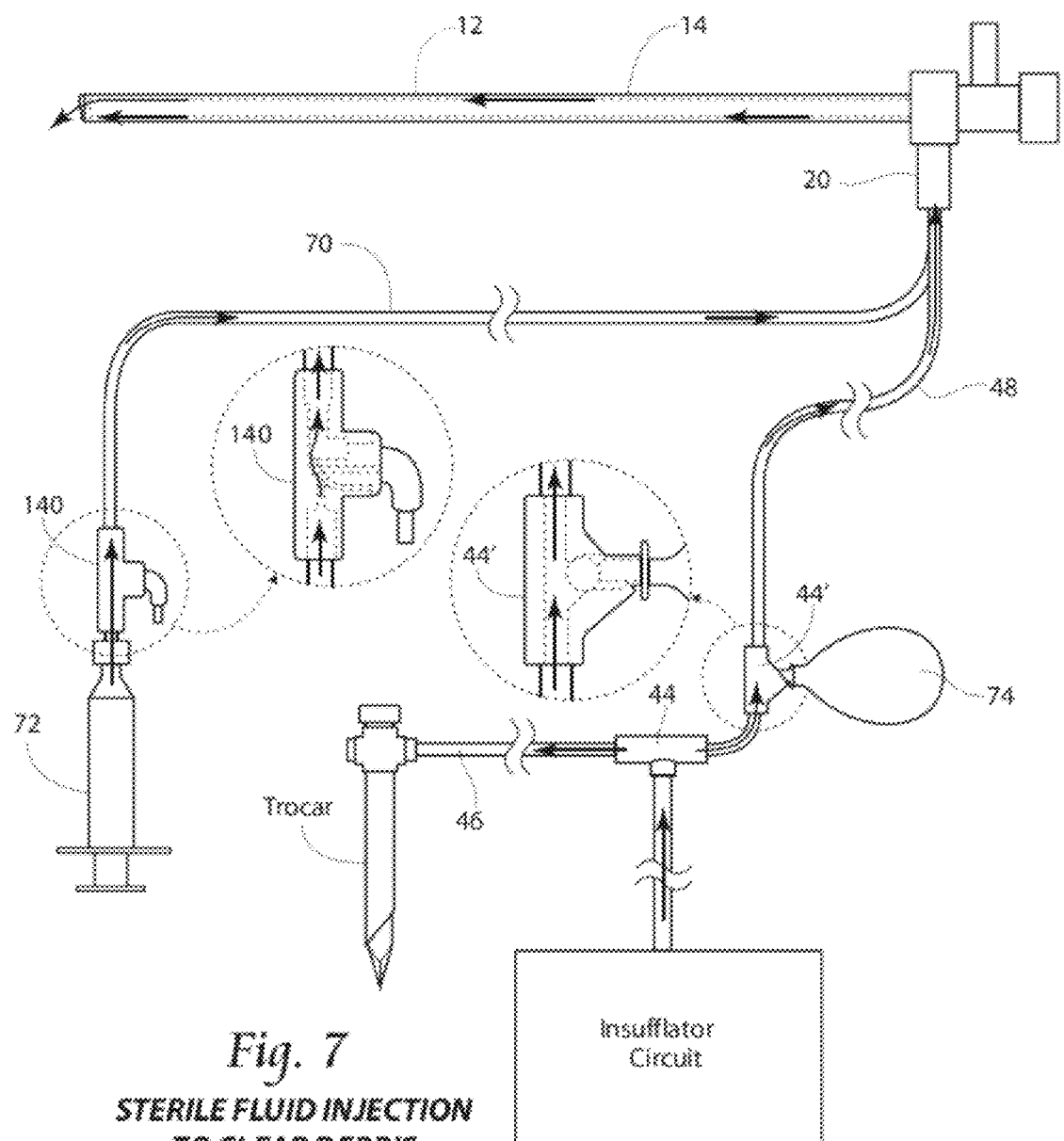
FIG. 7 is a somewhat schematic view of the optimizing assembly, demonstrating the delivery of a cleaning fluid to the assembly.
Figure 8:
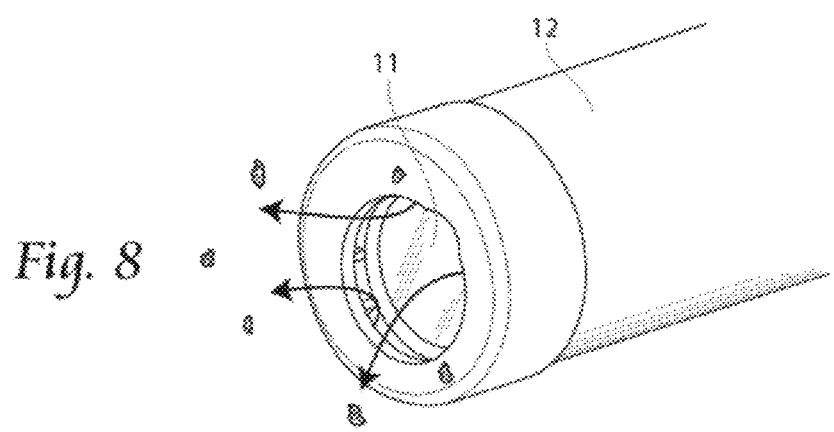
FIG. 8 is a perspective view of the lens of FIG. 6, with the cleaning fluid removing the surgical debris from the lens.

To clear the debris off of the lens 11, sterile fluid is delivered to the lens, as shown in FIG. 7. The T-connector 44' remains in position as shown in FIG. 3B, while the pressure release valve is in the position shown in FIG. 4C. As demonstrated in FIG. 8, the release of sterile fluid removes the surgical debris from the lens 11

Figure 9:
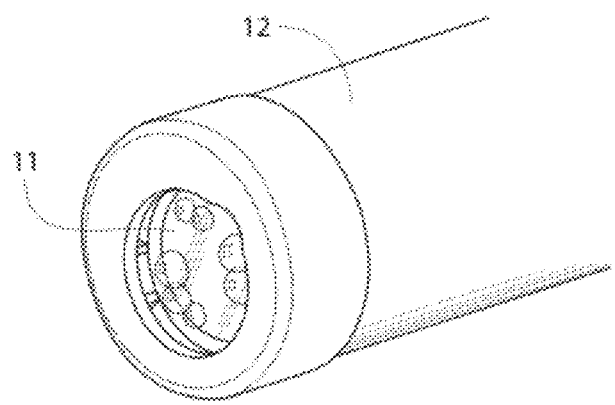
FIG. 9 is a perspective view of the lens of FIG. 8, demonstrating the formation of bubbles being formed on the lens during use of the optimizing assembly.
Figure 10:
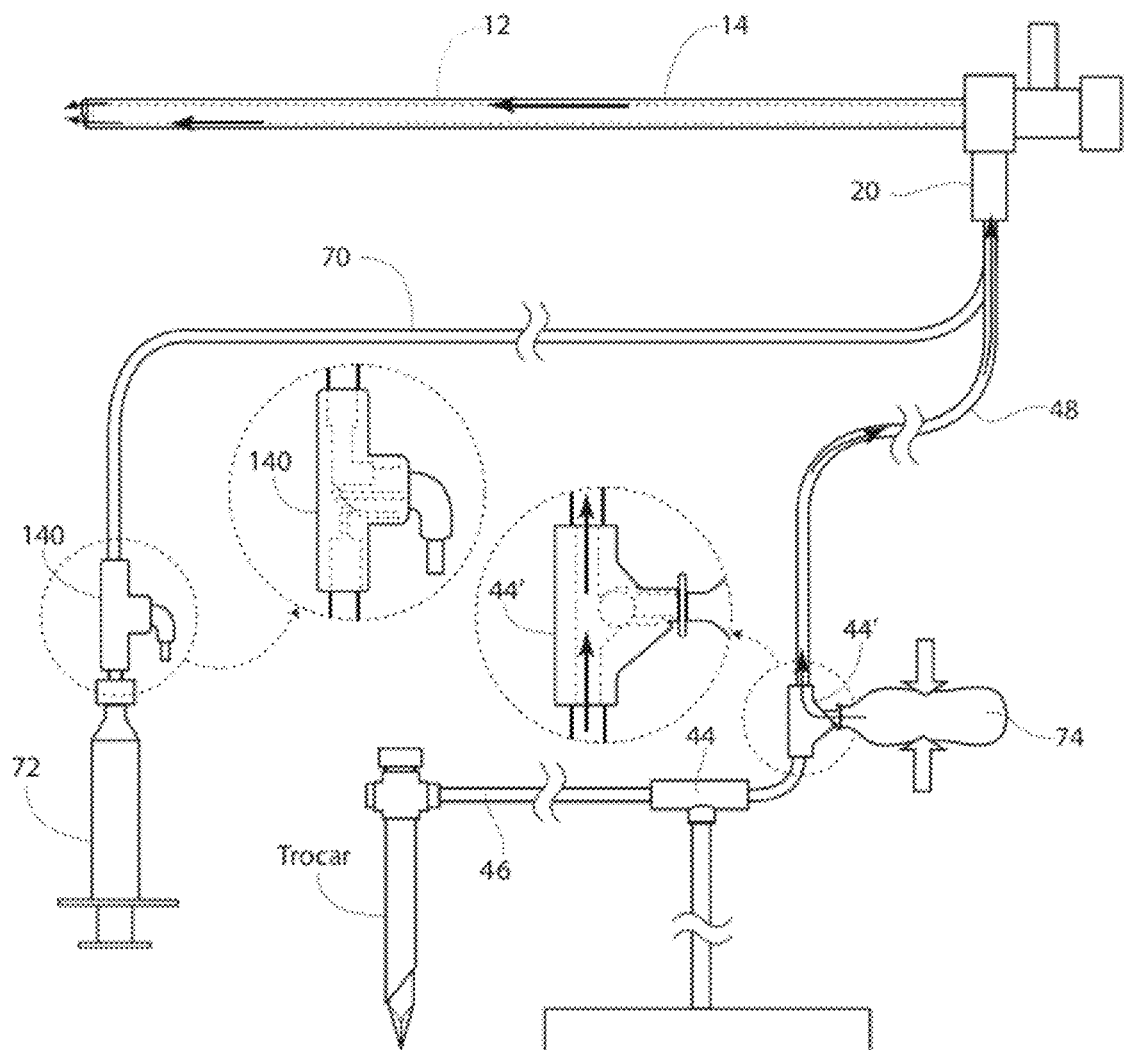
FIG. 10 is a somewhat schematic view of the optimizing assembly, demonstrating the delivery of a burst of $CO_2$.
Figure 11:
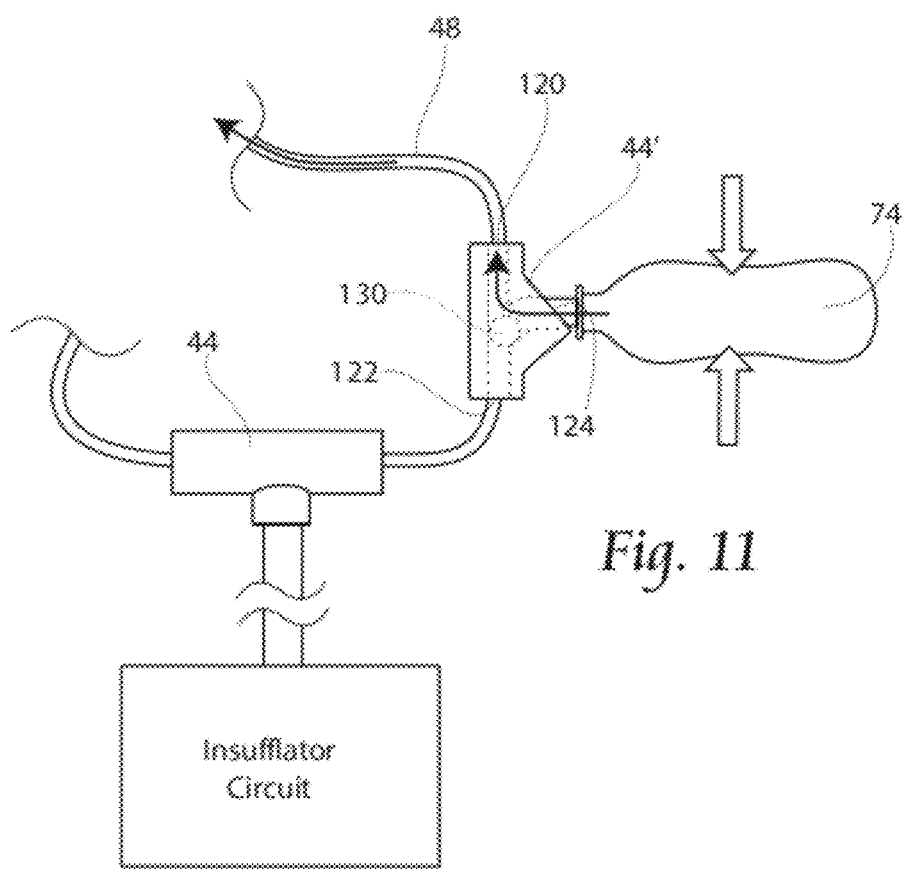
FIG. 11 is another somewhat schematic view of the optimizing assembly demonstrating the delivery of a burst of $CO_2$.

As shown in FIG. 9, during normal operating procedures, the flow of $CO_2$ may eventually cause the formation of bubbles on the surface of the laparoscope lens, which can inhibit the view through the lens. FIGS. 10 and 11 shows the squeeze pump 74 being compressed, thereby moving the T-connector 44' to the position shown in FIG. 3C. The compression squeeze pump 74 allows a burst of air to travel towards the laparoscope and across the lens.

Figure 12:
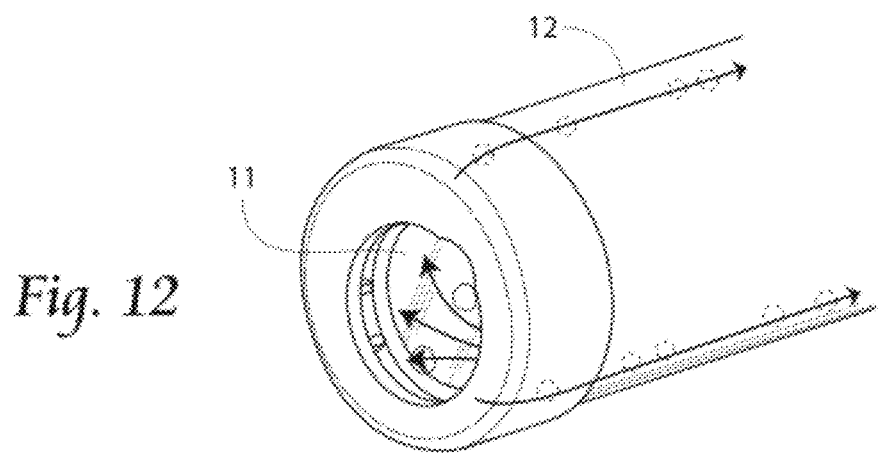
FIG. 12 is a perspective view of the lens of FIG. 9, showing the removal of bubbles from the lens after the application of a burst of $CO_2$.
Figure 13:
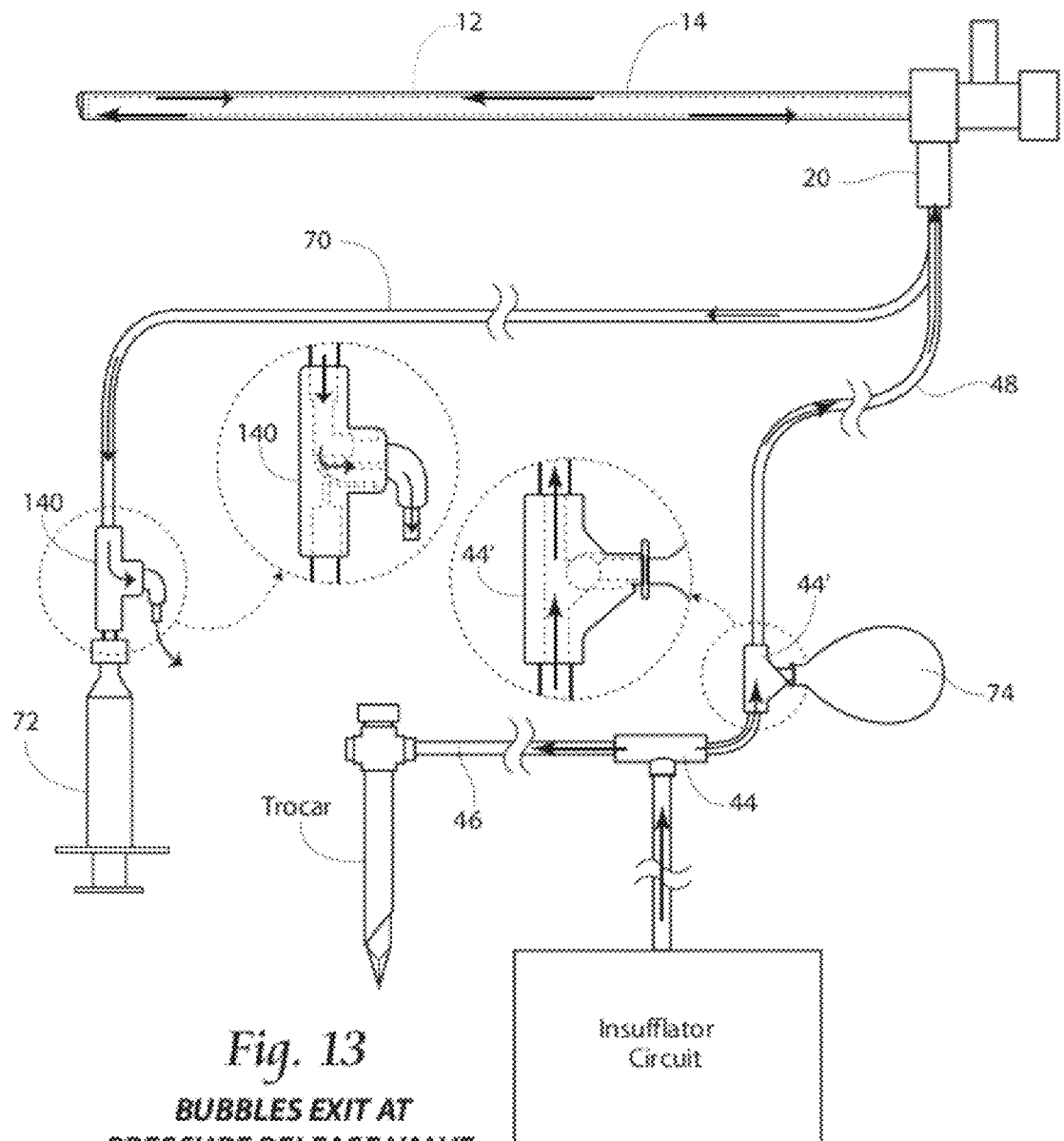
FIG. 13 is a somewhat schematic view of the optimizing assembly demonstrating the removal of bubbles from the optimizing assembly.
Figure 14:
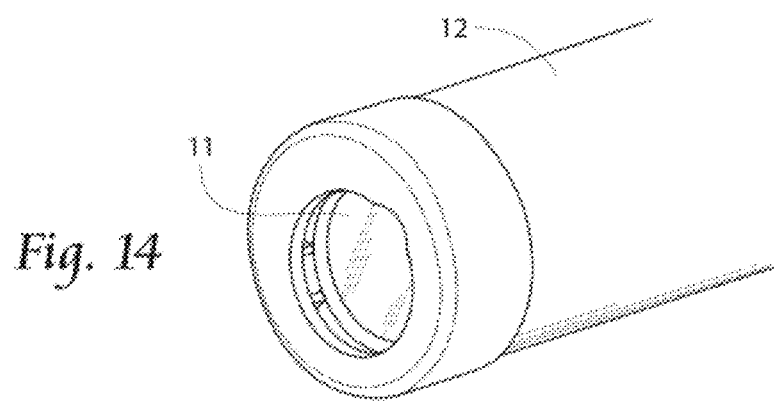
FIG. 14 shows a cleared laparoscope lens after a burst of air has been sent to the laparoscope lens.

As is depicted in FIG. 12, the lens of FIG. 9 has been cleared of the bubbles, thereby allowing a procedure to continue without having to remove and clean the lens. The cleared bubbles will exit out of the system, through the pressure release valve 140, as shown in FIG. 13. The result is a lens 11, free of both debris and bubbles as shown in FIG. 14.

The above described process was not previously realized in the prior art. Particularly it was not realized that the use of the $CO_2$ burst in combination with a cleansing liquid was used to provide a clear lens as shown in FIG. 14 without necessitating removal of the laparoscope during a procedure.

Referring now to FIGS. 15A and 15B, the male coupler 80 of the quick exchange coupler 22 includes a one way check valve 50 that communicates with the second branch 48 of the tubing set 16. In the illustrated embodiment, the check valve 50 comprises a ball valve. Insufflation pressure normally presses the ball valve 50 against a ball valve seat 52 (as shown in FIG. 15B). A projection 54 in the inlet passage 32 of the manifold 18 displaces the ball valve 50 from the valve seat 52 when the male coupler 80 of the quick exchange coupler 22 mates within inlet passage 32 of the quick exchange coupling 20 on the manifold 18 (as shown in FIG. 16B). Unseating the ball valve 50 opens flow communication through the check valve 50 of the $CO_2$ into the inlet passage 32 and thus via the manifold junction 104 into all the lumens 34; 36; 40; and 42 of the sheath 14. In the absence of coupling the male coupler 80 of the quick exchange coupler 22 to the inlet passage 32 on the manifold 18, the check valve 50 remains closed, normally blocking flow of $CO_2$ through the second branch 48.

Thus, the tubing set 16 accommodates the set-up of the supply of the entire $CO_2$ output to an insufflation trocar through the tubing set 16, separate and independent of the connection of the tubing set 16 to the manifold 18 of the sheath 14.

The tubing set 16 also includes, connected to the quick exchange coupler 22, a length of tubing 70 sized and configured for connection to a source 72 of sterile liquid, such as saline or sterile water (as shown in FIGS. 1A and 2A).

As shown in FIGS. 1A/2A, the sterile liquid tubing 70 desirably includes an in-line pumping device 72. The in-line pumping device 72 is sized and configured to be operated on demand by a person at the OR table to convey bursts of sterile liquid through the tubing 70. The in-line pumping device 72 and source can be integrated and comprise, e.g., a 20 cc syringe filled with sterile liquid and connected by a tubing luer-lock on the saline tubing. Alternatively, the in-line pumping device 72 and source can be separate and comprise, e.g., a bag of sterile liquid, a spike connection on the saline tubing of the tubing set 16 to open communication with the bag in conventional fashion.

Preferably, the sterile liquid includes in solution a "surface-active agent" that stabilizes mixtures of oil and water (e.g., fat) by reducing the surface tension at the interface between the oil and water molecules.

As FIGS. 15A/15B and 16A/16B show, the tubing 70 conveys the sterile liquid to a male coupler 82 on the quick exchange coupler 22 that is sized and configured to mate within the inlet passage 30 of the quick exchange coupling 20. Mating the male coupler 82 and inlet passage 30 establishes flow communication for the sterile liquid into the inlet passage 30 and thus via the manifold junction 104 into the lumens 38 of the sheath 14.

Figure 16A:
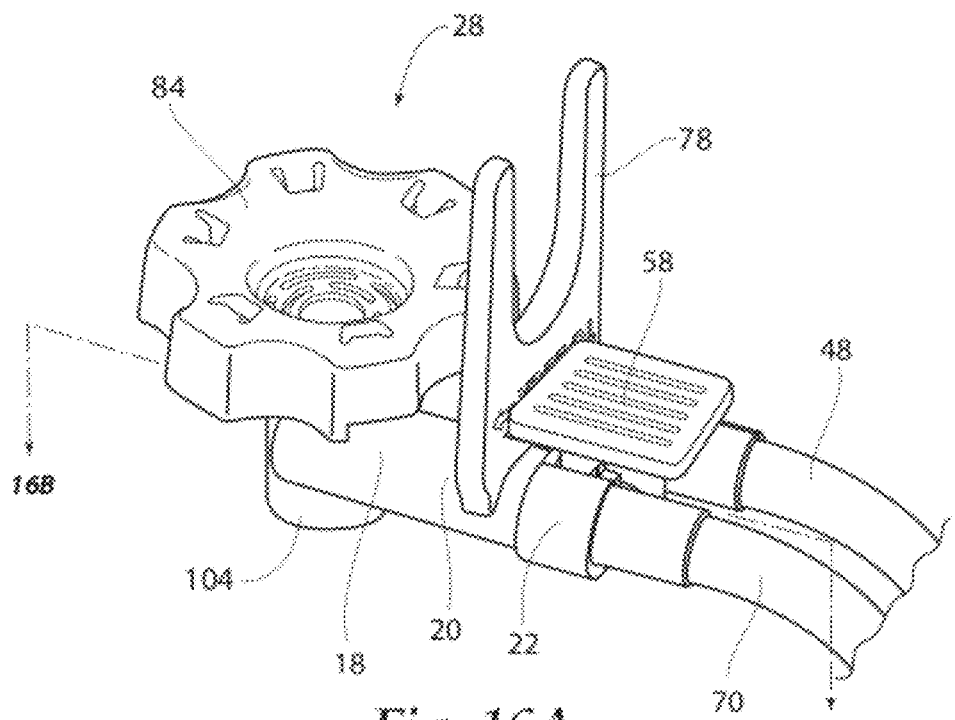
FIG. 16A is an enlarged perspective view of the manifold including a quick exchange coupling and the quick exchange coupler of the tubing set, as shown in FIG. 15A, but now connected.
Figure 16B:
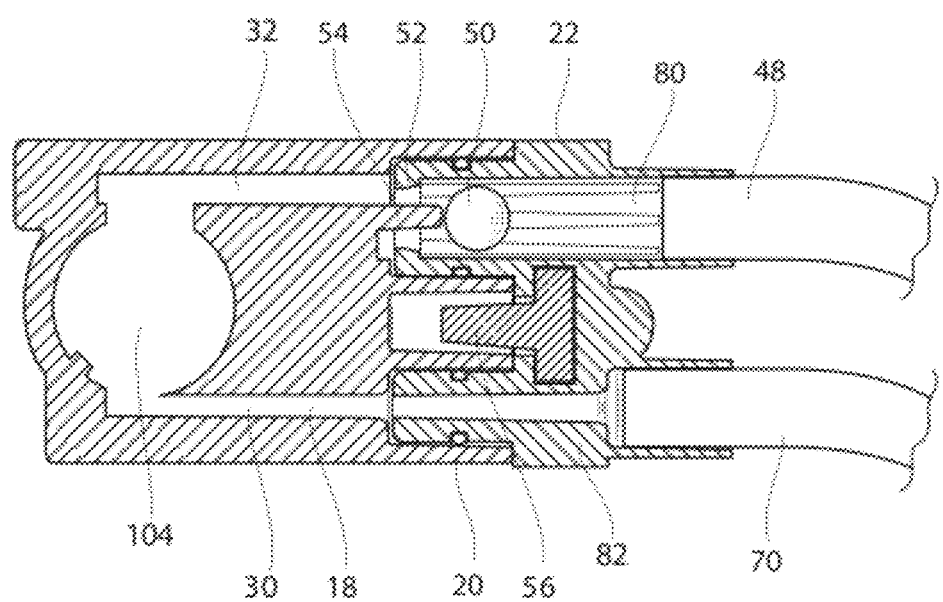
FIG. 16B is a sectional view taken generally along line 16B-16B in FIG. 16A, showing the one way check valve that is opened by the connection of the quick exchange coupling and connectors.
Figure 17:
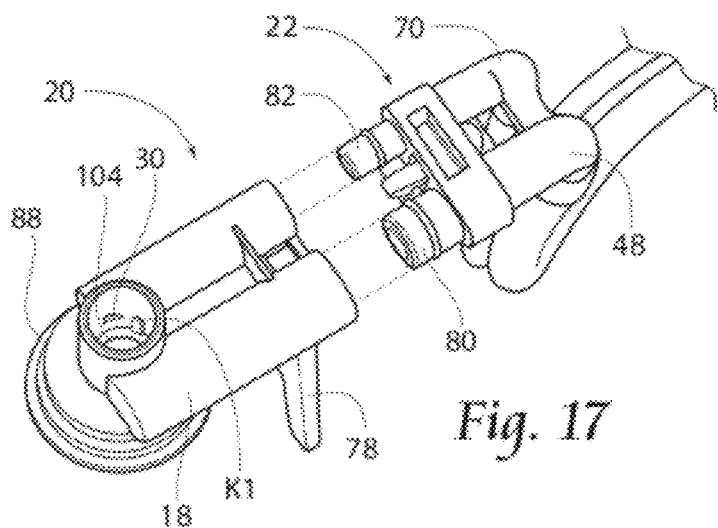
FIGS. 17 and 18 are different perspective views of the manifold showing how passages in the manifold communicate with a manifold junction within the manifold.

As FIGS. 15A and 16A further show, a latch 56 carried on a spring-biased button 58 on the quick exchange coupler 22 "clicks" into a detent 60 on the quick exchange coupling 20 on the manifold 18 to reliably lock the coupler 22 and coupling 20 together for use, opening the check valve to flow $CO_2$ through the second branch 48 and establishing flow communication for the sterile liquid through the tubing 70 (shown in FIGS. 16A/16B). Depressing the button 58 allows the quick exchange coupler 22 and coupling 20 to be separated, and the check valve 50 will close in response to insufflation pressure in the second branch 48 (as shown in FIGS. 15A/15B).

Connection of the quick exchange coupling 20 on the manifold 18 to the quick exchange coupler 22 on the tubing set 16 is intended to occur at the OR table in the normal course, after the laparoscope 12 is connected to the light cable and the camera cable. Upon coupling, the one way check valve 50 is opened, and the manifold 18 directs the small portion of $CO_2$ from the $CO_2$ insufflation circuit. Upon coupling, the manifold 18 also establishes flow communication for the sterile liquid. Disconnection of the of the quick exchange coupling 20 on the manifold 18 to the quick exchange coupler 22 on the tubing set 16 is also intended to occur at the OR table in the normal course, after a removal and/or exchange of a laparoscope 12.

E. The Locking Collar

The laparoscope 12 can be inserted down into the sheath 14. The sheath 14 is sized and configured so that the laparoscope 12 will slide smoothly through the sheath 14. Insertion continues until the lens and distal rim of the laparoscope 12 seat against the stop 26 at the distal end of the sheath 14. The laparoscope 12 will "bottom out" inside the sheath 14 against the stop 26, assuring correct axial alignment of the lens with a deflector assembly 64 located at the distal end of the sheath 14, as will be described in greater detail later.

If the laparoscope 12 is angled (as shown in FIG. 2A), the corresponding angled sheath assembly will also include an alignment fork guide 78. The alignment fork guide is also shown in FIGS. 15A and 16A. The light post of the scope seats within the alignment fork guide 78, therefore assuring correct rotational alignment between the angled lens and the deflector assembly 64.

Once the laparoscope 12 is fully inserted into and aligned with the sheath 14, a member of the OR set-up team can rotate the locking collar 28 on the manifold 18 in the desired direction, e.g., clockwise (see FIGS. 21 and 17B), until a firm stop is felt tactilely (e.g., after approximately one-third (⅓) of a turn). Registration of an alignment mark on the locking collar 28 and an alignment mark on the manifold 18 can additionally serve to visually confirm that the laparoscope 12 is secured against axial movement relative to the sheath 14.

Figure 22B:
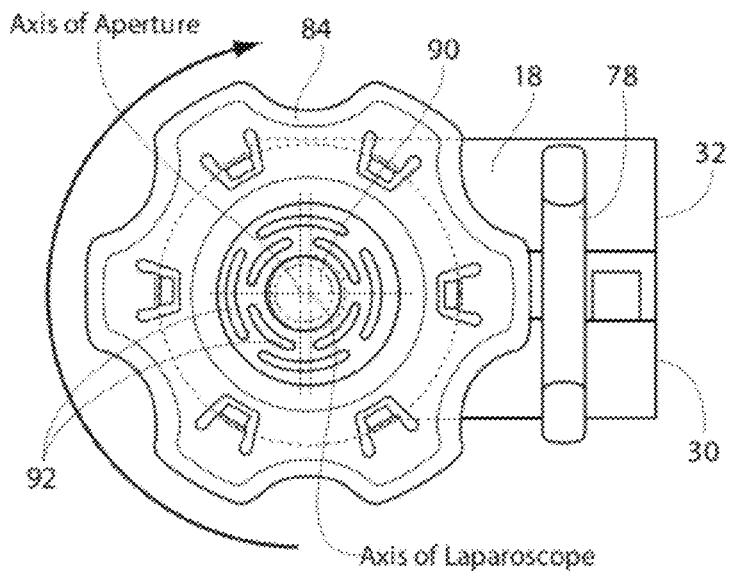

In the illustrated embodiment (see FIG. 21A), the locking collar 28 comprises a grip handle 84 mounted for rotation by a collet interacting with tabs 86 engaging an annular flange 88 on the manifold 18. An eccentric aperture 90 is formed in the grip handle 84. In a first rotational position (shown in FIG. 22A), the axis of the aperture 90 aligns with the axis of the sheath 14, allowing free passage of the laparoscope 12 through the aperture 90 into the sheath 14. In a second rotational position (shown in FIG. 22B), the axis of the eccentric aperture 90 shifts out of alignment with the axis of the sheath 14, and an interior edge of the aperture 90 frictionally contacts an exterior wall of the laparoscope 12. A pattern of cut-outs 92 formed about the periphery of the eccentric aperture 90 provide a spring resilience to the frictional contact. The frictional contact secures the laparoscope 12 against axial movement relative to the sheath 14.

In an alternative arrangement shown in FIG. 21B, the locking collar 28 on the manifold 18 can comprise a conventional collet mechanism 87. The collet mechanism 87 includes an inner sleeve 89 that, in response to rotation of the grip handle 84, radially closes to form a collar around the shaft of the laparoscope 12, to exert a clamping force that secures the laparoscope 12 against axial movement relative to the sheath 14. A seal 91 is also used to insure proper fluid flow through the assembly.

Figure 22C:
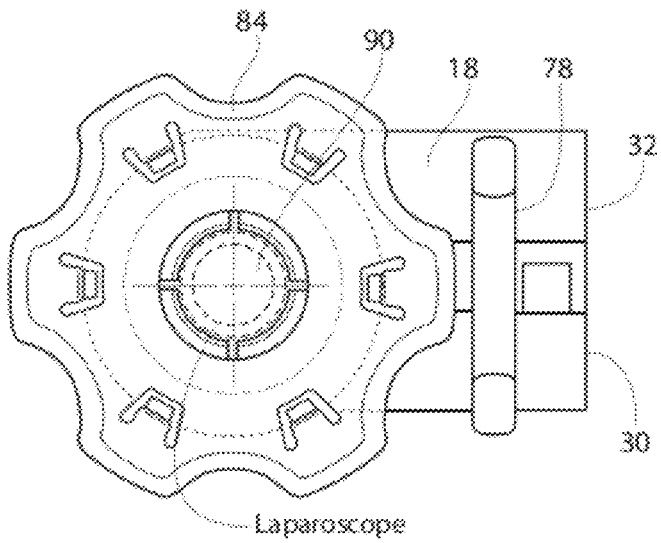
FIGS. 22C and 22D are views of an alternative embodiment of the locking collar comprising a collet mechanism when opened (FIG. 22C) and closed (FIG. 22D)
Figure 22D:
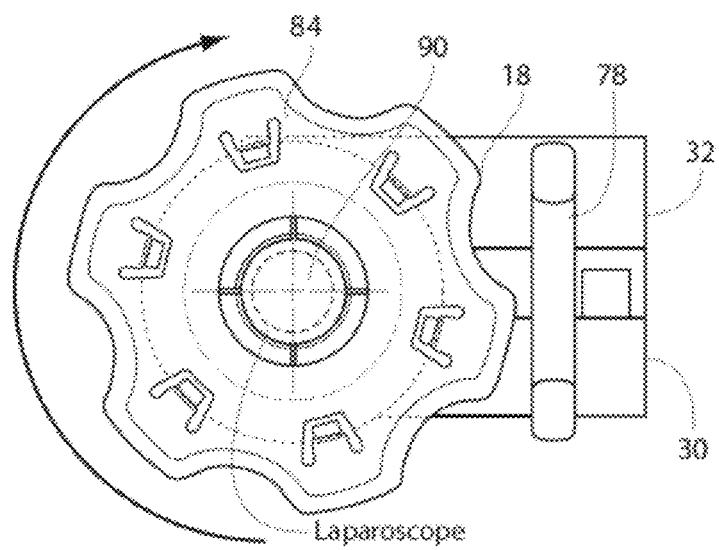

As shown in FIGS. 22D and 22C, rotating the grip handle 84 of FIG. 21B in one direction (see FIG. 22D) closes the collar to squeeze the sleeve against the laparoscope 14, resulting in high static friction. Rotating the grip handle 84 in an opposite direction (see FIG. 22C) opens the collar, to release the laparoscope 14.

F. The Deflector Assembly

1. CO2

Figure 23:
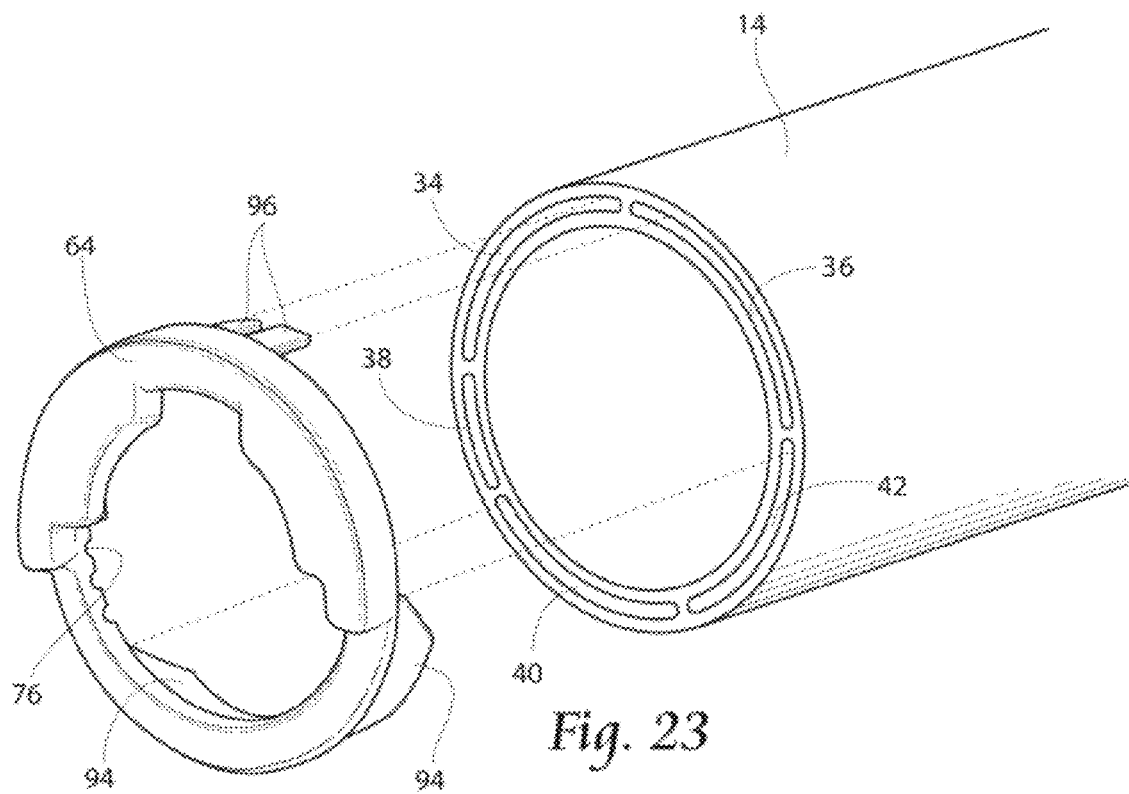
FIG. 23 is an enlarged, exploded view of the deflector assembly for use with a laparoscope having a 0° shaft tip.
Figure 24:
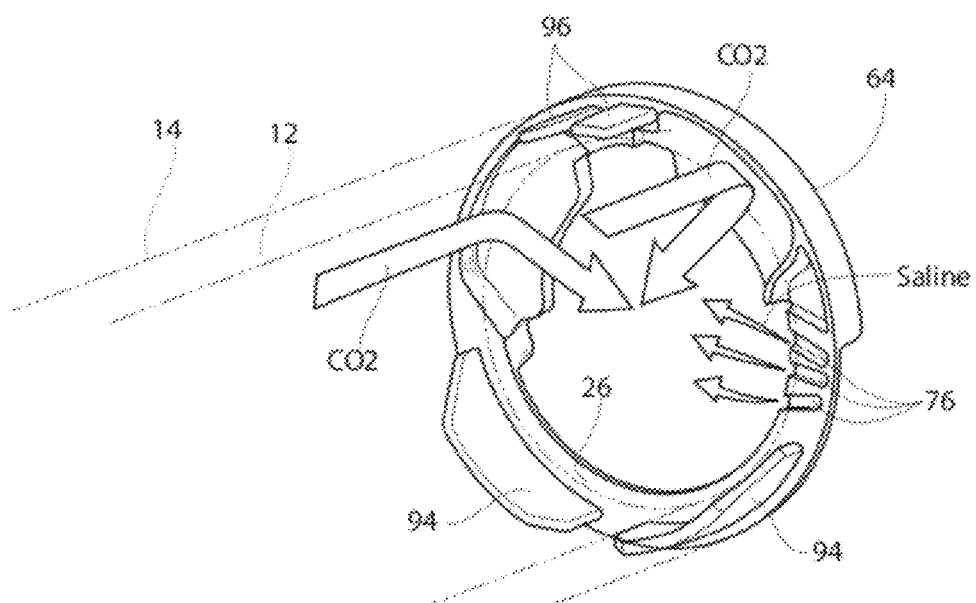
FIG. 24 is a perspective view of the deflector assembly shown in FIG. 16 when viewed from the inside of the sheath.
Figure 26:
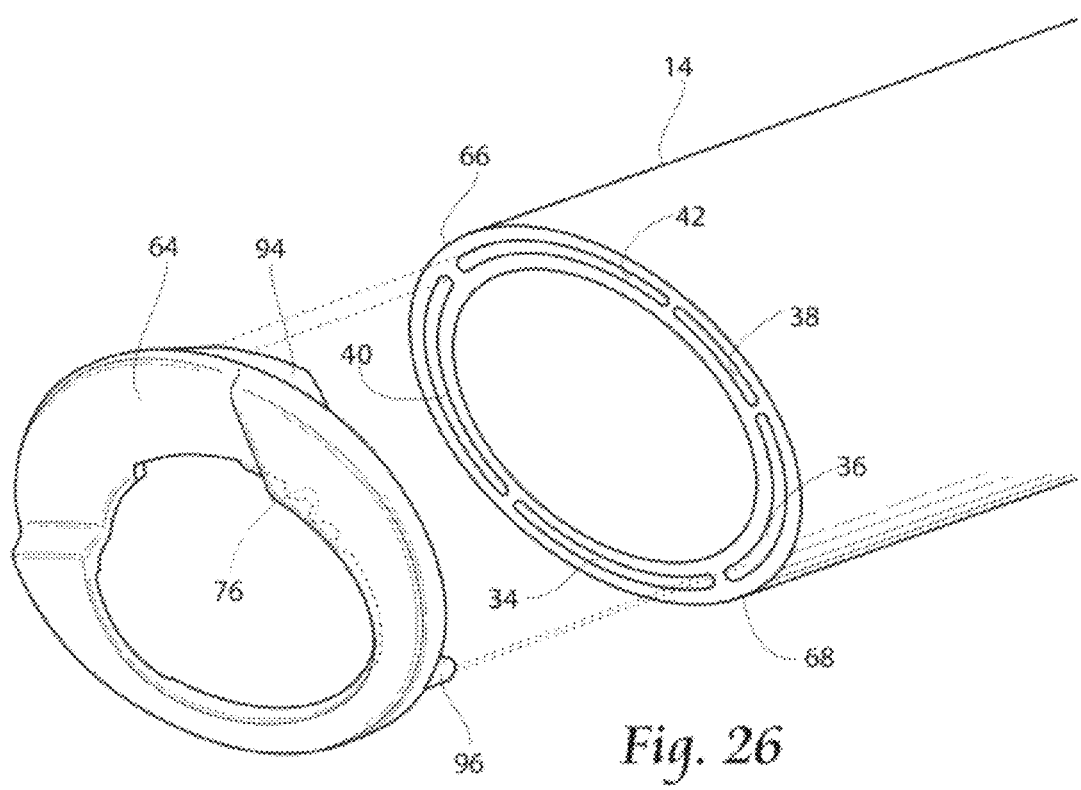
FIG. 26 is an enlarged, exploded view of the deflector assembly for use with a laparoscope having an angled shaft tip.
Figure 27:
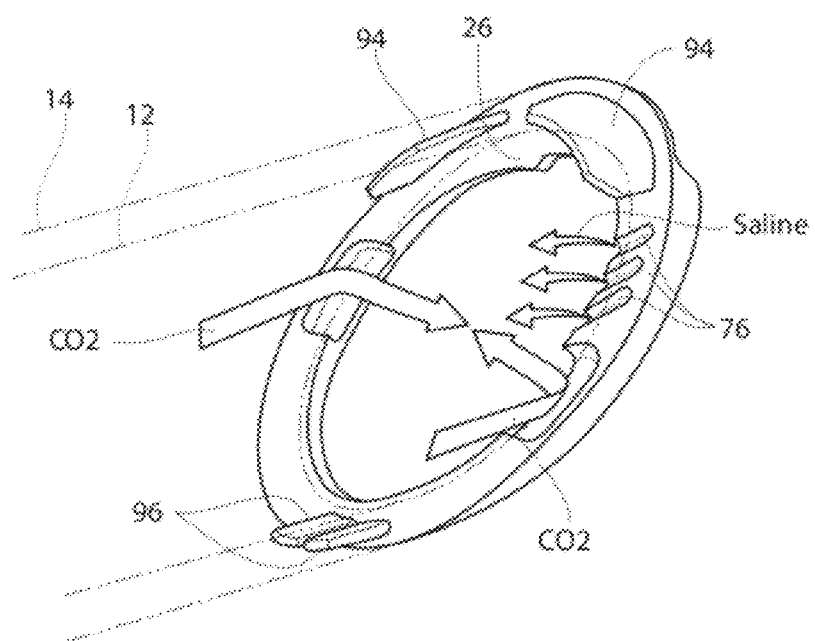
FIG. 27 is a perspective view of the deflector assembly shown in FIG. 26 when viewed from the inside of the sheath.

The sheath 14 includes at its distal end a deflector assembly 64 (see FIGS. 23 and 24 for a blunt shaft tip and FIGS. 26 and 27 for an angled shaft tip). The deflector assembly 64 projects a predetermined distance beyond the distal end of the sheath 14, and thus also a predetermined distance beyond the lens at the distal end of the laparoscope 12 (see also FIG. 29).

In the embodiments shown in FIGS. 23/24 and 26/27, the deflector assembly 64 is secured to the distal end of the sheath 14 by mounting tabs 94 that insert into the lumens 40 and 42, thereby blocking $CO_2$ flow through these lumens 40 and 42 at the distal end of the sheath. The deflector assembly 64 also includes smaller mounting tabs 96 that fit into and partially occupy the lumens 34 and 36, so that the deflector assembly 64 communicates with the lumens 34 and 36 in the sheath 14.

The deflector assembly 64 is sized and configured to direct the portion of the $CO_2$ that is conveyed by the sheath 14 through the lumens 34 and 36 in a prescribed flow path and flow velocity across the laparoscopic lens, as will be described in greater detail later. The flow path and flow velocity of the $CO_2$ across the laparoscopic lens prevents fogging and also desirably serves to prevent entrainment or deposition of particles (moisture and particulate matter) onto the lens, as well as deflect smoke and surgical debris away from the laparoscopic lens during surgery, preventing entrainment.

2. Physical, Pneumatic, and Optical Characteristics of the Deflector Assembly

The size and configuration of the deflector assembly 64 are defined and constrained by several, sometime overlapping considerations including (i) prescribed physical characteristics, which are imposed due to the need to access the operating environment in as minimally invasive of a manner as possible and to be compatible with state of the art laparoscopes and other laparoscopic surgical instruments and techniques; (ii) prescribed pneumatic characteristics, which are imposed due to the need to create a particular flow path and flow velocity of $CO_2$ across the laparoscopic lens; and (iii) prescribed optical characteristics, which are imposed due to the need to prevent interference with the field of view and the visualization of the operating field by the laparoscope 12.

3. Physical Characteristics

The size and configuration requirements for minimally invasive access compatible with state of the art laparoscopic instrumentation and techniques are paramount. These requirements impose constraints upon the minimum inside diameter of the sheath 14 as well as the maximum outside diameter of the sheath 14. Because state of the art laparoscopes are provided with different shaft diameters, lengths, and lens configurations, the sheath dimensions and configuration change for compatibility with them. The view optimizing assembly 10 actually includes a family of sheath 14/manifold 18 assemblies differently sized and configured to accommodate different classes of laparoscopes, to make possible compatibility with the families of state of the art laparoscopes that are in use.

For example, state of the art laparoscopes include 10 mm laparoscopes, 5 mm laparoscopes, and, within these sizes, 0° shaft tips, 30° shaft tips, and 45° shaft tips. Further, within these classes of laparoscopes, manufacturing tolerances typically vary from scope to scope, as well as from manufacturer to manufacturer. A given sheath 14/manifold 18 assembly for a given laparoscope class (e.g., 10 mm or 5 mm) desirably takes these typical manufacturing and manufacturer variances into account, and is desirably sized and configured to fit the largest scope variance encountered within a given laparoscope class.

To maximize the fluid flow lumen area within the sheath 14, the minimum inside diameter of a given sheath 14 must closely conform to the maximum outside diameter of the shaft of the particular state of the art laparoscope 12 selected for use, which the sheath 14 must accommodate in a smooth, sliding fit. Further, a gap between the outside diameter of the laparoscope shaft and the inside diameter of the sheath 14 must be minimized to avoid the transport and leakage of blood and fluids from the operating field. Still further, minimizing the gap also assures that the laparoscope 12 self-centers in the sheath 14, thereby assuring faithful and accurate visualization through the laparoscope lens.

For example, for a typical laparoscope 12 in the 10 mm class, which measures 0.392 inch, the inside diameter of the sheath 14 is manufactured to 0.405 inch, providing a gap thickness of 0.0064 inch. For a 5 mm laparoscope 12 in the 5 mm class, which measures 0.196 inch, the inside diameter of the sheath 14 is manufactured to 0.218 inch, providing gap thickness of 0.011 inch.

The maximum outside diameter of the sheath 14 for minimally invasive access must take into account the minimum inside diameter of the trocar, which the maximum outside diameter cannot exceed. That is, the outside diameter of the sheath 14 is constrained by the inside diameter of the trocar. For example, in one embodiment a 5 mm sheath 14 is used in combination with a trocar having a 7 mm inside diameter and a 10 mm sheath 14 is used in combination with a trocar having a 12 mm diameter.

For example, for a typical 10 mm trocar that measures 0.509 inch, the outside diameter of the sheath 14 is manufactured to 0.486 inch, providing a gap thickness of 0.0115 inch. For a typical 5 mm trocar that measures 0.324 inch, the outside diameter of the sheath 14 is manufactured to 0.300 inch, providing a gap thickness of 0.012 inch.

Figure 29:
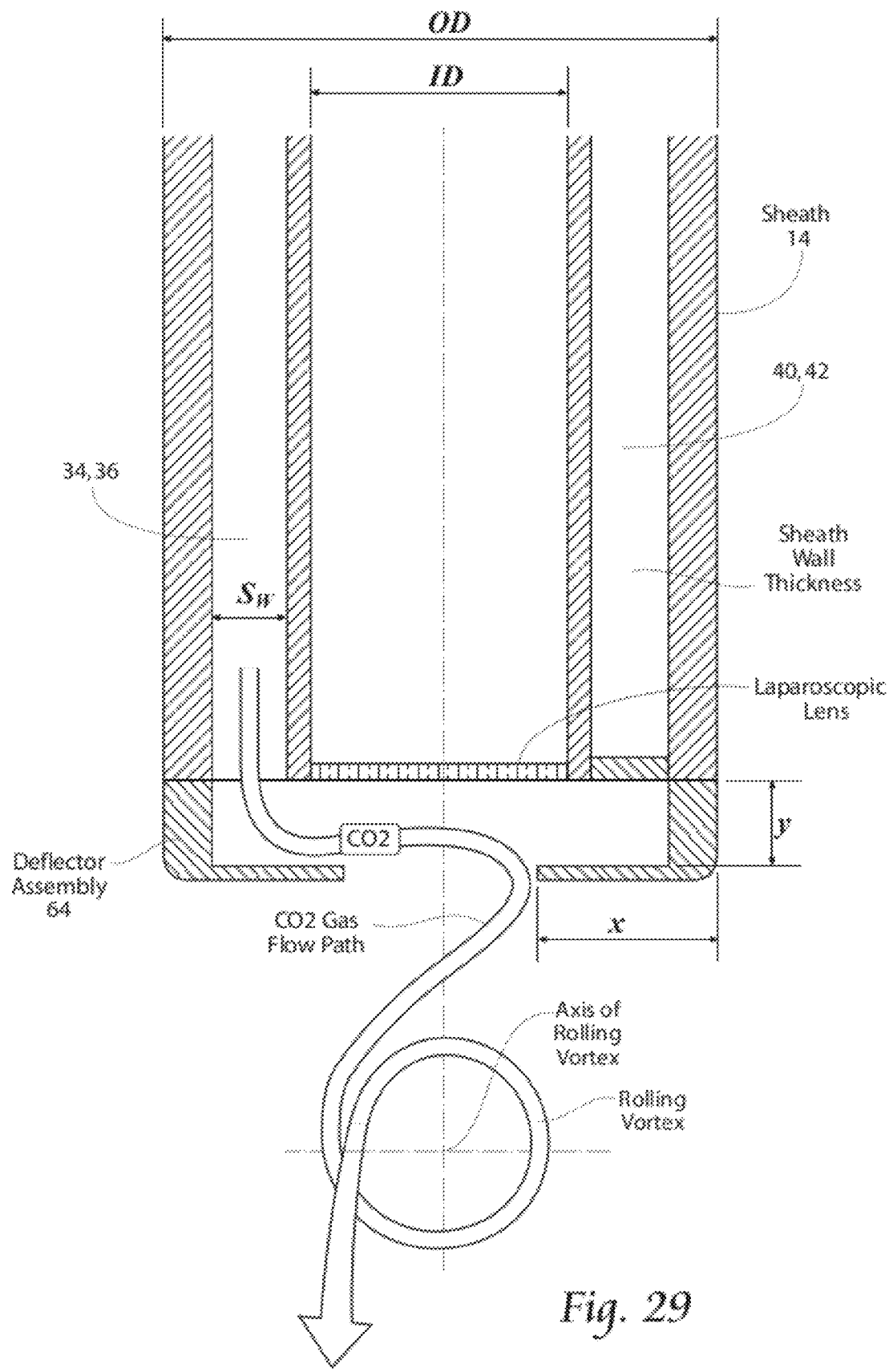
FIG. 29 is a schematic view of the critical physical, pneumatic, and optical characteristics of the deflector assembly shown in FIG. 23.

It is desirable, given the particular size and configuration constraints of the laparoscopic instrumentation and techniques used, to maximize the outside diameter to the extent possible. This is because, together, the inside and outside diameters of the sheath 14 define the wall thickness for the sheath $S_w$, as FIG. 29 shows. The wall thickness $S_w$, together with the length of the sheath 14, in turn, defines the maximum area available for the transport of the $CO_2$ and fluids by the sheath 14. The area of the fluid flow lumen or lumens dedicated to the supply of $CO_2$, in turn, defines the maximum flow rate of the $CO_2$ directed by the deflector assembly 64. The flow rate should be sufficient at a minimum, given the output of the insufflator selected for use, to supply $CO_2$ across the lens of the laparoscope 12 sufficient to prevent fogging.

Also affecting the effectiveness of the $CO_2$ to defog the lens is the water content of the $CO_2$. Given the same flow rate, the less water that is present in the $CO_2$, the greater is the defogging capacity of the assembly. Further, the flow rate desirable should also be sufficient to deflect smoke and surgical debris away from the viewing field of the laparoscopic lens during surgery, so that the $CO_2$ directed by the deflector assembly 64 both defogs and deflects debris.

Medical grade $CO_2$ for use with conventional insufflators is typically 99% pure, that is, no more than 1% of the gas is other than $CO_2$, and such medical grade $CO_2$ generally has a maximum moisture content of 25 parts per million by volume. Typically, a state of the art insufflator circuit delivers $CO_2$ at a max flow rate of about 20 liters per minute. Typically, the insufflator circuit will sense pressure in the circuit and cycle off when the sensed pressure is at or above 15 mmHg and cycle on when the sensed pressure is below 15 mmHg. Generally during procedures, the flow rate ranges between 3LPM-7LPM for approximately 50% of a procedure, with the remainder of the time of the procedure having the flow rate adjusted up or down, as determined by measuring the peritoneal pressure.

Given the above sheath dimensions, and given the supply of typical medical grade $CO_2$, a flow rate of at least about 1.0 liters per minute is critical to achieving this objective. Given the above dimensions, and the supply of typical medical grade $CO_2$, a flow rate less than 0.8 liters per minute is not sufficient to prevent significant accumulation of moisture on the laparoscope lens.

In a representative embodiment, for a sheath 14 having an inside diameter of 0.405 inch and an outside diameter of 0.486 inch, and a length of 11.25 inch (which accommodates passage of a typical 10 mm laparoscope and its own passage through a conventional trocar) (i.e., $S_w$=0.081 inch), the total area available in the sheath wall is 0.056 square inches. Based upon required structural support within the wall (inside, outside, and radial) the total available area for lumens to transport fluids is 0.027 square inch.

In a representative embodiment, the total lumen area is occupied by five lumens 34 to 42. The area of each lumen can be maximized by selection of lumen geometry. In a representative embodiment, lumen geometry is generally triangular or pie shaped with rounded corners. The radial walls that separate the lumens within the sheath 14 are sized to minimize the spacing between the lumens.

In a representative embodiment, $CO_2$ transport is accomplished by the two lumens 34 and 36 that extend about 175 degrees about the outer circumference of the sheath 14 and comprising a flow area of 0.013 square inches. Sterile liquid transport is accomplished by one lumen 38 comprising a flow area of 0.003 square inches.

4. Pneumatic Characteristics.

As diagrammatically shown in FIG. 29, the deflector assembly 64 overhangs the laparoscopic lens by a prescribed transverse distance, defining a deflection width X, sufficient to change the direction of $CO_2$ flowing axially through lumens 34 and 36 of the sheath 14 (i.e., along the axis of the laparoscope shaft) into a non-axially, transverse path across the laparoscopic lens. The distance of the deflection width X should not extend to the point that is obstructs the field of the view of the laparoscopic lens. This is an example where a pneumatic characteristic of the deflector assembly 64 overlaps with an optical characteristic. Further optical characteristics will be described in greater detail below.

As also shown in FIG. 29, the deflector assembly 64 must also project axially beyond the distal terminus of the sheath 14 by a prescribed axial distance, defining an air channel distance Y, sufficient to maintain the $CO_2$ flowing along the path bounded by the deflection width X at a distance sufficiently close (proximal) to the laparoscopic lens.

Together, the deflection width X and the channel distance Y define the pneumatic characteristics of the deflection assembly 64. At the desired minimum flow rate, the pneumatic characteristics create a flow path that diverts $CO_2$ from the lumens 34 and 36 at the desired flow velocity across the laparoscopic lens toward the facing side of the deflection assembly 64 (see FIGS. 24 and 27). In the illustrated embodiment (see FIG. 29), the facing side of the deflection assembly 64 comprises a dead end, because the lumens 40 and 42 are blocked. The $CO_2$ from lumens 34 and 36 that is diverted across the laparoscopic lens encounters another air flow diversion at the facing side of the deflection assembly 64 (i.e., by blocked lumens 40 and 42), which is defined by a deflection width X and a channel distance Y at that end of the flow path. As FIG. 29 shows, reencountering an airflow diversion at this end of the flow path can serve to redirect the $CO_2$ back across the laparoscopic lens. A rolling vortex can be created that extends across and beyond the laparoscopic lens. The rolling vortex creates an air curtain across the lens sufficient to defog the lens. The rolling vortex is position beyond the lens with a sufficient air velocity to attract the particles away from the lens and thereby avoid entrainment or deposition of particles on the lens. To avoid entrainment, it is desirable that the vortex attracts particles away from the lens in a direction (when looking down the scope in a distal direction) toward a 3 O'clock (090) or Right Side or in a direction (also when looking down the scope in a distal direction) toward a 9 O'clock (270) or Left Side. As FIG. 29 generally shows, the rolling vortex appears to spiral about an axis that is generally transverse the axis of the sheath. $CO_2$ eventually exits the rolling vortex in a flow path that extends generally parallel to the axis of the sheath 14, carrying the particles with it.

Example 1

A plume of water vapor (mist) is created by an ultrasonic transducer and channel through a tube. The distal end of sheath 14 (with a deflection assembly 64) is positioned over the plume, and $CO_2$ is conveyed through the deflection assembly 64 in the manner described. FIG. 25B is a photograph demonstrating the presence of a "vortex shearing" effect across and beyond the laparoscopic lens for a deflection assembly 64 on a blunt sheath 14. FIG. 26B is a photograph demonstrating the presence of a "vortex shearing" effect across and beyond the laparoscopic lens for a deflection assembly 64 on a 30° angled sheath 14. In both instances, the deflected airflow is shown, with the accompanying shear and the resulting clear zone across and beyond the laparoscopic lens.

Figure 25A:
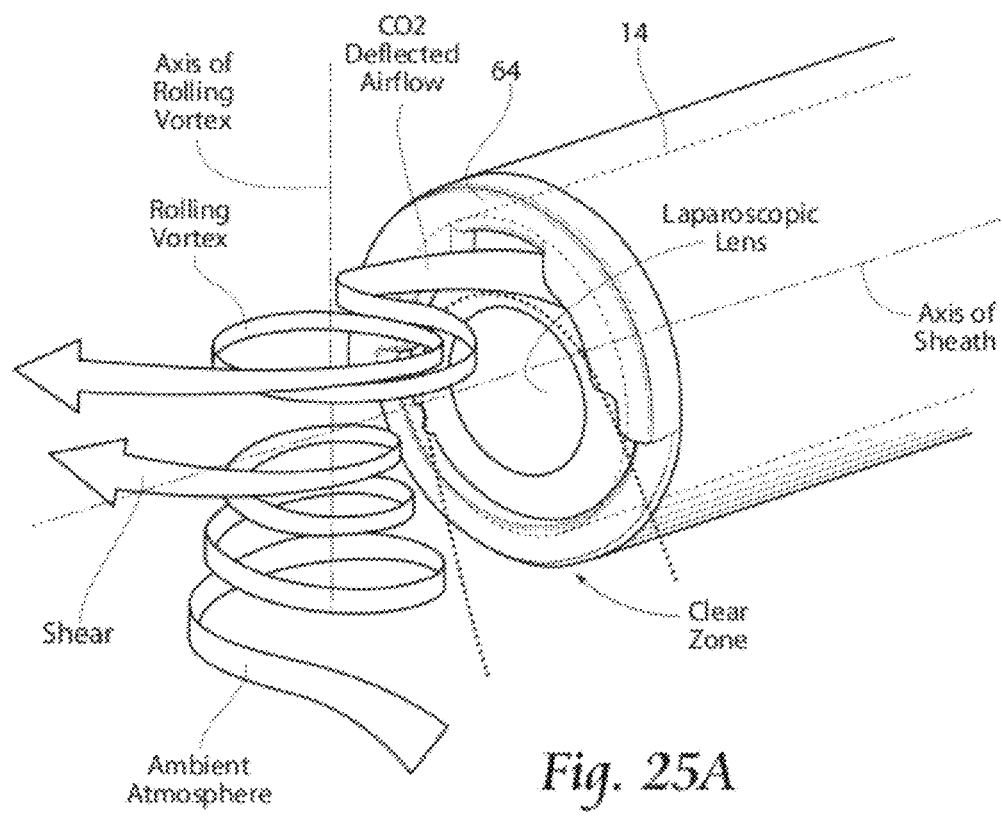
FIG. 25A is a perspective, diagrammatic view of the deflector assembly shown in FIG. 23, assembled to the sheath, depicting a rolling vortex that is created by the deflector assembly that extends across and beyond the laparoscopic lens.
Figure 25B:
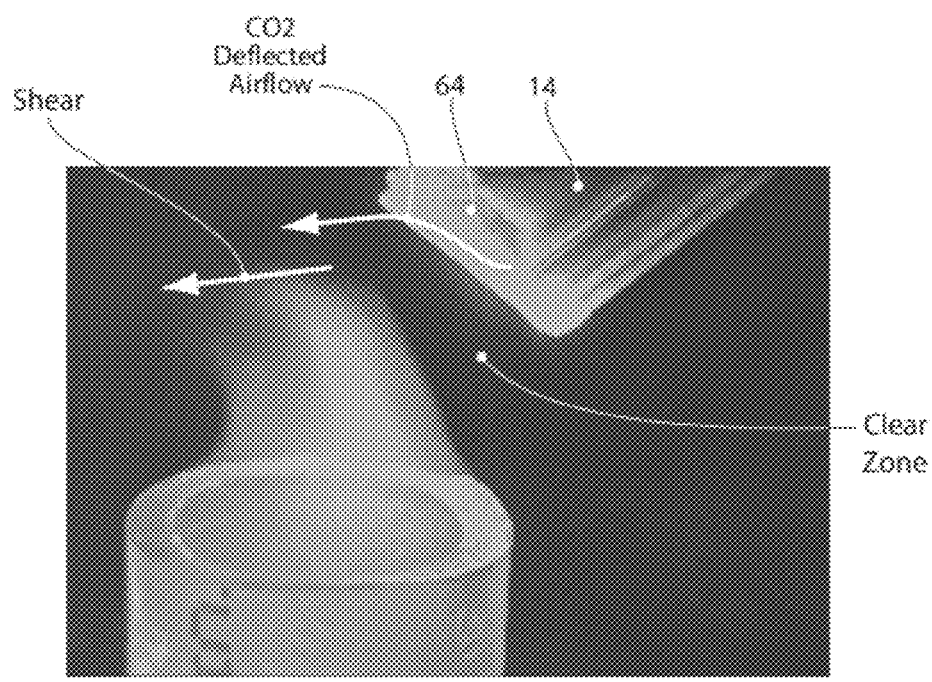
FIG. 25B is a photograph showing the effects of the rolling vortex depicted in FIG. 25A in creating a clear zone across and beyond the laparoscopic lens.
Figure 28A:
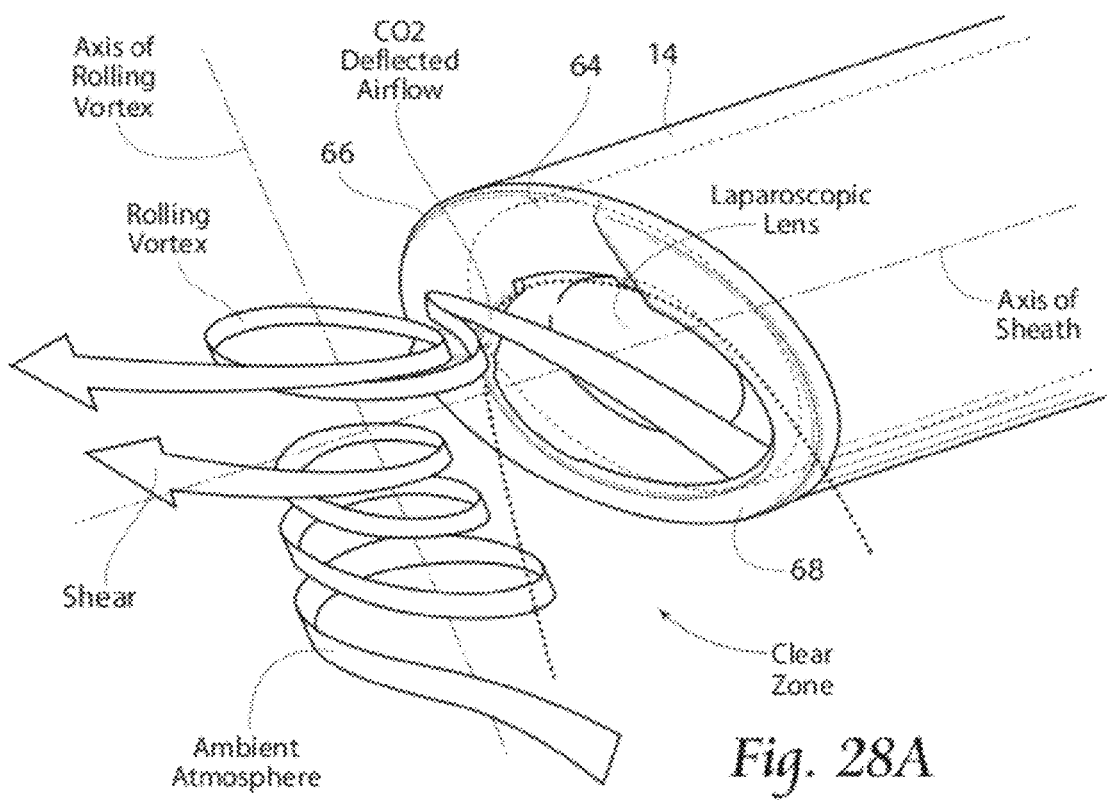
FIG. 28A is a perspective, diagrammatic view of the deflector assembly shown in FIG. 26, assembled to the sheath, depicting a rolling vortex that is created by the deflector assembly that extends across and beyond the laparoscopic lens.
Figure 28B:
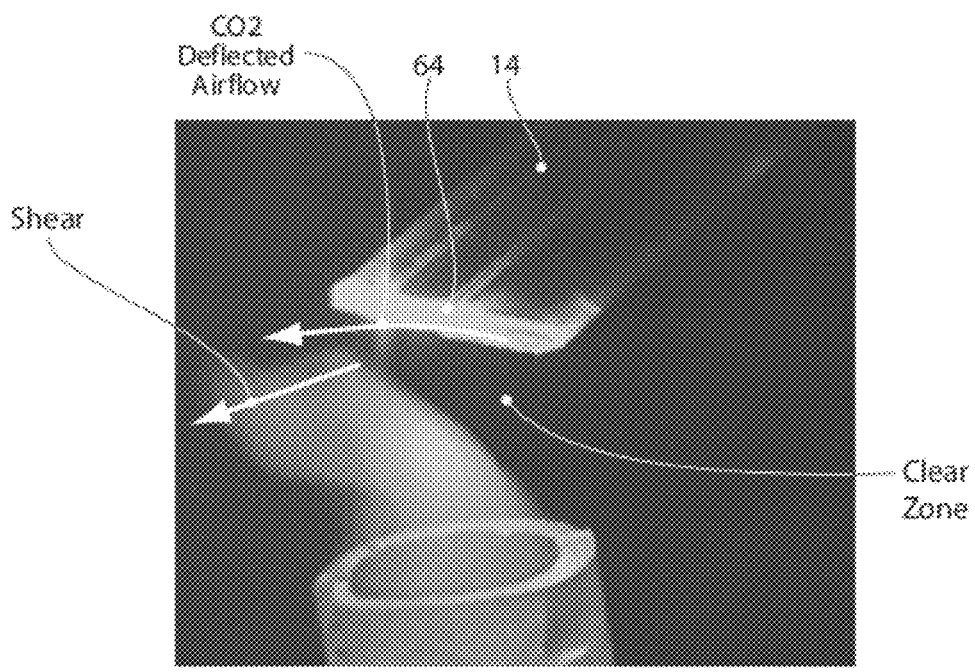
FIG. 28B is a photograph showing the effects of the rolling vortex depicted in FIG. 28A in creating a clear zone across and beyond the laparoscopic lens.

The rolling vortex for a blunt end sheath 14 is depicted in FIG. 25A (with a corresponding photograph shown in FIG. 25B), and the rolling vortex for an angled sheath is depicted in FIG. 28A (with a corresponding photograph shown in FIG. 28B). The rolling vortex is observed to create a "vortex shearing" effect across and beyond the laparoscopic lens, disrupting the ambient atmosphere at or near the tip of the sheath 14 to create a clear zone that extends across and beyond (by approximately 0.25 inch or more) the plane of the lens. The clear zone created by the vortex shearing effect prevents fogging, as well as deflects smoke and surgical debris away from the viewing field of the laparoscopic lens during surgery.

5. Optical Characteristics

The optical characteristics of the deflector assembly 64 are selected (i) to not block or reduce the illuminated image of the operating field provided by the laparoscope 12; (ii) not decrease the intensity of the illumination provided by the laparoscope 12 on the operating field; and (iii) prevent reflection of illumination light at the lens of the laparoscope 12.

As discussed above, the maximum deflection width X takes into account one of the desirable optical characteristics; namely, the deflection width X should not obstruct the field of the view of the laparoscopic lens.

To prevent the decrease of the illumination, the deflector assembly 64 is desirably made from a material having high light transmission properties (i.e., transparency), to not interfere with the passage of light through the light cable 30 onto the operating field as well as the passage of the reflected image conveyed to the camera cable 32 of the laparoscope 12.

Furthermore, the material and surface finish of the deflector assembly 64 must pose minimal reflectively to light. In a representative embodiment, the deflector assembly 64 is made from Bayer Makrolen Rx1805 with a surface finish defined as SPI/SPE A-3.

6. Orientation

As before described, $CO_2$ transport is accomplished by two lumens 34 and 36 that extend about 175 degrees about the outer circumference of the sheath 14. For a 0° shaft tip (see FIG. 23), the orientation of the deflector assembly 64 relative to the laparoscopic lens is not believed to be critical. However, for angled shafts (e.g., 30° shaft tips and 45° shaft tips) (see FIG. 26), the orientation of the deflector assembly 64 having this pneumatic characteristic relative to the laparoscopic lens is believed to be critical.

As FIG. 26 shows, the angled tip of a typical laparoscope 12 has a high end 66 and a low end 68. The lens slopes at the prescribed angle between the high end 66 and the low end 68. In a laparoscope 12 having a angled tip, the illumination cable (transmitting light onto the operating field) is located at the high end 66 of the angled tip, and the camera cable (transmitting reflected light back to the camera) is located at the low end 68 of the angled tip. To provide the desired vortex shear effect on an angled tip having a pneumatic characteristic just described, it is believed to be critical that the deflector assembly 64 be oriented relative to the sloped laparoscopic lens such that the flow $CO_2$ is directed across the sloped plane of the lens from the low end 68 of the tip (from lumens 34 and 36) toward the high end 66 of the tip (toward the dead end lumens 40 and 42). In this arrangement, the defogging and debris deflection flow path originates proximal to the camera cable, which effectively comprises the eyes of the OR team. In this arrangement, the "vortex shearing" effect is across and beyond the sloped plane of the laparoscopic lens to achieve optimal defogging and debris deflection.

G. Sterile Liquid Flush

As previously explained, if desired, the tubing set 16 can also include, connected to the quick exchange coupler 22, a length of tubing 70 sized and configured for connection to a source 72 of sterile liquid, such as saline or sterile water (as shown in FIGS. 1A and 2A). As shown in FIGS. 1A/2A, the sterile liquid tubing 70 desirably includes an in-line pumping device 72, which in the illustrated embodiment comprises a 20 cc syringe filled with sterile liquid fluid and connected by a tubing luer-lock on the saline tubing.

Preferably, the sterile liquid includes in solution a "surface-active agent" (surfactant) that stabilizes mixtures of oil and water (e.g., fat) by reducing the surface tension at the interface between the oil and water molecules.

In one preferred form of the sterile liquid solution, the solution comprises a dioctyl sulfosuccinate salt, such as dioctyl sodium sulfosuccinate (DSS) (also referred to as docusate sodium), docusate calcium, or docusate potassium. A buffer may be used to provide a neutral and stabilized pH between 6.5-7.5. The remainder of the solution may comprise water for injection (WFI) quality water.

The higher the percentage of DSS shortens the time for cleaning the lens, but increases the tendency for the formation of bubbles on the lens. Conversely, a lower percentage of DSS in the solution has a lower tendency for the formation of bubbles, but also has a longer time for cleaning the lens. The present invention provides a solution that balances these considerations. For example, a preferred formula may comprise DSS between 0.05%-0.25% w/v of the solution, with a more preferred range of the DSS being between 0.1%-0.2% w/v of the solution.

One preferred solution comprises 1.5 g DSS/1000 ml WFI water, 2 ml phosphate buffer/1000 ml WFI water, with the remaining amount of the solution being WFI water. The solution comprises 0.15% w/v DSS, 0.002% w/v buffer, with the buffer concentration being 0.2M.

When the quick exchange coupler 22 and the quick exchange coupling 20 are connected, operation of the in-line pumping device 72 directs bursts of the sterile liquid through the lumen 38 in the sheath 14 to the deflector assembly 64 at the distal end of the sheath 14.

In this arrangement, the deflector assembly 64 is also sized and configured to direct the burst of sterile liquid in a desired path across the laparoscopic lens. The bursts of sterile liquid serve to flush debris off the end of the lens that may eventually accumulate, thereby cleaning the lens. Thereafter, bursts of air supplied by the lumens 34 and 36 to the deflector assembly 64 by a squeeze pump 74 in the tubing set 16 (see FIGS. 1A/2A) serve to clear residual fluid droplets off the lens to maintain an acceptable view.

In an illustrative embodiment (see FIGS. 24 and 27), the deflector assembly 64 directs the bursts of sterile liquid along a plurality of individual diverging channels 76 (three are shown). The diverging channels 76 distribute the bursts of sterile liquid in a fanning pattern across the lens of the laparoscope 12. In the illustrative embodiment, the diverging channels 76 discharge the bursts of sterile liquid in a path that is generally ninety-degrees to the path of CO2. This orientation of the sterile liquid path relative to the $CO_2$ path across the lens, optimal for effective lens cleaning, applies to both 0° shaft tips and angled tips (e.g., 30° shaft tips and 45° shaft tips).

II. ILLUSTRATIVE ALTERNATIVE EMBODIMENTS

Figure 30:
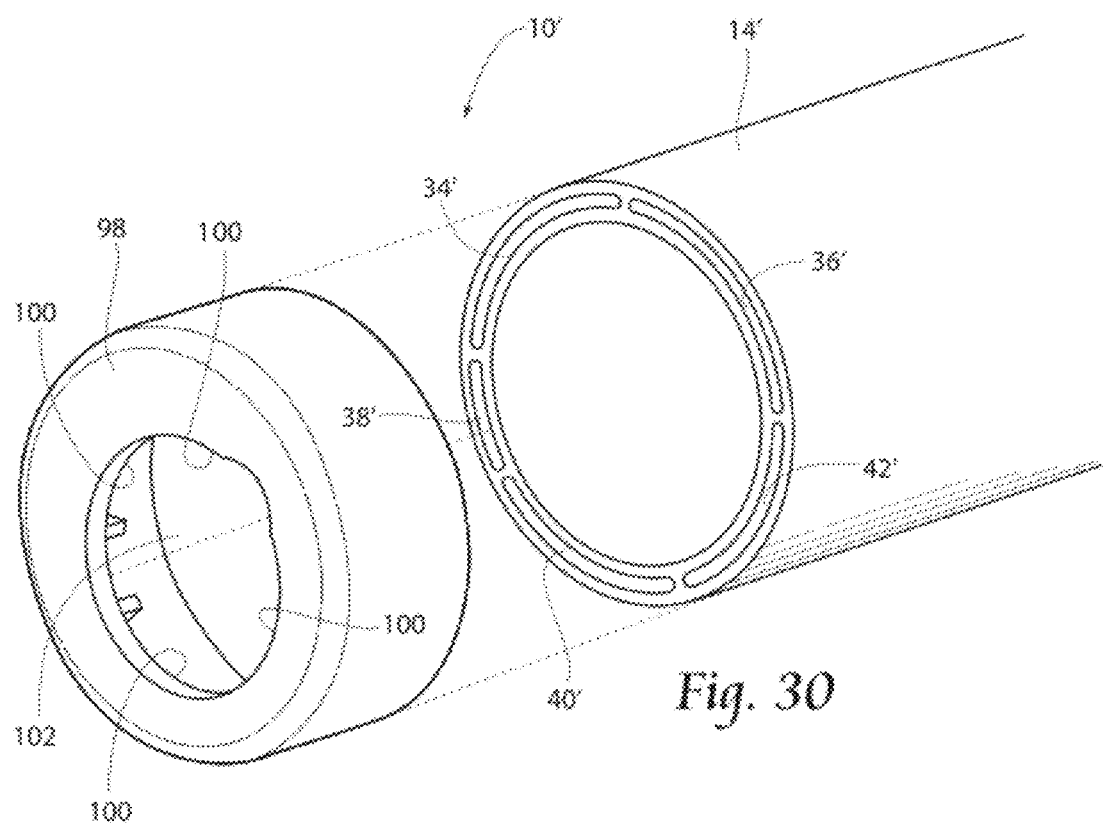
FIG. 30 is an enlarged, exploded view of another embodiment of a deflector assembly for use with a laparoscope having a 0° shaft tip.
Figure 31:
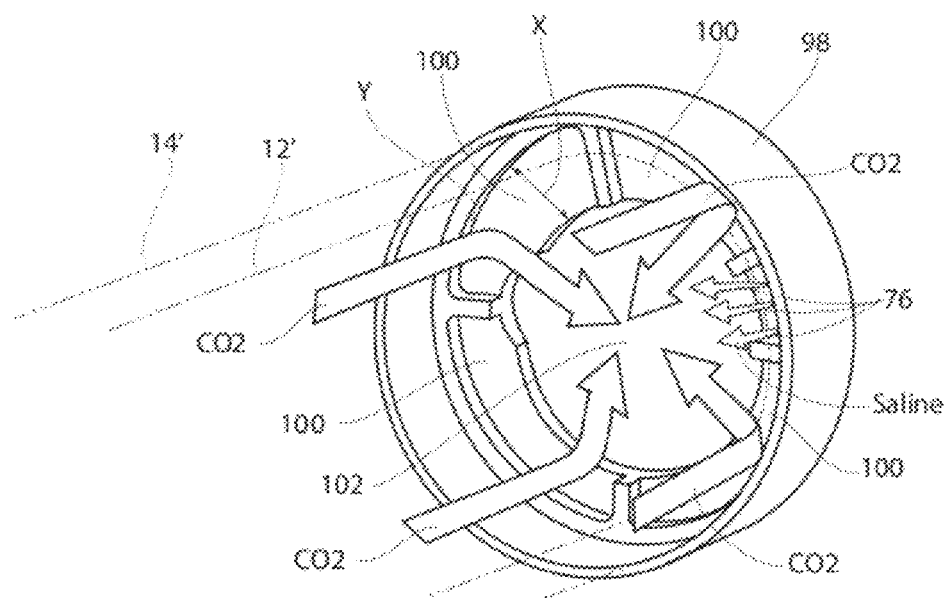
FIG. 31 is a perspective view of the deflector assembly shown in FIG. 30 when viewed from the inside of the sheath.
Figure 32:
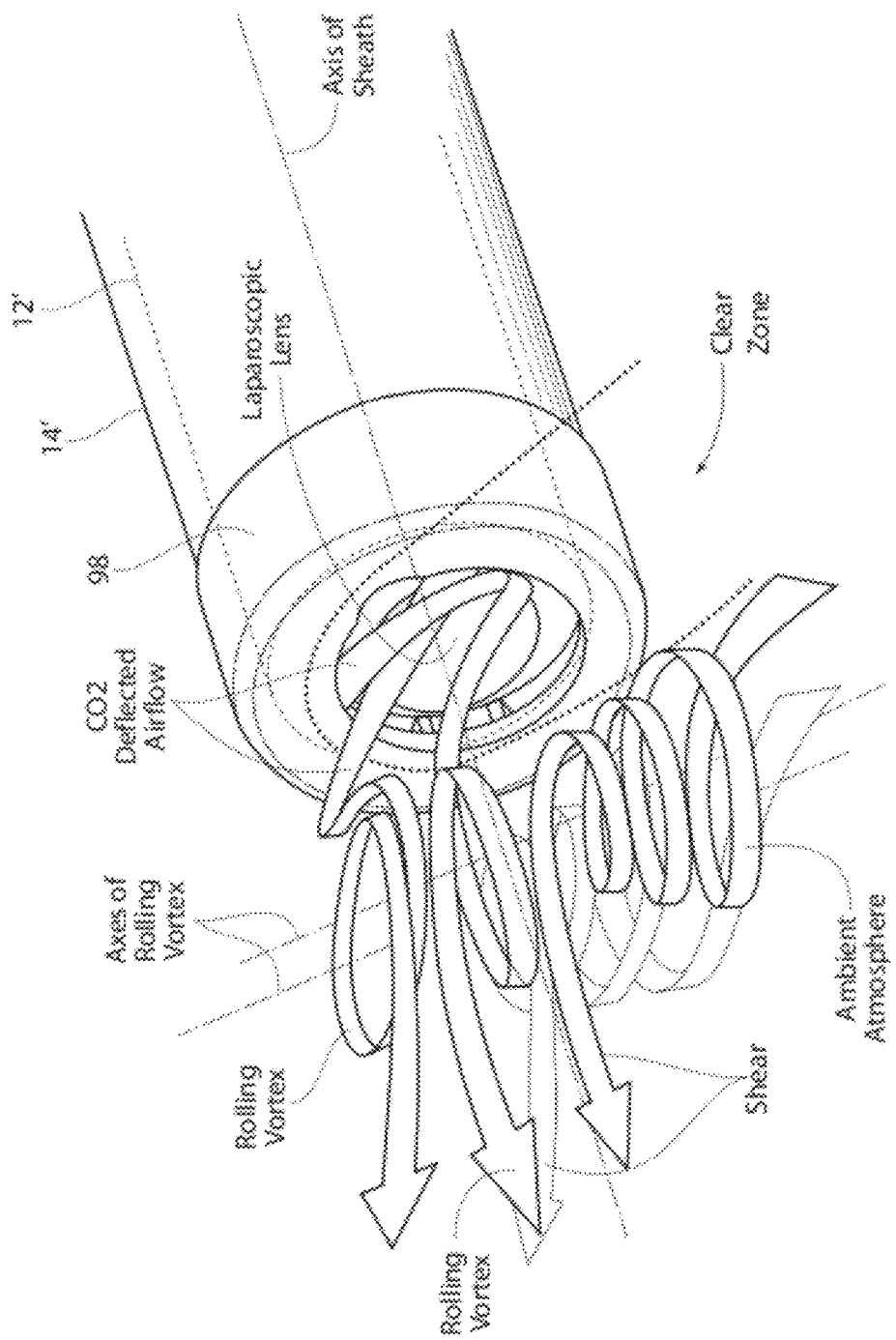
FIG. 32 is a perspective, diagrammatic view of the deflector assembly shown in FIG. 30, assembled to the sheath, depicting a rolling vortex or a pattern of rolling vortices that can be created by the deflector assembly and that extend across and beyond the laparoscopic lens, creating a clear zone across and beyond the laparoscopic lens.
Figure 33:
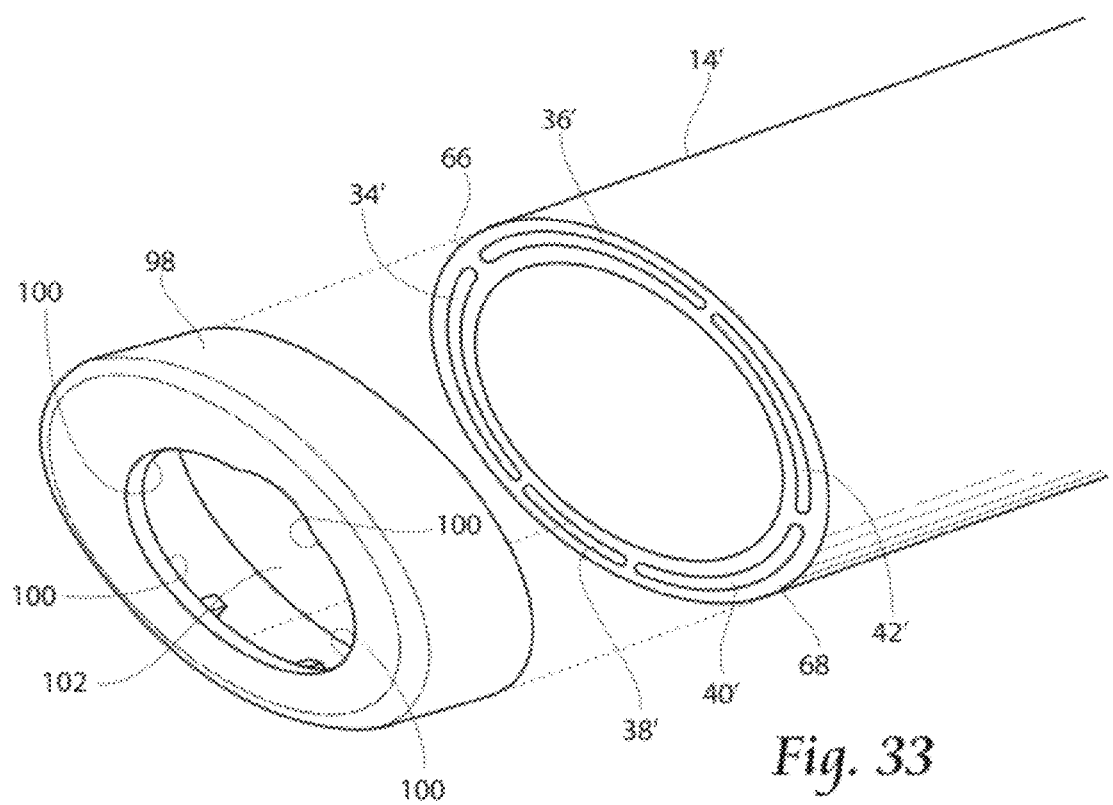
FIG. 33 is an enlarged, exploded view of another embodiment of a deflector assembly for use with a laparoscope having an angled shaft tip.

FIGS. 30 to 32 and 33 to 35 show another embodiment of view optimizing assembly 10' for use in association with a state of the art laparoscope (not shown). In FIGS. 30 to 32, the view optimizing assembly 10' includes a shaft 14' for a laparoscope possessing at 0° (blunt) shaft tip In FIGS. 33 to 35, the view optimizing assembly 10' includes a shaft 14' for a laparoscope possessing an angle shaft tip (e.g., a 30° shaft tip or 45° shaft tip). An angled shaft tip is measured as angled from a blunt shaft tip, i.e. a shaft tip that is perpendicular to the central axis of the laparoscope. Thus, a 30° shaft tip would be angled 30° from a plane that is perpendicular of the central axis of the laparoscope.

In many respects, the fit, form, and function of the view optimizing assembly 10 shown in FIGS. 30 to 32 and 33 to 35 are at least equivalent to those previously described. As previously described, the sheath 14' comprises multiple interior lumens 34'; 26'; 38'; 40'; and 42', and the multi-lumen sheath 14 is sized and configured to mounts over the shaft of the laparoscope. As also previously described, the shaft 14' is intended to be coupled via a manifold to a tubing set in the manner previously described (shown in FIGS. 15A/16A), to connect the lumens of the sheath 14' to an existing carbon dioxide (CO2) insufflation circuit, as well as to a source of flushing liquid, in the manner shown in FIGS. 1A/2A.

In the embodiment shown in FIGS. 30 to 32 and 33 to 35, the sheath 14' includes at its distal end a deflector assembly 98. As the deflector assembly 64 previously described, the deflector assembly 98 projects a predetermined distance beyond the distal end of the sheath 14, and thus also a predetermined distance beyond the lens at the distal end of the laparoscope 12' (see FIGS. 32 and 35). In the embodiment illustrated in FIGS. 30 to 32 and 33 to 35, the deflector assembly 98 comprises an injected molded part (see FIGS. 30 and 33) that is sized and configured to be glued onto the distal tip of the sheath 14', without need of any mounting tabs that project into any one of the lumens. Therefore, mounting the deflector assembly 98 onto the sheath 14' does not sacrifice any $CO_2$ flow capacity. In this arrangement, there are also no dead ends to any $CO_2$ flow path. $CO_2$ can be conveyed to the deflector assembly 98 by all four lumens 34'; 36'; 40'; and 42' in the sheath 14.

Figure 34:
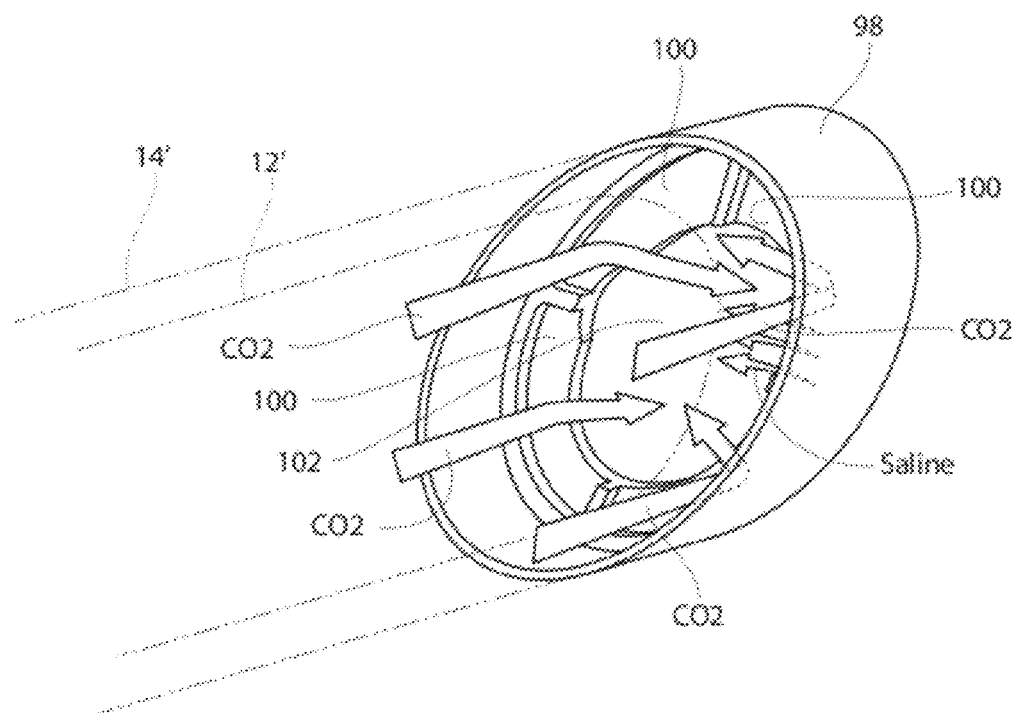
FIG. 34 is a perspective view of the deflector assembly shown in FIG. 33 when viewed from the inside of the sheath.

As shown in FIGS. 31 and 34, in this arrangement, $CO_2$ is circumferentially diverted from four diversion regions 100 formed on the deflector assembly 98, each defining a deflection width X and a channel distance Y. Thus, $CO_2$ is diverted by the four circumferentially spaced regions 100 across the laparoscopic lens, lying along an arc of about 350°. The remaining lumen 38 conveys sterile flushing liquid, as already described.

In the illustrated embodiment (see FIGS. 30 and 33), the aperture 102 defined in the middle of the deflector assembly 98, into which the $CO_2$ is diverted across the laparoscopic lens, is smaller in diameter than the aperture in the center region of the previously described deflector assembly 64 (compare, e.g., FIGS. 23 and 26). The smaller ("tighter") center region 102 in the deflector assembly 98 further centralizes the air flow region across the laparoscopic lens.

Figure 35:
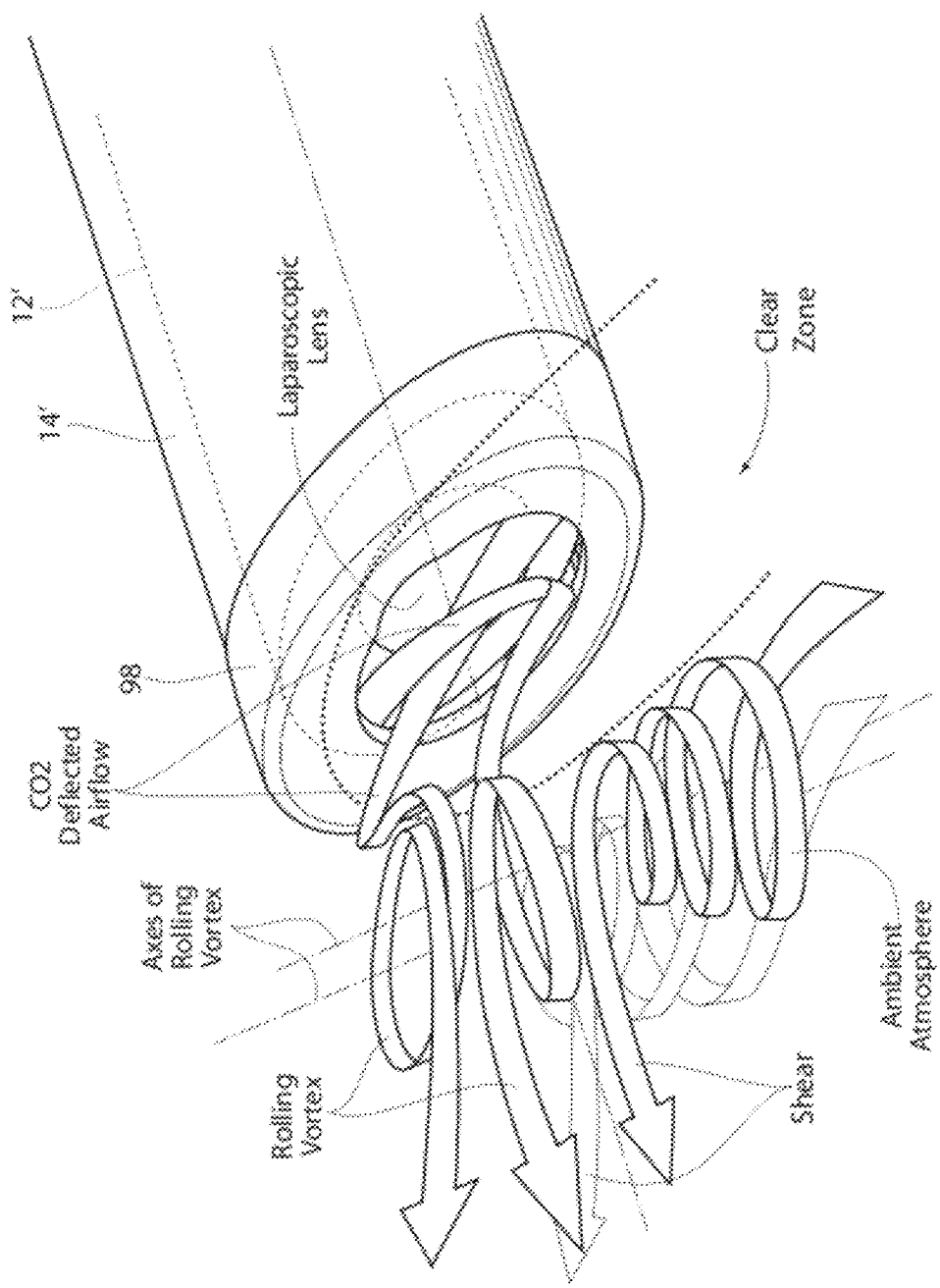
FIG. 35 is a perspective, diagrammatic view of the deflector assembly shown in FIG. 33, assembled to the sheath, depicting a rolling vortex or a pattern of rolling vortices that can be created by the deflector assembly and that extend across and beyond the laparoscopic lens, creating a clear zone across and beyond the laparoscopic lens.

As FIGS. 31 and 34 show, the four diversion regions 100 formed on the deflector assembly 64 each define a deflection width X and a channel distance Y to change the direction of $CO_2$ flowing axially through the four supply lumens 34'; 36'; 40'; and 42' of the sheath 14'. The $CO_2$ flows in four paths along an enlarged arc of about 350° transversely across the laparoscopic lens toward the facing sides of the deflection assembly 64. The $CO_2$ in each of the four paths will encounter a deflection width X and channel distant Y at their respective facing side of the deflection assembly 64. Encountering a deflection width X and channel distant Y at these ends of the flow paths can redirect the $CO_2$ back across the laparoscopic lens, adding to the flow that enters at these ends (see FIGS. 27 and 31). This rebounding flow pattern can form one or more rolling vortices, or a pattern of multiple rolling vortices, that extend across and beyond the laparoscopic lens, disrupting the ambient atmosphere at or near the tip of the sheath 14 to create a clear zone extending across and beyond the laparoscopic lens, as previously described. As FIGS. 25 and 29 generally show, each rolling vortex appears to spiral about an axis that is generally transverse the axis of the sheath 14'. The array of rolling vortices may intersect one another, forming "butterfly wing" patterns, as FIGS. 32 and 35 show. $CO_2$ eventually exits the rolling vortices in a flow path that extends generally parallel to the axis of the sheath 14, as before described with the previously described vortex embodiments.

The rolling vortex pattern for a blunt end sheath 14 is depicted in FIG. 32, and the rolling vortex pattern for an angled sheath is depicted in FIG. 35. The rolling vortex pattern creates a "vortex shearing" effect across and beyond the laparoscopic lens, disrupting the ambient atmosphere at or near the tip of the sheath 14 to create a clear zone that extends across and beyond the plane of the lens. As before, the clear zone created by the vortex shearing effect prevents fogging, as well as deflects smoke and surgical debris away from the viewing field of the laparoscopic lens during surgery.

III. OPTIMIZING THE ROLLING VORTEX PATTERN

The creation of a vortex pattern at the distal end of the sheath is the outcome of properly establishing desirable physical and pneumatic conditions at the proximal end of the sheath. The vortex pattern assures that particles are moved away from the lens, and not toward the lens (a condition called deposition or entrainment). The vortex pattern also establish a gas curtain across the lens sufficient to defog the lens.

A. Exemplary Sheath for a 5 mm Laparoscope

Figure 36A:
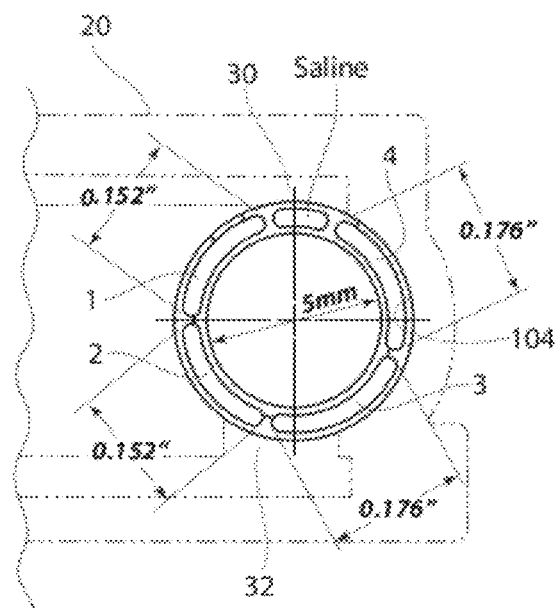
FIG. 36A is a proximal end view looking distally of the sheath like that shown in FIG. 19, sized and configured for use with a conventional 5 mm laparoscope, including dimensions and identifying Lumens 1, 2, 3, and 4 as points of future reference.

FIG. 36A shows a proximal end view of a representative embodiment of a sheath, looking distally. In this embodiment, the sheath includes a center passage sized and configured to receive a typical 5 mm laparoscope. In a representative embodiment, the maximum outer wall diameter of the sheath (at the distal end) is 0.300 inch.

The orientation of the lumens 34, 36, 40, and 42 for conveying pressured $CO_2$ to the deflection assembly 64 in this size configuration are shown. For the purpose of description, the lumens 40, 42, 36, and 34 are numbered 1, 2, 3, and 4, respectively, counterclockwise from the saline lumen 38.

As FIG. 36A shows, the radial dimension of the lumens 1, 2, 3, and 4, measured between the inner and outer walls of the lumens are equal (in a representative embodiment, 0.020 inch). However, the dimensions, expressed in degrees of arc, of lumens 1, 2, 3 and 4 differ. More particularly, the lumens 3 and 4 extend in degrees along a greater arc than lumens 1 and 2. In a representative embodiment, the lumens 3 and 4 each extend 83° (tangentially 0.176 inch), whereas the lumens 1 and 2 extend 71° (tangentially 0.152 inch). The lumens 3 and 4 are therefore in volume larger than lumens 1 and 2.

In use with an angled tip sheath (see FIG. 36), the larger lumens 3 and 4 (i.e., lumens 36 and 34) are positioned at the low end 68 of the tip in a desired registration with the deflector assembly 64, such that the flow $CO_2$ from the lumens 3 and 4 is directed across the sloped plane of the lens from the low end 68 of the tip toward the high end 66 of the tip. In this arrangement, the defogging and debris deflection flow path originates proximal to the camera cable, which effectively comprises the eyes of the OR team. In this arrangement, the "vortex shearing" effect (see FIG. 28A) is across and beyond the sloped plane of the laparoscopic lens to achieve optimal defogging and debris deflection.

Figure 18:
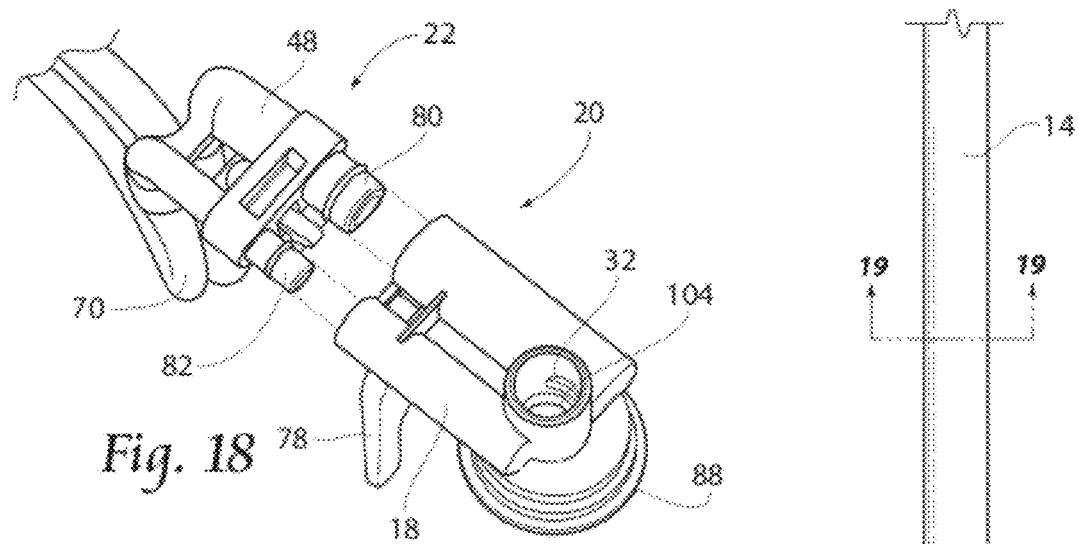
Figure 19:
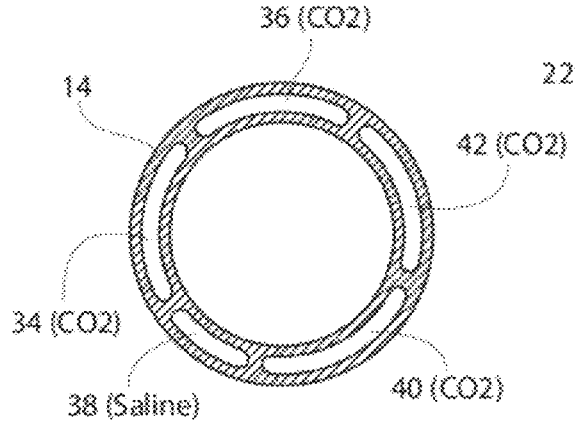
FIG. 19 is a perspective view of the manifold, showing in exploded view the keyed fitting of the sheath within the manifold junction.
Figure 20:
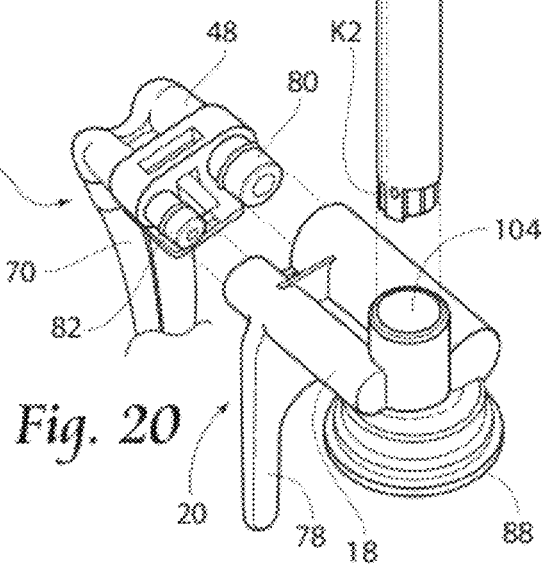
FIG. 20 is a section view of the sheath taken generally alone line 20-20 in FIG. 19, showing the orientation of the lumens of the sheath provided by the keyed fitting of the sheath to the manifold junction.
Figure 36B:
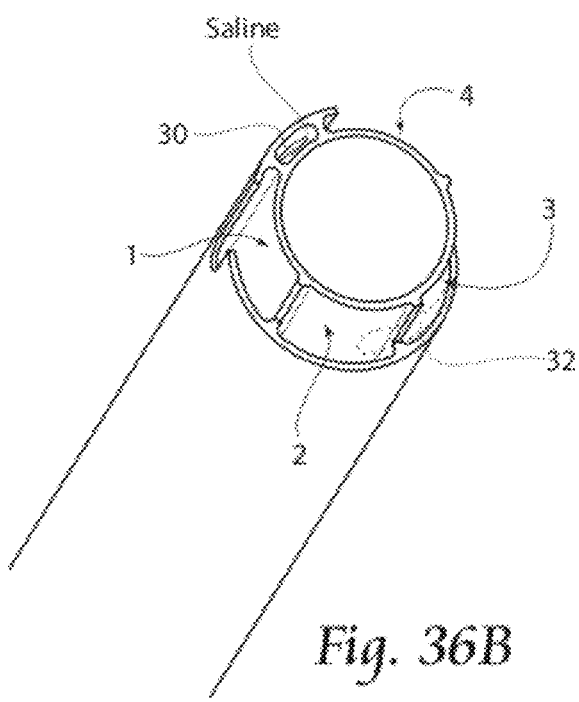
FIG. 36B is a perspective side view of the proximal end of the sheath shown in FIG. 36A, trimmed to form a plenum.

As shown in FIG. 36B, the outer wall of the proximal end of the sheath, which is sized and configured to be fitted into the manifold junction 104 (see FIG. 19), is reduced or trimmed in diameter to define, when fitted into the manifold junction 104, a plenum between the interior of the manifold junction 104 and the trimmed outer wall of the sheath. The plenum communicates with the lumens 1, 2, 3, and 4. Pressurized $CO_2$ enters the plenum through the inlet passage 32 (see FIG. 36A, as is also shown in FIG. 18), which is located 180° opposite to the inlet passage 30 for saline (see FIG. 29A, as is also shown in FIG. 10).

In a representative embodiment, 0.117 inch of the outer wall is removed for an axial distance of 0.140 inch measured from the proximal terminus of the sheath (which will also be called the "trim distance) to form the plenum.

Figure 36C:
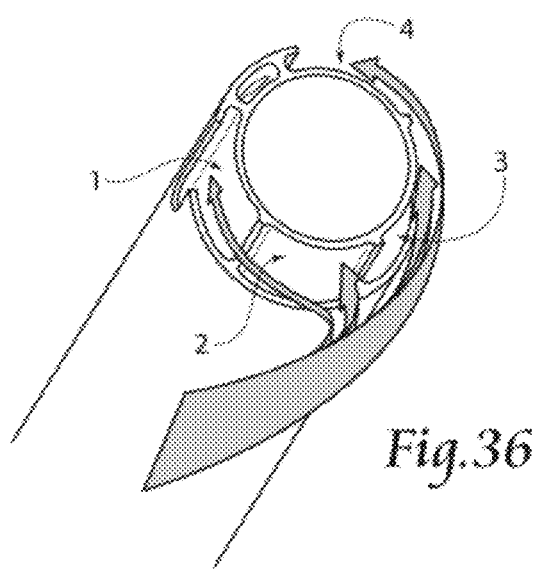
FIG. 36C is a perspective side view of the proximal end of the sheath shown in FIG. 36B, showing the direction and deflection of pressurized $CO_2$ introduced in the plenum, for entry into the Lumens 1, 2, 3, and 4.

As FIG. 36C shows, in this representative embodiment, pressurized $CO_2$ enters the plenum through the inlet port 32 at a velocity of 2 m/sec. The inlet port 32 directs the pressurized $CO_2$ airflow simultaneously into lumens 2 and 3 in a counterclockwise direction. As can be seen in FIG. 36A, a greater extent of lumen 3 overlaps the inlet port 32 than lumen 2, because the combined angular reach of lumens 3 and 4 is greater than the combined angular reach of lumens 1 and 2.

The pressurized $CO_2$ enters lumen 3 in a counterclockwise flow direction toward lumen 4. A smaller proportion of the pressurized $CO_2$ enters lumen 2. To reach lumen 1, there must be a sufficient clockwise backflow to direct the $CO_2$ toward lumen 1. Given the size and configuration of the plenum and lumens 1, 2, 3, and 4 shown in FIGS. 36A, 36B, the proportional distribution of $CO_2$ in the plenum among lumens 1, 2, 3, and 4, as shown in FIG. 29C, occurs.

As shown in FIG. 36C, the plenum directs a proximal $CO_2$ airflow, at an entrance velocity of 2 m/sec, into the lumens 1, 2, 3, and 4 and through the deflector assembly 64 at the distal end of the sheath. The deflector assembly 64 includes a channel or gap distance Y of 0.005 inch (see FIG. 29.) The deflector assembly 64 directs the $CO_2$ at an increased exit velocity across the 5 mm lens, creating a desired rolling vortex and "vortex shearing" effect, which is shown in FIGS. 25B and 28B, and as described in Example 1 (which tested a 5 mm sheath). The vortex pattern moves particles away from the lens, avoiding deposition or entrainment. The vortex pattern also establish a gas curtain across the lens sufficient to defog the lens.

B. Exemplary Sheath for a 10 mm Laparoscope

FIG. 25A shows a proximal end view of a representative embodiment of another, larger sheath, looking distally. In this embodiment, the sheath includes a center passage that is sized and configured to receive a typical 10 mm laparoscope. In a representative embodiment, the maximum outer wall diameter of the sheath (at the distal end) is 0.486 inch.

Figure 37A:
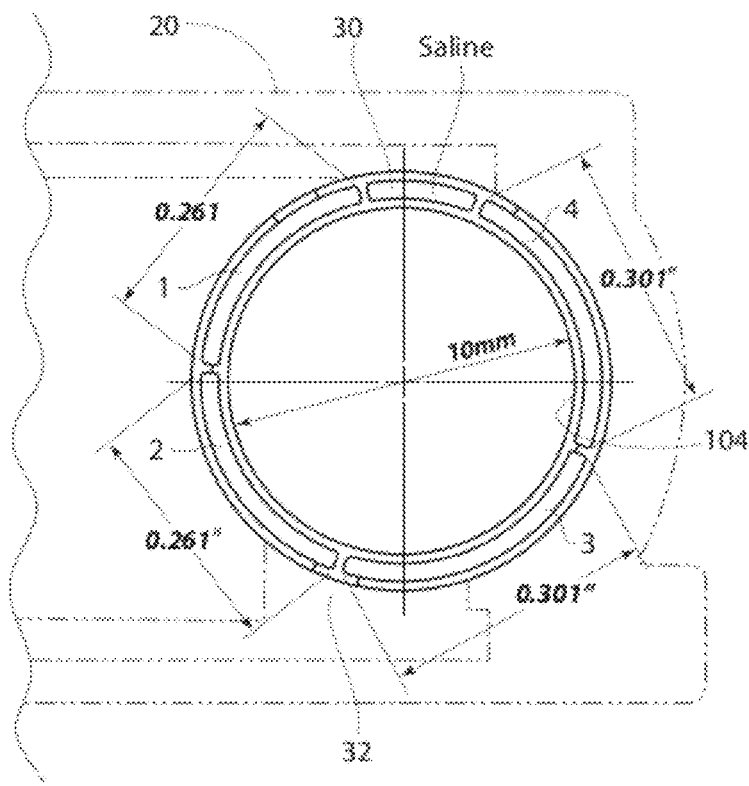
FIG. 37A is a proximal end view looking distally of the sheath like that shown in FIG. 36A, but sized and configured for use with a conventional 10 mm laparoscope, including dimensions and identifying Lumens 1, 2, 3, and 4 as points of future reference.

The orientation of the lumens 34, 36, 40, and 42 for conveying pressured $CO_2$ to the deflection assembly 64 in FIG. 37A are shown to be generally the same as in FIG. 36A. As in FIG. 36A, for the purpose of description, the lumens 40, 42, 36, and 34 are numbered 1, 2, 3, and 4, respectively, counterclockwise from the saline lumen 38.

As FIG. 37A shows, the radial dimension of the lumens 1, 2, 3, and 4, measured between the inner and outer walls of the lumens are equal (in a representative embodiment, 0.020 inch). However, as in the embodiment shown in FIG. 29A, the dimensions of lumens 1, 2, 3 and 4, expressed in degrees of arc, differ. As in FIG. 36A, each lumen 3 and 4 individually extends 83°, and each lumen 1 and 2 individually extends 71°. Because of the overall larger diameter of the sheath in FIG. 37A, the same degrees of arc translate into larger tangential dimensions in FIG. 30A: the lumens 3 and 4 extend tangentially 0.301 inch, and the lumens 1 and 2 extend tangentially 0.261 inch. As in FIG. 36A, the lumens 3 and 4 in FIG. 37A are in volume larger than lumens 1 and 2 in FIG. 37A, for the reasons stated with respect to the FIG. 36A embodiment.

Figure 37B:
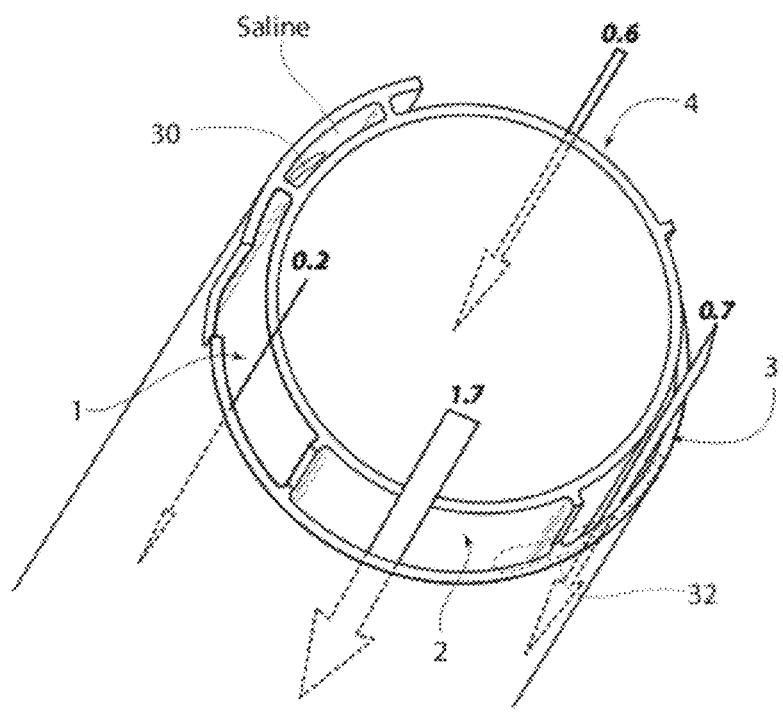
FIG. 37B is a perspective side view of the proximal end of the sheath shown in FIG. 37A, trimmed to form a plenum that corresponds with Device 1 in Table 1 of Example 2, and annotated to show the relative air speeds of pressurized $CO_2$ that is directed and deflected within the plenum into the Lumens 1, 2, 3, and 4.

As shown in FIG. 37B, the outer wall of the proximal end of the sheath, which is sized and configured to be fitted into the manifold junction 104 (in the manner shown in FIG. 19), is (as in FIG. 36B) reduced or trimmed in diameter. The trimmed diameter defines, when fitted into the respective manifold junction 104, a plenum between the interior of the manifold junction 104 and the sheath. The plenum communicates with the lumens 1, 2, 3, and 4.

In the representative embodiment shown in FIG. 37B, 0.140 inch of the outer wall is removed for an axial distance of 0.140 inch measured from the proximal terminus of the sheath (which will also be called the "trim distance") to form the plenum.

As generally explained with regard to FIG. 36C, pressurized $CO_2$ enters the plenum shown in FIG. 37B through the inlet port 32 at an entrance velocity of 2 m/sec. The inlet port 32 directs the pressurized $CO_2$ airflow simultaneously into lumens 2 and 3 in a counterclockwise direction. As can be seen in FIGS. 37A and 37B, because the combined angular reach of lumens 3 and 4 is greater than the combined angular reach of lumens 1 and 2, a greater volume of lumen 3 overlaps with the inlet port 32 than does lumen 2.

As previously explained, within the plenum, the pressurized $CO_2$ enters lumen 3 in a counterclockwise flow rotation toward lumen 4. A smaller proportion of the pressurized $CO_2$ enters lumen 2. To reach lumen 1, there must be a sufficient clockwise backflow to direct the $CO_2$ toward lumen 1. However, as the next Example 2 demonstrates, given the larger proportions of the plenum and lumens 1, 2, 3, and 4 in FIGS. 37A and 37B, the direction and deflection of $CO_2$ by the plenum is not uniform in terms of variance of among the air speeds in the lumens, as well as in terms of the differential between the maximum and minimum air speeds: the air speeds fluctuate from 0.1 m/sec (at lumen 1) to 0.7 m/sec (at lumen 4) and 0.9 and 1.0 m/sec (at lumens 2 and 3), and the maximum air speed of $CO_2$ measured (in lumen 2) is 8.5 times the minimum air speed measured (in lumen 1). Despite experiencing an increased exit velocity through the deflection assembly 64 at the distal end of the sheath (due to a reduced channel or gap distance Y of 0.005 inch), the direction and deflection and distribution of $CO_2$ within the entire proximal plenum is not uniform at the lumens 1, 2, 3, and 4. An insufficiently uniform direction and deflection and distribution of $CO_2$ within the entire plenum results in two undesired outcomes: (i) no rolling vortex is created; and/or (ii) an area of low pressure is created drawing the debris towards the lens, causing deposition or entrainment.

Example 2

Various sheaths (identified as Devices 1 to 7) were constructed with distal plenums having differing sizes and configurations. These are described in the following Table 1:

TABLE 1

Figure 38A:
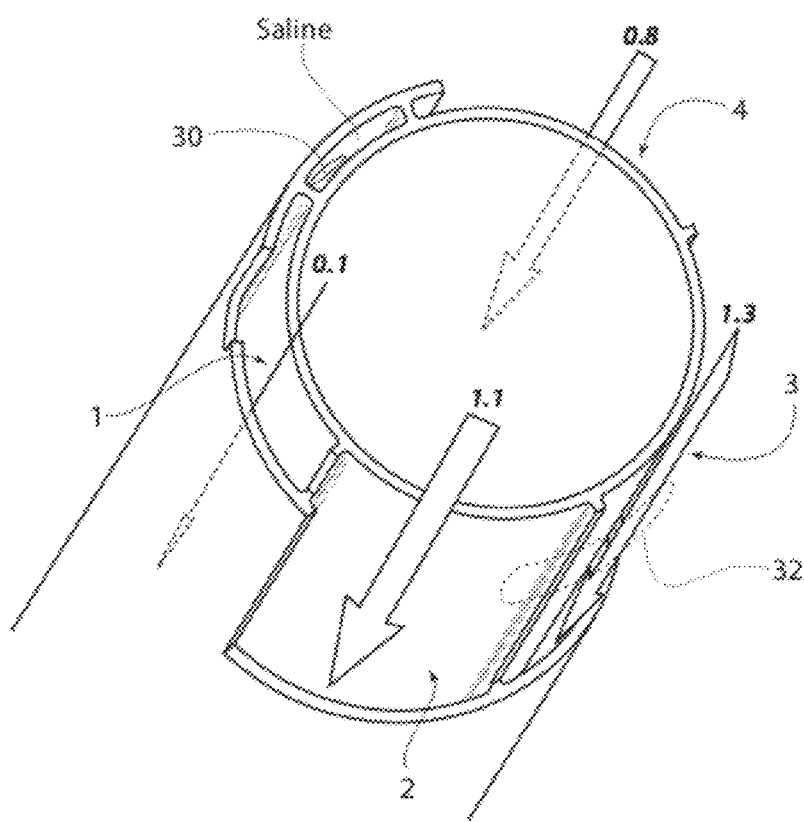
FIG. 38A is a perspective side view of the proximal end of an alternative embodiment of a sheath, trimmed to form a plenum that corresponds with Device 2 in Table 1 of Example 2, and annotated to show the relative air speeds of pressurized $CO_2$ that is directed and deflected within the plenum into the Lumens 1, 2, 3, and 4.

| | Sheaths Constructed | |
|---|---|---|
| Device Designations | Proximal Plenum Configuration | Proximal Trim Distances |
| 1 | As Shown in FIG. 37B | All lumens 0.140 inch |
| 2 | As Shown in FIG. 38A | Lumens 1 and 4 = 0.140 inch<br>Lumens 2 and 3 = 0.70 inch |

TABLE 1-continued

Sheaths Constructed

Figure 38B:
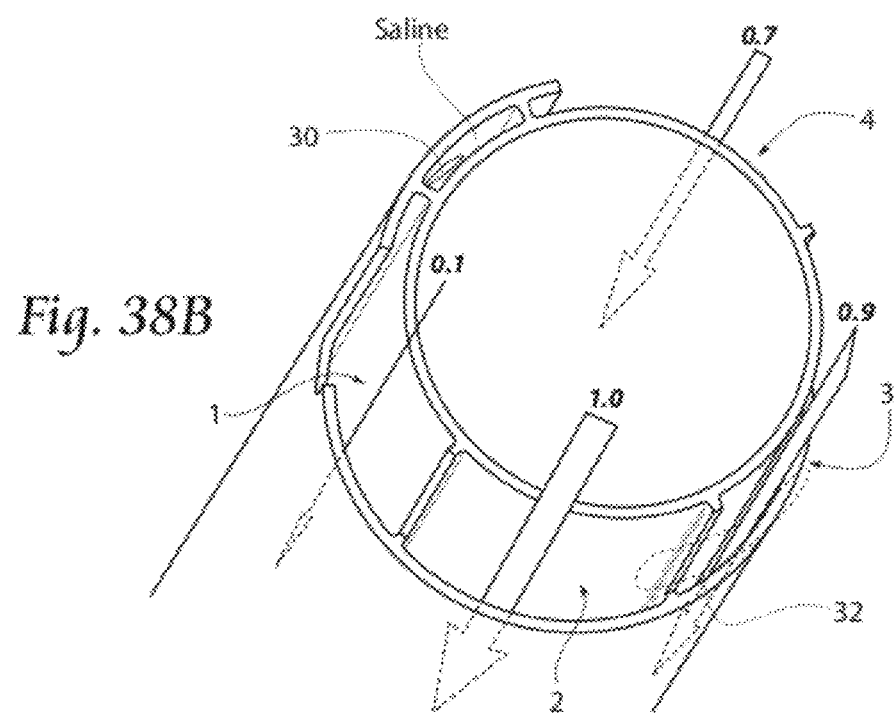
FIG. 38B is a perspective side view of the proximal end of an alternative embodiment of a sheath, trimmed to form a plenum that corresponds with Device 3 in Table 1 of Example 2, and annotated to show the relative air speeds of pressurized $CO_2$ that is directed and deflected within the plenum into the Lumens 1, 2, 3, and 4.
Figure 38C:
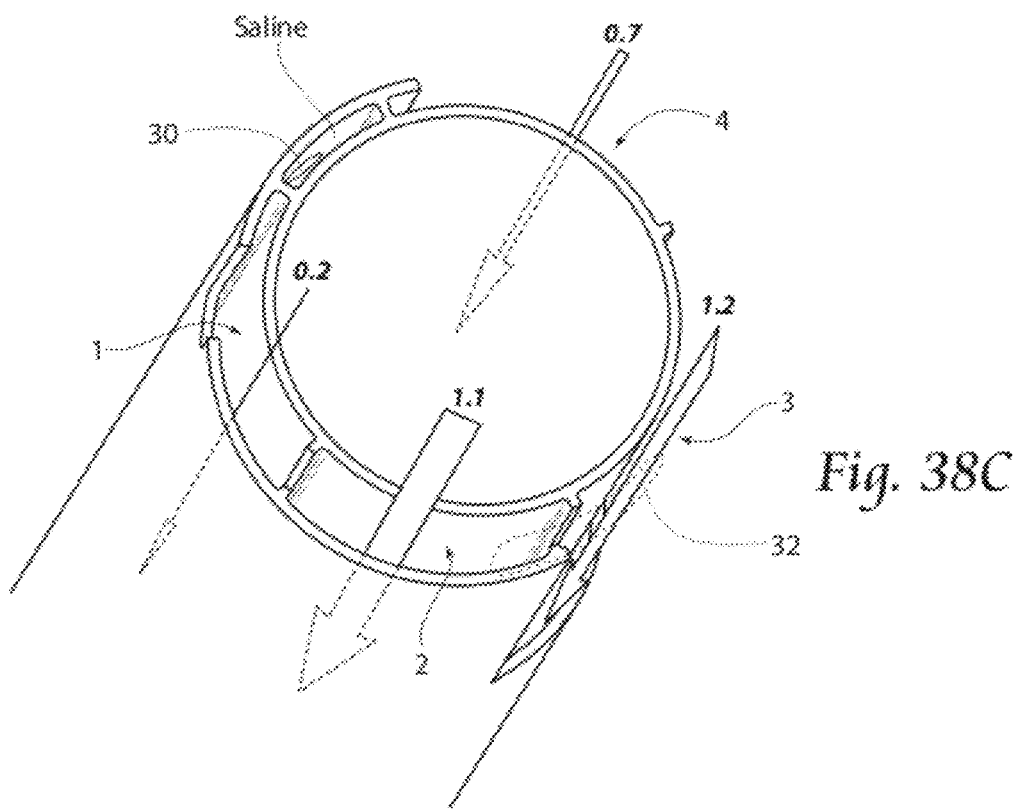
FIG. 38C is a perspective side view of the proximal end of an alternative embodiment of a sheath, trimmed to form a plenum that corresponds with Device 4 in Table 1 of Example 2, and annotated to show the relative air speeds of pressurized $CO_2$ that is directed and deflected within the plenum into the Lumens 1, 2, 3, and 4.
Figure 38D:
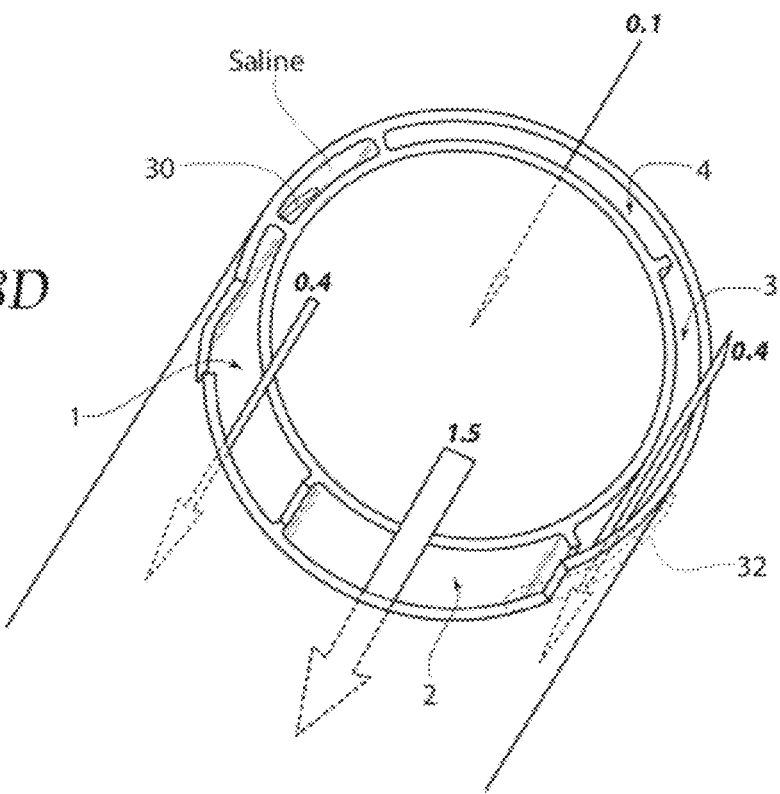
FIG. 38D is a perspective side view of the proximal end of an alternative embodiment of a sheath, trimmed to form a plenum that corresponds with Device 5 in Table 1 of Example 2, and annotated to show the relative air speeds of pressurized $CO_2$ that is directed and deflected within the plenum into the Lumens 1, 2, 3, and 4.
Figure 39:
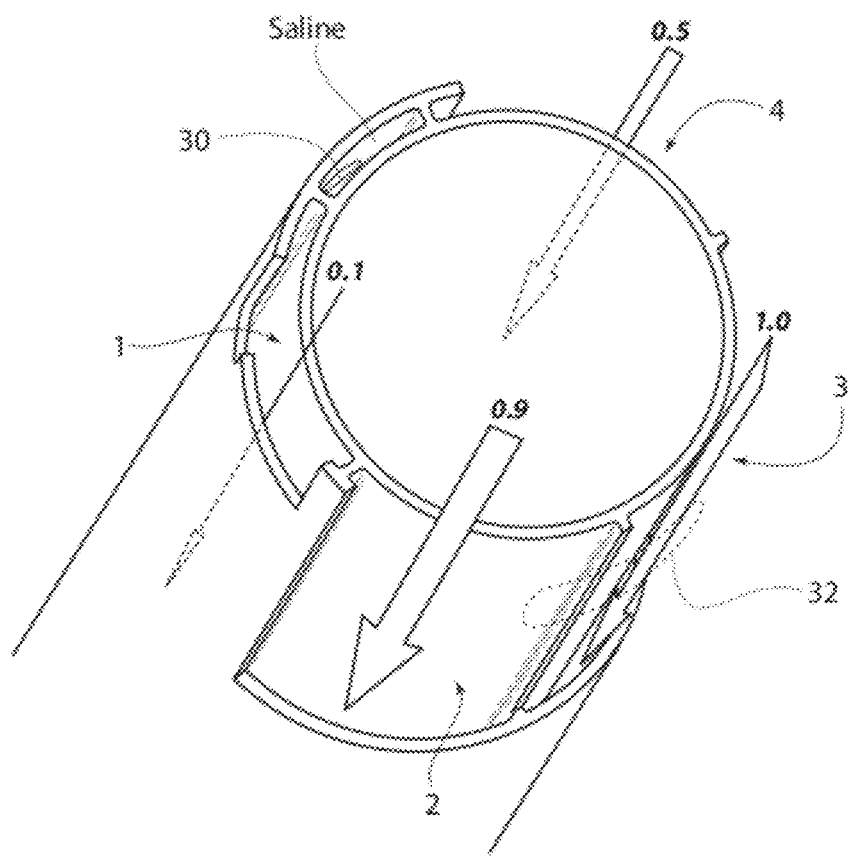
FIG. 39 is a perspective side view of the proximal end of an alternative embodiment of a sheath, trimmed to form a plenum that corresponds with Device 6 in Table 1 of Example 2, and annotated to show the relative air speeds of pressurized $CO_2$ that is directed and deflected within the plenum into the Lumens 1, 2, 3, and 4.
Figure 40A:
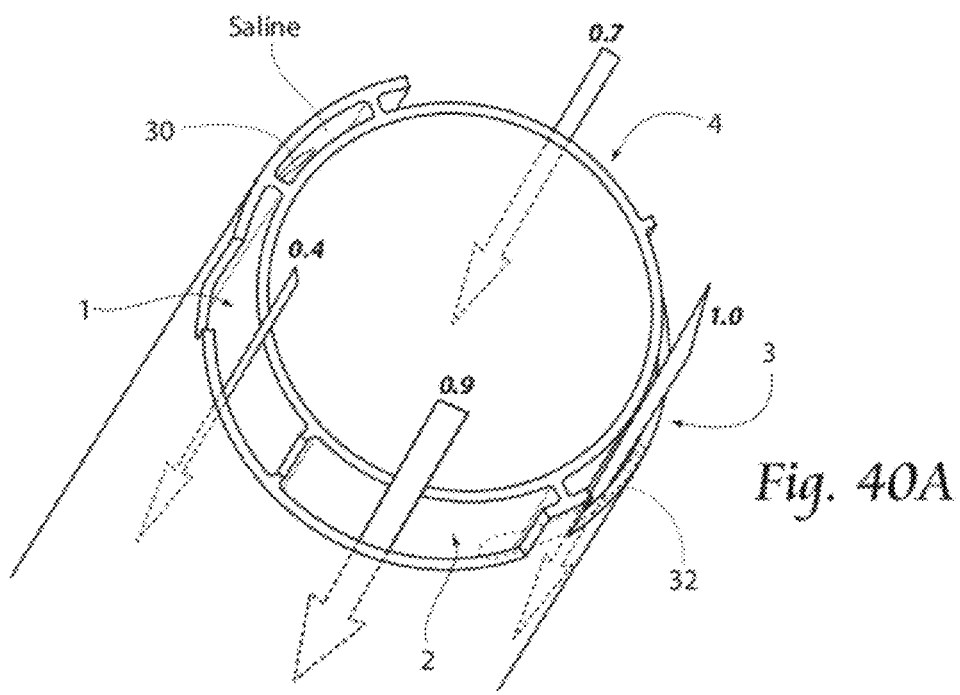
FIG. 40A is a perspective side view of the proximal end of an alternative embodiment of a sheath, trimmed to form a plenum that corresponds with Device 7 in Table 1 of Example 2, and annotated to show the relative air speeds of pressurized $CO_2$ that is directed and deflected within the plenum into the Lumens 1, 2, 3, and 4.
Figure 40B:
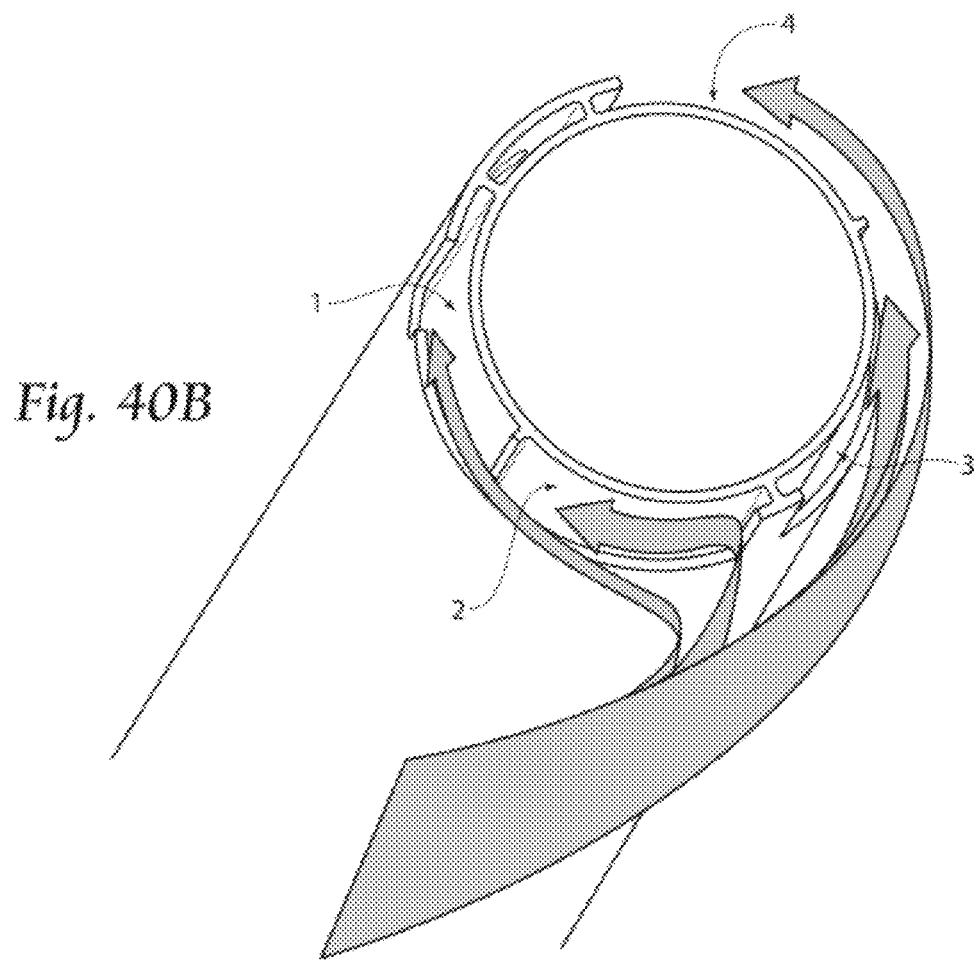
FIG. 40B is a perspective side view of the proximal end of the sheath shown in FIG. 33A, showing the direction and deflection of pressurized $CO_2$ introduced in the plenum, for entry into the Lumens 1, 2, 3, and 4.

| Device Designations | Proximal Plenum Configuration | Proximal Trim Distances |
|---|---|---|
| 3 | As Shown in FIG. 38B | All Lumens 0.330 inch |
| 4 | As Shown in FIG. 38C | Lumens 1, 2, and 4 = 0.140 inch<br>Lumen 3 = 0.70 |
| 5 | As Shown in FIG. 38D | Lumens 1 and 2 = 0.140 inch<br>Lumens 3 and 4 = 0.0 inch |
| 6 | As shown in FIG. 39A | Lumens 1 and 4 = 0.140 inch<br>Lumens 2 and 3 = 0.70 inch<br>Divider Between 1 and 2 at 0.140 inch |
| 7 | As Shown in FIG. 40A | All Lumens 0.140 inch<br>Divider Between 2 and 3 at 0.140 inch |

Pressurized $CO_2$ was conveyed into the plenum of each Device 1 to 7, at an entrance pressure of 15 mmHg and a flow rate of 14 L/min. Air speeds (m/sec) were measured coming out of each individual lumen (with no defection assembly attached at the distal end of the sheath) using a hot wire anemometer.

The air speeds measured are listed in the following Table 2:

TABLE 2

Sheath Performance (Lumen Air Speeds: No Tip)

| Device Designations | Air Speed Lumen 1 Without Deflection Tip (m/sec) | Air Speed Lumen 2 Without Deflection Tip (m/sec) | Air Speed Lumen 3 Without Deflection Tip (m/sec) | Air Speed Lumen 4 Without Deflection Tip (m/sec) |
|---|---|---|---|---|
| 1 | 0.2 | 1.7 | 0.7 | 0.6 |
| 2 | 0.1 | 1.1 | 1.3 | 0.8 |
| 3 | 0.1 | 1.0 | 0.9 | 0.7 |
| 4 | 0.2 | 1.1 | 1.2 | 0.7 |
| 5 | 0.4 | 1.5 | 0.4 | 0.1 |
| 6 | 0.1 | 0.9 | 1.0 | 0.5 |
| 7 | 0.4 | 0.9 | 1.0 | 0.7 |

Next, deflection assemblies 64 were attached to the distal end of the Devices 1 to 7. The deflector assemblies 64 including a reduced channel or gap distance Y of 0.005 inch (see FIG. 29.) The Devices 1 to 7 with deflection assemblies were mated with conventional 10 mm laparoscopes with different tip configurations, i.e., blunt tips (0°) and angled tips (30° and 45°). $CO_2$ was conveyed through the deflection assemblies 64 at an entry pressure of 15 mm Hg and an entry flow rate of 14 L/min. For each Device 1 to 7, the flow rate (L/min) of the $CO_2$ exiting the deflection assembly was measured using digital flow meters measured in conjunction with an Omega DAQ system, as was the air speed (m/sec) using a hot wire anemometer.

As described in Example 1, a plume of water vapor (mist) was created by an ultrasonic transducer and channel through a tube. The distal ends of Devices 1 to 7 (with deflection assemblies 64) were positioned over the plume as $CO_2$ is conveyed through the deflection assembly 64. The plume of water vapor was observed for the presence or absence of a rolling vortex. The presence of a rolling vortex for a 5 mm sheath is shown in FIGS. 25B and 28B.

The results are described in the following Table 3:

TABLE 3

Sheath Performance: Flow Rates/Plume Performance with Deflection Assemblies (.005 Gap)

| Device Designations | Flow Rate L/min | | | Air Speed m/sec | | | Plume |
|---|---|---|---|---|---|---|---|
| | Distal Tip Angle | | | | | | |
| | 0° | 30° | 45° | 0° | 30° | 45° | |
| 1 | 8.10 | 7.31 | 5.8 | 1.8 | 2.1 | 2.0 | No Distinct Vortex Entrainment (Lumen 1) |
| 2 | 7.40 | 6.51 | 7.6 | 2.0 | 1.7 | 2.1 | Small Air Curtain Entrainment (Lumen 1) |
| 3 | 6.80 | 6.35 | 6.71 | 1.5 | 1.5 | 1.8 | No Distinct Vortex Entrainment (Lumens 2 and 3) |
| 4 | 6.10 | 5.85 | 6.63 | 1.5 | 1.9 | 1.9 | Dual Vortex Entrainment (Lumen 4) |
| 5 | 6.60 | 6.65 | 6.40 | 1.8 | 1.7 | 2.0 | Entrainment (Lumens 3 and 4) |
| 6 | 7.10 | 6.3 | 6.25 | 1.8 | 1.4 | 1.5 | Dual Vortex But Very Turbulent Entrainment (Lumen 2) |
| 7 | 8.00 | 7.59 | 6.70 | 3.3 | 2.2 | 2.1 | Distinct Vortex Large Air Curtain No Entrainment |

As demonstrated in Table 2, $CO_2$ distribution within the plenum of the Devices 1 to 4 (FIGS. 37B; 38A; 38B; 38C, respectively) was comparable. In all Devices 1 to 4, Lumens 2 and 3 received most of the $CO_2$, and the other two Lumens 1 and 4 received less. Lumen 1 always had the lowest air speed. The direction and deflection and distribution of $CO_2$ within the plenum was not uniform. The maximum air speed measured at the other lumens ranged between 6 to 13 times the minimum air speed measured at Lumen 1.

In these configurations, the $CO_2$ travels within the plenum from the manifold to the sheath in a counter-clockwise rotation, away from Lumen 1. In order for the $CO_2$ to travel into and through Lumen 1, it has to travel the opposite clockwise direction i.e. against the flow. The proportions of the 5 mm plenum shown in FIGS. 29B and 29C directed and deflected and distributed the counterclockwise and clockwise flows within the plenum sufficiently to support a rolling vortex. However, as demonstrated in Table 3, the larger size proportions of the 10 mm plenum shown in FIGS. 37B; 38A; 38B; 38C did not direct and deflect and distribute the counterclockwise and clockwise flows within the plenum in a sufficiently uniform manner to support a rolling vortex. Further, entrainment occurred.

In Device 5 (FIG. 38D), Lumens 1 and 2 had a trim distance of 0.140, as in Device 1 (FIG. 37), but, unlike Device 1, Lumens 3 and 4 in Device 5 included no trim distance.

In the results observed for Device 5 in Table 2, like Device 1, Lumens 2 and 3 received most of the $CO_2$, and the other two Lumens 1 and 4 received less. However, in Device 5, Lumen 4 had the lowest air speed (the reverse of Device 1). As also observed in Devices 1 to 4, the direction and deflection and distribution of $CO_2$ within the plenum was not uniform. In Device 5, the maximum air speed at the other lumens was 15 times the minimum airspeed at Lumen 4 (for comparison, in Device 1, the maximum air speed at the other lumens was 8.5 times the minimum air speed at Lumen 1; in Devices 1 to 4, the difference ranged upward to 13 times).

Device 5 does demonstrate that the absence of any trim distance in the plenum can lead to a significant deterioration of air speed in the affected lumens. This demonstrates that the presence of a plenum is beneficial.

In Device 5, as in Devices 1 to 4, the size and configuration of the 10 mm plenum, as shown in FIG. 38D, did not direct and deflect and distribute the counterclockwise and clockwise flows within the plenum in a sufficiently uniform manner to support a rolling vortex. Still further, entrainment occurred.

In Device 6 (FIG. 32), the plenum was enlarged at Lumens 2 and 3, and an air divider was placed in the plenum between Lumens 1 and 2. Compared to Device 1 (FIG. 37B), the maximum air flow speed measured in Device 6 (1.0 m/sec at Lumen 3) deteriorated and changed lumens (in Device 1, the maximum air flow speed was 1.7 m/sec in Lumen 2). Compared to Devices 1 to 4, there was not an appreciable improvement in the minimum air flow speed (0.1 m/sec at Lumen 1), and the difference between maximum and minimum air speeds was great (10 times). The presence of the air divider in the 10 mm plenum shown in FIG. 27 did change the direction and deflection of $CO_2$ flow within the plenum, as a vortex developed. However, the vortex was not beneficial—there were dual vortices and turbulence. Further, entrainment persisted.

In Device 7 (FIG. 40A), an air divider was placed in the plenum between Lumens 2 and 3, and the plenum was equalized at a trim distance 0.140 inch at all lumens. Thus, Device 7 comprises Device 1 (FIG. 37B), with the addition of the air divider between Lumens 2 and 3. The presence of the air divider in Device 7 promoted counterclockwise $CO_2$ flow in the plenum sufficient to supply Lumens 3 and 4 with improved and more equalized air speeds, compared to Device 1. The presence of the air divider in Device 7 also intensified the clockwise $CO_2$ counter flow of $CO_2$ in the plenum sufficient to supply Lumens 1 and 2 with more equalized air speeds, compared to Device 1). The improved uniformity among the air speed was also noticed with respect to the difference between the maximum and minimum air speeds. The maximum air speed (in Lumen 3) in Device 7 was only 2.5 times the minimum air speed (in Lumen 1), compared to a difference of 8.5 times in Device 1.

Looking at the data of Table 3, which lists exit velocities measured at the distal end of Devices 1 to 7, it is difficult to determine why desirable results were achieved in Device 7, but undesirable results were achieved in Devices 1 to 6.

The data of Table 2, which lists air speeds of $CO_2$ directed, deflected, and distributed at the proximal plenum of Devices 1 to 7, it can be appreciated that it is a uniformity of deflection and direction and distribution of $CO_2$ at the proximal end of the sheath that provides the expectation that a desired vortex effect will be achieved at the distal end of the sheath. It was the proximal configuration of Device 7 that promoted, in a 10 mm sheath, improved counterclockwise $CO_2$ flow in the plenum sufficient to supply Lumens 3 and 4 with improved and more equalized air speeds (1.0 and 0.7, respectively). It was the proximal configuration of Device 7 that promoted intensified clockwise $CO_2$ counter flow of $CO_2$ in the plenum sufficient to supply Lumens 1 and 2 with more equalized air speeds (0.9 and 0.4 respectively). The improved uniformity among the air speed in Device 7 was also present with respect to the difference between the maximum and minimum air speeds. The maximum air speed (in Lumen 3) in Device 7 was only 2.5 times the minimum air speed (in Lumen 1), compared to a difference of 8.5 times in Device 1. The equalized air speeds in Lumens 2 and 3 in Device 7 also correlate with a desired positioning of the vortex at the 9 O'clock (090) Left Hand position, because it is at this position that $CO_2$ transported by the Lumens 2 and 3 exits the deflection assembly.

The foregoing Example 2 demonstrates that the creation of a desirable vortex pattern at the distal end of the sheath is the outcome of properly establishing desirable physical and pneumatic conditions at the proximal end of the sheath. The desirable vortex pattern that is created in this manner assures that particles are moved away from the lens, and not deposited or entrained on the lens. The desirable vortex pattern that is created also establishes a gas curtain across the lens sufficient to defog the lens.

IV. CONCLUSION

The view optimizing assembly as described herein prevents condensation from forming on the end of the laparoscope during surgery. It further reduces or eliminates the tendency for aerosolized debris from cautery or other energy sources from settling on the lens which can reduce visual acuity and waste time. The view optimizing assembly as described herein gives a surgeon an uninterrupted view of a laparoscopic operating field by defogging and deflecting debris from the lens of the laparoscope without having to remove the scope from the abdominal cavity for cleaning.

The invention claimed is:

1. A view optimizing assembly for use in combination with a laparoscope and a source of gas, the assembly comprising:
   a sheath having a proximal end and a distal end extending along a sheath axis, wherein the sheath is configured to be mounted over a shaft of the laparoscope and includes a first lumen and a second lumen extending from the proximal end to the distal end;
   a tubing set connecting the first and second lumens of the sheath to the source of gas;
   a deflector assembly attached to a distal end of the sheath and in communication with the first and second lumens;
   wherein a proximal-most portion of an outer wall of the sheath is trimmed relative to a proximal-most portion of an inner wall of the sheath such that a plenum forms around the proximal-most portion of the inner wall when air is supplied from the source of gas to the sheath, the plenum controlling the velocity of gas entering the first lumen and the velocity of gas entering the second lumen,
   wherein the first and second lumens are configured such that, when gas is provided from the tubing set, a velocity of gas through the first lumen is greater than a velocity of gas through the second lumen such that gas from the first and second lumens flows across the deflector assembly and combines to form a single vortex at the distal end of the sheath that spirals about a vortex axis to keep debris off of a lens of the laparoscope.

2. The optimizing assembly according to claim 1 further comprising:
   a manifold located on the proximal end of the sheath configured to couple the tubing set to the sheath.

3. The optimizing assembly of claim 2, wherein the manifold includes a quick exchange coupling configured to connect the tubing set to the sheath.

4. The optimizing assembly of claim 2, wherein the manifold includes a single gas inlet to convey gas from the tubing set to the first and second lumens of the sheath.

5. The optimizing assembly of claim 1 wherein the deflector assembly includes a stop on a proximal surface thereof configured to limit a distance the sheath may be inserted over the laparoscope.

6. The optimizing assembly of claim 1 further comprising a locking collar located at said proximal end of said sheath and configured, in use, to frictionally engage the laparoscope and resist axial withdrawal of the laparoscope from the sheath.

7. The optimizing assembly of claim 1 wherein the deflector assembly is configured to be substantially parallel to a lens of the laparoscope.

8. The optimizing assembly of claim 1 wherein the deflector assembly is angled at a non-perpendicular angle with respect to a central axis of the laparoscope, the deflector assembly having a low end and a high end.

9. The optimizing assembly of claim 8 wherein the vortex forms across the lens of the laparoscope from the low end of the deflector assembly to the high end.

10. The optimizing assembly of claim 1 further comprising an in-line pumping device located in said tubing set, said pumping device configured to deliver cleaning fluid through a lumen of the sheath.

11. The optimizing assembly of claim 1 further comprising a bulb connected to the tubing set and configured to provide an air burst across the lens of the laparoscope.

12. A kit comprising the view optimizing assembly of claim 1.

13. The optimizing assembly of claim 1, wherein the sheath is rigid.

14. The optimizing assembly of claim 5, wherein a distal end of the laparoscope is configured to abut against the stop.

15. The optimizing assembly of claim 1, wherein the first lumen has a greater circumferential length than the second lumen.

16. The optimizing assembly of claim 1, wherein the source of gas is a source of insufflation gas.

17. The optimizing assembly of claim 1, wherein the vortex axis is oriented off of a central axis of the laparoscope.

\* \* \* \* \*